United States Patent [19]

Takeshiba et al.

[11] Patent Number: 5,614,470
[45] Date of Patent: Mar. 25, 1997

[54] 13-SUBSTITUTED MILBEMYCIN DERIVATIVES, THEIR PREPARATION AND THEIR USE

[75] Inventors: Hideo Takeshiba; Kazuo Sato; Toshiaki Yanai; Shinji Yokoi; Reiji Ichinose; Kinji Tanizawa, all of Shiga-ken, Japan

[73] Assignee: Sankyo Company, Limited, Tokyo, Japan

[21] Appl. No.: 412,687

[22] Filed: Mar. 29, 1995

[30] Foreign Application Priority Data

| Apr. 1, 1994 | [JP] | Japan | 6-064803 |
| Nov. 17, 1994 | [JP] | Japan | 6-283382 |
| Jan. 25, 1995 | [JP] | Japan | 7-009377 |

[51] Int. Cl.$^6$ ............ A01N 43/04; A61K 31/335
[52] U.S. Cl. ............ 504/291; 514/450; 549/264
[58] Field of Search ............ 549/264; 514/450; 504/291

[56] References Cited

U.S. PATENT DOCUMENTS

| 4,547,520 | 10/1985 | Ide et al. | 514/450 |
| 4,945,105 | 7/1990 | Sato et al. | 514/450 |
| 4,963,582 | 10/1990 | Sato et al. | 514/450 |
| 5,276,033 | 1/1994 | Yanai et al. | 549/264 |
| 5,346,918 | 9/1994 | Morisawa et al. | 514/450 |
| 5,405,867 | 4/1995 | Sato et al. | 514/450 |
| 5,428,034 | 6/1995 | Morisawa et al. | 549/264 |

FOREIGN PATENT DOCUMENTS

| 0246739 | 11/1987 | European Pat. Off. |
| 0341972 | 11/1989 | European Pat. Off. |
| 0357460 | 3/1990 | European Pat. Off. |
| 0448243 | 9/1991 | European Pat. Off. |
| 0444964 | 9/1991 | European Pat. Off. |

OTHER PUBLICATIONS

Akio Saito et al, Synthesis and Anthelmintic Activity Of 13-Alkoxymilbemycin Derivatives, vol. 46, No. 8, Aug. 1993, Tokyo JP, pp. 1252–1264.

Primary Examiner—Amelia Owens
Attorney, Agent, or Firm—Frishauf, Holtz, Goodman, Langer & Chick, P.C.

[57] ABSTRACT

13-Substituted milbemycin derivatives having the formula (I):

wherein:
  $R^1$ is methyl, ethyl, isopropyl or sec-butyl;
  $R^2$ is hydrogen or alkyl;
  X is ($\alpha$-hydroxyimino- or $\alpha$-alkoxyimino-substituted)-arylmethyl or ($\alpha$-hydroxyimino- or $\alpha$-alkoxyimino-substituted)-heterocyclylmethyl, N-substituted-aminophenyl or N-substituted-aminophenoxy;
  m is 0 or 1; and n is 0 or 1;
are valuable as agricultural and horticultural anthelmintic, acaricidal and insecticidal agents.

26 Claims, No Drawings

13-SUBSTITUTED MILBEMYCIN DERIVATIVES, THEIR PREPARATION AND THEIR USE

BACKGROUND OF THE INVENTION

The present invention relates to a series of new derivatives of the compounds known as the "milbemycins", which derivatives are substituted at the 13-position. The invention also provides new methods and compositions using these compounds for agricultural and horticultural purposes, as well as processes for preparing them.

There are several classes of known compounds with a structure based on a 16-membered macrolide ring, which compounds are obtained by fermentation of various microorganisms or are obtained semi-synthetically by chemical derivatization of such natural fermentation products, and which exhibit acaricidal, insecticidal, anthelmintic and antiparasitic activities. The milbemycins and avermectins are examples of two such classes of known compounds, but various others also exist and are identified in the art by different names or code numbers. The names for these various macrolide compounds have generally been taken from the names or code numbers of the microorganisms which produce the naturally occurring members of each class, and these names have then been extended to cover the chemical derivatives of the same class, with the result that there has been no standardized systematic nomenclature for such compounds generally.

In order to avoid confusion, a standardized system of nomenclature will be used herein, which follows the normal rules for naming derivatives of organic compounds as recommended by the International Union of Pure and Applied Chemistry (IUPAC), Organic Chemistry Division, Commission on Nomenclature of Organic Chemistry, and which is based primarily on the hypothetical parent compound hereby defined as "milbemycin" and represented by the formula (A):

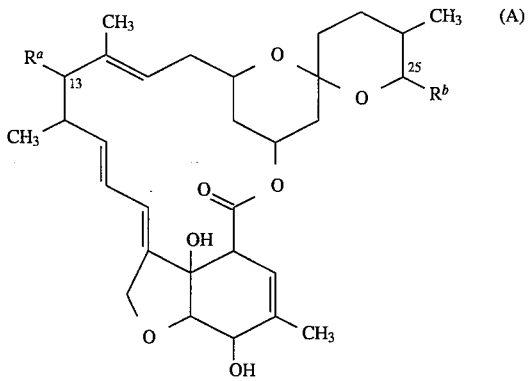

wherein $R^a$ and $R^b$ both represent hydrogen atoms.

For the avoidance of doubt, formula (A) also shows the numbering of positions of the macrolide ring system applied to those positions most relevant to the compounds of the present invention and of the prior art.

The naturally produced milbemycins are a series of macrolide compounds known to have anthelmintic, acaricidal and insecticidal activities. Milbemycin D was disclosed in U.S. Pat. No. 4,346,171, where it was referred to as "Compound B-41D", and milbemycins $A_3$ and $A_4$ were disclosed in U.S. Pat. 3,950,360. These compounds may be represented by the above formula (A) in which $R^a$ at position 13 is a hydrogen atom and $R^b$ at position 25 is a methyl group, an ethyl group or an isopropyl group, these compounds being designated as milbemycin $A_3$, milbemycin $A_4$ and milbemycin D, respectively. The milbemycin analogs having a hydrogen atom at position 13 and substituted at position 25 with a sec-butyl or an isopropyl group, respectively, were disclosed in U.S. Pat. No. 4,173,571 as "13-deoxy-22,23-dihydroavermectin $B_{1a}$ aglycone" and "13-deoxy-22,23-dihydroavermectin $B_1b$ aglycone"; and the corresponding 13-glycosylated compounds are known as "22,23-dihydro-avermectin $B_{1a}$" and "22,23-dihydro-avermectin $B_1b$".

Subsequently, various derivatives of the original milbemycins and avermectins have been prepared and their activities investigated. For example, 5-esterified milbemycins have been disclosed in U.S. Pat. Nos. 4,199,569, 4,201,861, 4,206,205, 4,173,571, 4,171,314, 4,203,976, 4,289,760, 4,457,920, 4,579,864 and 4,547,491, in European Patent Publications 8184, 102,721, 115,930, 180,539 and 184,989 and in Japanese Patent Applications Kokai (i.e. as laid open to public inspection) 57-120589 and 59-16894.

13-Hydroxy-5-ketomilbemycin derivatives have been disclosed in U.S. Pat. No. 4,423,209. Milbemycin 5-oxime derivatives were disclosed in U.S. Pat. No. 4,547,520 and in European Patent Publication 203 832. Milbemycin 23-oxime derivatives were disclosed in European Patent Publication 259,779; and milbemycin derivatives having an oximino substituent at the 13-position were disclosed in European Patent Publications 165,029 and 341,972, and in PCT Publication WO 93/18041.

Several compounds in which the 13-hydroxy group has been esterified are disclosed in U.S. Pat. No. 4,959,386, which describes esters of various carboxylic acids. None of the carboxylic acid moieties at the 13-position of these prior art compounds have heterocyclyl substituents. 13-Acetoxymilbemycin derivatives, in which the acetoxy group can be substituted by various heterocyclylthio groups, are disclosed in European Patent Publication 549 273. European Patent Publication 246 739 discloses 13-alkanoic ester milbemycins which can be substituted at the α-position of the alkanoyl group by various moieties including arylmethyl, heterocyclylmethyl, phenoxy and heterocyclyloxy groups.

None of the carboxylic acid moieties at the 13-position in these prior art compounds have an alkoxyimino substituent, or have an aryl or heterocyclyl substituent having substituted-amino ring substituents.

A number of milbemycins having an ether group at the 13-position have been disclosed. Milbemycins having a phenylalkoxy group at the 13-position are disclosed in European Patent Publications 448 243, 444 964, 357 460 and 594 291.

13-Ether milbemycins in which the alkoxy group has an aryloxyimino or a heterocyclyloxyimino substituent have not been disclosed in the prior art.

The various classes of milbemycin-related macrolide compounds referred to above are all disclosed as having one or more types of activity as antibiotic, anthelmintic, ectoparasiticidal, acaricidal or other pesticidal agents. However, there is still a continuing need to provide such agents with improved activity against one or more classes of agricultural and horticulural pests.

It has now been discovered that the activity of such milbemycin-related derivatives can be improved by appropriately selecting the combination of substituents on the macrolide ring system, especially the substituents at position 13. In particular, it has now been found that the activity of the compounds can be improved upon by appropriate selection of certain highly specific ester and ether groups at the 13 position, as specified below. In general, the compounds of the present invention tend to have a better pesticidal activity than do the compounds of the prior art, and many of the compounds of the present invention have a very substantially better activity.

BRIEF SUMMARY OF INVENTION

Accordingly, it is an object of the present invention to provide such macrolide compounds having improved activity. It is another object of the invention to provide methods for preparing such compounds. It is a still further object of the invention to provide pesticidal compositions and methods using the said compounds.

In accordance with these objects, the invention provides compounds having the formula (I):

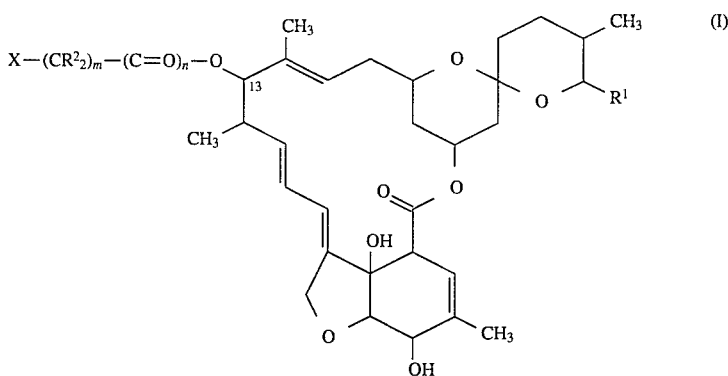

wherein:
R¹ represents a methyl, ethyl, isopropyl or sec-butyl group;
R² represents a hydrogen atom or an alkyl group having from 1 to 3 carbon atoms;
X represents:
(a) a group having the formula (II):

$$\underset{Y-C-}{\overset{N-OR^3}{\|}} \quad (II)$$

wherein:
R³ represents a hydrogen atom, or an alkyl group having from 1 to 4 carbon atoms; and
Y represents an aryl group having from 6 to 10 carbon atoms or a heterocyclyl group, said aryl group and said heterocyclyl group optionally being substituted with 1 or 2 substituents (which may be the same or different) selected from Substituents A below;
or
(b) a group having the formula (III):

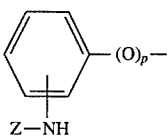

wherein:
p=0 or 1; and
Z represents:
an alkanoyl group having from 2 to 3 carbon atoms;
an alkylsulfonyl group having from 1 to 3 carbon atoms;
an alkoxycarbonyl group having from 2 to 5 carbon atoms;

an aminoalkanoyl group having from 2 to 7 carbon atoms (the amino group of said aminoalkanoyl group optionally being substituted by 1 or 2 subtituents, which may be the same or different, selected from Substituents B below, and the alkanoyl portion of said aminoalkanoyl group optionally being substituted by a phenyl group or by an alkylthio group having from 1 to 3 carbon atoms);
a saturated 5- or 6-membered heterocyclylcarbonyl group containing nitrogen as a ring atom and optionally also containing sulfur as a ring atom, in which said nitrogen ring atom may optionally be substituted by a substituent selected from the Substituents B below, and in which the carbonyl group is attached to an atom other than said nitrogen ring atom;
a 5- or 6-membered lactamcarbonyl group, in which the nitrogen atom may optionally be substituted by a substituent selected from the Substituents B below, and in which the carbonyl group is attached to an atom other than the lactam nitrogen atom;
an α-alkoxyimino-α-heterocyclylacetoxy group, in which the alkoxy moiety has from 1 to 3 carbon atoms, and the heterocyclyl moiety is a 5- or 6-membered aromatic heterocyclic group which may optionally be substituted by one or two substituents selected from an amino group, a substituted amino group (substituted by one or two substituents, which may be the same or different, selected from Substituents B below), a halogen atom and an alkyl group having from 1 to 3 carbon atoms;
Substituents A comprise:
a halogen atom;
a nitro group;
a hydroxy group;
an alkoxy group having from 1 to 4 carbon atoms;
an aralkyloxy group having from 7 to 11 carbon atoms;
an amino group;
an alkanoylamino group having from 1 to 4 carbon atoms;
a haloalkanoylamino group having from 2 to 4 carbon atoms;
an alkylsulfonylamino group having from 1 to 3 carbon atoms;
an alkoxycarbonylamino group having from 2 to 5 carbon atoms;
a haloalkoxycarbonylamino group having from 3 to 5 carbon atoms;
an aminoalkanoylamino group having from 2 to 7 carbon atoms, in which the amino group of the aminoalkanoyl moiety may optionally be substituted by one or two substituents (which may be the same or different) selected from Substituents C below, and in which the alkanoyl moiety may optionally be substituted by a phenyl group or by an alkylthio group having from 1 to 3 carbon atoms; and a saturated 5- or 6-membered heterocyclylcarbonylamino group containing nitrogen as a ring atom, in which said nitrogen ring atom may optionally be substituted by a substituent selected from the Substituents C below, and in which the carbonylamino group is attached to an atom other than said nitrogen ring atom;

Substituents B Comprise:

an alkyl group having from 1 to 3 carbon atoms;

an alkanoyl group having from 2 to 3 carbon atoms;

a haloalkanoyl group having from 2 to 3 carbon atoms;

an aralkyl group having from 7 to 19 carbon atoms;

an alkoxycarbonyl group having from 2 to 5 carbon atoms;

a haloalkoxycarbonyl group having from 3 to 4 carbon atoms;

an arylcarbonyl group having from 7 to 11 carbon atoms;

an aralkyloxycarbonyl group having from 8 to 10 carbon atoms;

an alkoxycarbonylaminoalkanoyl group having from 1 to 4 carbon atoms in the alkoxy moiety and from 2 to 3 carbon atoms in the alkanoyl moiety; and an alkoxycarbonylaminoarylcarbonyl group having from 1 to 4 carbon atoms in the alkoxy moiety and from 6 to 10 carbon atoms in the aryl moiety;

Substituents C comprise:

an alkyl group having from 1 to 3 carbon atoms;

a formyl group;

an alkanoyl group having from 2 to 3 carbon atoms;

a haloakanoyl group having from 2 to 4 carbon atoms;

an alkoxycarbonyl group having from 2 to 5 carbon atoms;

a haloalkoxycarbonyl group having from 3 to 5 carbon atoms;

an arylcarbonyl group having from 7 to 11 carbon atoms; and an aralkyloxycarbonyl group having from 8 to 10 carbon atoms;

m=0 or 1; and n=0 or 1;

PROVIDED THAT, when X represents a group of the said formula (II), $R^2$ represents a hydrogen atom, and m and n cannot both be zero;

AND THAT, when X represents a group of the said formula (III), $R^2$ represents an alkyl group having from 1 to 3 carbon atoms, and m and n are both 1.

A sub-group of the compounds of formula (I) provided by the present invention are those wherein:

X represents a group having the said formula (II);

Substituents A are selected from a halogen atom, a nitro group, a hydroxy group, an alkoxy group having from 1 to 4 carbon atoms, an aralkyloxy group having from 7 to 11 carbon atoms, an amino group, an alkanoylamino group having from 1 to 4 carbon atoms, and a haloalkanoylamino group having from 2 to 4 carbon atoms; and $R^1$, $R^2$, $R^3$, Y, m and n all have the same meanings as defined for formula (I).

A second sub-group of the compounds of formula (I) provided by the present invention are those wherein:

X represents a group having the said formula (III) in which the substituent Z—NH— is attached at the para-position of the phenyl ring; and $R^1$, $R^2$, Z, m, n and p all have the same meanings as defined for formula (I).

A third sub-group of the compounds of formula (I) provided by the present invention are those wherein:

X represents a group having the said formula (II);

Y represents a phenyl group which is substituted at the para-position with an alkylsulfonylamino group having from 1 to 3 carbon atoms, an alkoxycarbonylamino group having from 2 to 5 carbon atoms, a haloalkoxycarbonylamino group having from 3 to 5 carbon atoms, an aminoalkanoylamino group having from 2 to 7 carbon atoms (in which the amino group of the aminoalkanoyl moiety may optionally be substituted by one or two substituents, which may be the same or different, selected from Substituents C, and in which the alkanoyl moiety may optionally be substituted by a phenyl group or by an alkylthio group having from 1 to 3 carbon atoms), or a saturated 5- or 6-membered heterocyclylcarbonylamino group containing nitrogen as a ring atom (in which said nitrogen ring atom may optionally be substituted by a substituent selected from Substituents C, and in which the carbonylamino group is attached to an atom other than said nitrogen ring atom); and $R^1$·$R^2$, $R^3$, m, n and Substituents C all have the same meanings as defined for formula (I).

The invention further provides an anthelmintic, acaricidal and insecticidal composition comprising an anthelmintic, acaricidal and insecticidal compound in admixture with an agriculturally or horticulturally acceptable carrier or diluent, wherein said compound is selected from the group consisting of compounds of formula (I).

The invention still further provides a method of protecting plants from damage by parasites selected from the group consisting of acarids, helminths and insects, which comprises applying an active compound to said plants or to parts of or reproductive matter (e.g. seeds) of said plants or to a locus including said plants or parts of said plants or reproductive matter of said plants, wherein the active compound is selected from the group consisting of compounds of formula (I).

DETAILED DESCRIPTION OF THE INVENTION

In the compounds of formula (I), the group $R^1$ is preferably a methyl or ethyl group, and more preferably an ethyl group.

When $R^2$ represents an alkyl group having from 1 to 3 carbon atoms this may be a straight or branched chain group, for example a methyl, ethyl, propyl or isopropyl group, preferably a methyl or ethyl group, and more preferably a methyl group.

In the compounds wherein X represents a group of the above-defined formula (II):

When $R^3$ represents an alkyl group having from 1 to 4 carbon atoms, this may be a straight or branched chain group, for example a methyl, ethyl, propyl, isopropyl, butyl, isobutyl, sec-butyl or t-butyl group, preferably a methyl or ethyl group, and more preferably a methyl group.

When Y represents a heterocyclic group, this is preferably a 5- or 6-membered heterocyclic group having 1 or 2 ring heteroatoms selected from nitrogen, oxygen and sulfur, for example a furyl, thienyl, oxazolyl, thiazolyl, pyrimidinyl, pyridazinyl, pyrazinyl or pyridyl group; and it is preferably a furyl, thienyl, oxazolyl, thiazolyl, pyridyl or pyrimidinyl group, more preferably a furyl, thienyl, oxazolyl, thiazolyl or pyridyl group, and most preferably a 3-furyl, 2-thienyl, 4-oxazolyl, 4-thiazolyl or 2-pyridyl group.

When Y represents a aryl group having from 6 to 10 carbon atoms, this is preferably a phenyl or naphthyl group, particularly a phenyl group.

In the compounds wherein X represents a group of the above-defined formula (III):

When Z represents an alkanoyl group having from 2 to 3 carbon atoms, this may be an acetyl or propionyl group and is preferably an acetyl group.

When Z represents an alkylsulfonyl group having from 1 to 3 carbon atoms this may be a straight or branched chain group, for example a methanesulfonyl, ethanesulfonyl, propanesulfonyl or isopropylsulfonyl group, and is preferably a methanesulfonyl group.

When Z represents an alkoxycarbonyl group having from 2 to 5 carbon atoms this may be a straight or branched chain group, for example a methoxycarbonyl, ethoxycarbonyl, propoxycarbonyl, isopropoxycarbonyl, butoxycarbonyl, isobutoxycarbonyl, sec-butoxycarbonyl or t-butoxycarbonyl group, and is preferably a methoxycarbonyl group.

When Z represents an aminoalkanoyl group having from 2 to 7 carbon atoms, the alkanoyl moiety will consist of an alkyl portion (having from 1 to 6 carbon atoms) which may be a straight or branched chain alkyl group or a cycloalkyl group, and which may optionally be substituted by a phenyl group or an by alkylthio group having from 1 to 3 carbon atoms. The optional alkylthio substituent on this group may itself be a straight or branched chain group having from 1 to 3 carbon atoms, such as a methylthio, ethylthio, propylthio or isopropylthio group, preferably a methylthio group. Examples of this optionally substituted aminoalkanoyl group include aminoacetyl, 2-aminopropionyl, 3-aminopropionyl, 2-aminobutyryl, 3-aminobutyryl, 4-aminobutyryl, 3-amino-3-methylpropionyl, 2-amino-2-methylpropionyl, 2-aminopentanoyl, 3-aminopentanoyl, 4-aminopentanoyl, 5-aminopentanoyl, 2-amino-3-methylbutyryl, 2-amino-2-methylbutyryl, 1-aminocyclobutane-1-carbonyl, 2-aminohexanoyl, 3-aminohexanoyl, 4-aminohexanoyl, 5-aminohexanoyl, 2-amino-3-methylpentanoyl, 2-amino-4-methylpentanoyl, 2-amino-3,3-dimethylbutyryl, 1-aminocyclopentane-1-carbonyl, 2-aminoheptanoyl, 1-aminocyclohexyl-1-carbonyl, α-aminophenylacetyl, 2-amino-3-phenylpropionyl, 2-amino-4-phenylbutyryl, 2-amino-3-methylthiopropionyl, 2-amino-3-ethylthiopropionyl, 2-amino-3-propylthiopropionyl, 2-amino-3-isopropylthiopropionyl, 2-amino-4-methylthiobutyryl, 2-amino-4-ethylthiobutyryl, 2-amino-4-propylthiobutyryl and 2-amino-4-isopropylthiobutyryl. It is preferably an aminoacetyl, 2-aminopropionyl, 3-aminopropionyl, 2-amino-2-methylpropionyl, 2-amino-3-methylbutyryl, 2-amino-3,3-dimethylbutyryl, 2-amino-4-methylpentanoyl, 1-aminocyclohexyl-1-carbonyl, α-aminophenylacetyl or 2-amino-4-methylthiobutyryl group, and more preferably an aminoacetyl, 2-aminopropionyl, 3-aminopropionyl, 2-amino-2-methylpropionyl, 2-amino-3-methylbutyryl or 1-aminocyclohexyl-1-carbonyl group; and particularly preferably an aminoacetyl, 2-aminopropionyl or 3-aminopropionyl group.

When Z represents a saturated 5- or 6-membered heterocyclylcarbonyl group containing nitrogen as a ring atom and also optionally containing sulfur as a ring atom this may be, for example, a pyrrolidine-2-carbonyl, pyrrolidine-3-carbonyl, piperidine-2-carbonyl, piperidine-4-carbonyl or thiazolidine-4-carbonyl group, and is preferably a pyrrolidine-2-carbonyl or thiazolidine-4-carbonyl group.

When Z represents a 5- or 6-membered lactamcarbonyl group this may be, for example, a γ-lactam-5-carbonyl or δ-lactam-6-carbonyl group, preferably a γ-lactam-5-carbonyl group.

When Z represents an α-alkoxyimino-α-heterocyclylacetoxy group, the alkoxy moiety of this has from 1 to 3 carbon atoms and may be straight or branched, for example methoxy, ethoxy, propoxy or isopropoxy, and is preferably a methoxy. The heterocyclyl moiety consists of an aromatic 5- or 6-membered heterocyclic group, which may have one or two heteroatoms selected from nitrogen, oxygen and sulfur, for example, a furyl, thienyl, oxazolyl or thiazolyl group, preferably a 2-furyl, 2-thienyl or 4-thiazolyl group. This heterocyclic group may optionally be substituted with one or two substituents (which may be the same or different) selected from amino, halogen, and alkyl groups having from one to three carbon atoms. The optional amino substituent may itself optionally be substituted with one or two substituents (which may be the same or different) selected from Substituents B as defined below. The optional halogen substituent may be fluorine, chlorine, bromine or iodine, and is preferably fluorine, chlorine or bromine. The optional alkyl substituent may be a straight or branched chain group, for example a methyl, ethyl, propyl or isopropyl group, preferably a methyl group.

Substituents A

When the optional substituent A is a halogen atom, this may be a fluorine, chlorine, bromine or iodine atom and is preferably a fluorine, chlorine or bromine atom, more preferably a fluorine or chlorine atom.

When the optional substituent A is an alkoxy group having from 1 to 4 carbon atoms, this may be a straight or branched chain group, for example a methoxy, ethoxy, propoxy, isopropoxy, butoxy, isobutoxy, sec-butoxy or t-butoxy group, preferably a methoxy or ethoxy group, and more preferably an ethoxy group.

When the optional substituent A is an aralkyloxy group having from 7 to 11 carbon atoms this may be, for example, a benzyloxy, phenethyloxy, phenylpropyloxy or naphthylmethyloxy group, preferably a benzyloxy or phenethyloxy group.

When the optional substituent A is an alkanoylamino group having from 1 to 4 carbon atoms, this may be a straight or branched chain group, for example a formylamino, acetylamino, propionylamino, butyrylamino, isobutyrylamino, sec-butyrylamino or t-butyrylamino group, preferably an acetylamino or isobutyrylamino group, and more preferably an acetylamino group.

When the optional substituent A is a halogen-substituted alkanoylamino group having from 2 to 4 carbon atoms, this may be a straight or branched chain group substituted by from 1 to 3 halogen atoms (i.e. fluorine, chlorine, bromine or iodine, preferably fluorine, chlorine or bromine, more preferably chlorine or bromine), for example a chloroacetylamino, bromoacetylamino, dichloroacetylamino, trifluoroacetylamino or α-bromoisobutyrylamino group, preferably a chloroacetylamino, bromoacetylamino or trifluoroacetylamino group, and more preferably a chloroacetylamino or bromoacetylamino group.

When the optional substituent A is an alkylsulfonylamino group having from 1 to 3 carbon atoms, this may be a straight or branched chain group, for example a methylsulfonylamino, ethylsulfonylamino, propylsulfonylamino or isopropylsulfonylamino group, preferably a methylsulfonylamino or ethylsulfonylamino group, and more preferably a methylsulfonylamino group.

When the optional substituent A is an alkoxycarbonylamino group having from 2 to 5 carbon atoms this may be a straight or branched chain group, for example a methoxycarbonylamino, ethoxycarbonylamino, propoxycarbonylamino, isopropoxycarbonylamino, butoxycarbonylamino, isobutoxycarbonylamino, sec-butoxycarbonylamino or t-butoxycarbonylamino group, preferably one having from 2 to 3 carbon atoms, and most preferably a methoxycarbonylamino group.

When the optional substituent A is a haloalkoxycarbonylamino group having from 3 to 5 carbon atoms, this may be a straight or branched chain group substituted by from 1 to 3 halogen atoms (i.e. fluorine, chlorine, bromine or iodine), for example a 2-fluoroethoxycarbonylamino, 3,3,3-trichloroethoxycarbonylamino, 3-bromopropoxycarbonylamino or 4-chlorobutoxycarbonylamino group, preferably one having from 2 to 3 carbon atoms, more preferably a 3,3,3-trichloroethoxycarbonylamino group.

When the optional substituent A is an aminoalkanoylamino group having from 2 to 7 carbon atoms, the alkanoyl moiety will consist of an alkyl portion (having from 1 to 6 carbon atoms) which may be a straight or branched chain alkyl group or a cycloalkyl group, and which may optionally be substituted by a phenyl group or an by alkylthio group having from 1 to 3 carbon atoms. The optional alkylthio substituent on this group may itself be a straight or branched chain group having from 1 to 3 carbon atoms, such as a methylthio, ethylthio, propylthio or isopropylthio group, preferably a methylthio group. Examples of this optionally substituted aminoalkanoylamino group include aminoacetylamino, 2-aminopropionylamino, 3-aminopropionylamino, 2-aminobutyrylamino, 3-aminobutyrylamino, 4-aminobutyrylamino, 3-amino-3-methylpropionylamino, 2-amino-2-methyl- propionylamino, 2-aminopentanoylamino, 3-aminopentanoylamino, 4-aminopentanoylamino, 5-aminopentanoylamino, 2-amino-3-methylbutyrylamino, 2-amino-2-methylbutyrylamino, 1-aminocyclobutane-1-carbonylamino, 2-aminohexanoylamino, 3-aminohexanoylamino, 4-aminohexanoylamino, 5-aminohexanoylamino, 2-amino-3-methylpentanoylamino, 2-amino-4-methylpentanoylamino, 2-amino-3,3-dimethylbutyrylamino, 1-aminocyclopentane-1-carbonylamino, 2-aminoheptanoylamino, 1-aminocyclohexyl-1-carbonylamino, α-aminophenylacetylamino, 2-amino-3-phenylpropionylamino, 2-amino-4-phenylbutyrylamino, 2-amino-3-methylthiopropionylamino, 2-amino-3-ethylthiopropionylamino, 2-amino-3-propylthiopropionylamino, 2-amino-3-isopropylthiopropionylamino, 2-amino-4-methylthiobutyrylamino, 2-amino-4-ethylthiobutyrylamino, 2-amino-4-propylthiobutyrylamino and 2-amino-4-isopropylthiobutyrylamino. It is preferably an aminoacetylamino, 2-aminopropionylamino, 3-aminopropionylamino, 2-amino-2-methylpropionylamino, 2-amino-3-methylbutyrylamino, 2-amino-3,3-dimethylbutyrylamino, 2-amino-4-methylpentanoylamino, 1-aminocyclohexyl-1-carbonylamino, α-aminophenylacetylamino or 2-amino-4-methylthiobutyrylamino group, more preferably an aminoacetylamino, 2-aminopropionylamino, 3-aminopropionylamino, 2-amino-2-methylpropionylamino, 2-amino-3-methylbutyrylamino or 1-aminocyclohexyl-1-carbonylamino group, and particularly preferably an aminoacetylamino, 2-aminopropionylamino or 3-aminopropionylamino group.

When the optional substituent A is a 5- or 6-membered saturated heterocyclylcarbonylamino group containing a nitrogen heteroatom in the ring, the carbonylamino group can be attached to any of the ring atoms other than the nitrogen ring atom. Examples of such heterocyclylcarbonylamino groups include pyrrolidine-2-carbonylamino, pyrrolidine-3-carbonylamino, piperidine-2-carbonylamino and piperidine-4-carbonylamino groups, and the pyrrolidine-2-carbonylamino group is preferred.

Substituents B

When the optional substituent B is an alkyl group having from 1 to 3 carbon atoms, this may be a straight or branched chain group, for example a methyl, ethyl, propyl or isopropyl group, preferably a methyl group.

When the optional substituent B is an alkanoyl group having from 2 to 3 carbon atoms this may be an acetyl or propionyl group and is preferably an acetyl group.

When the optional substituent B is a haloalkanoyl group having from 2 to 3 carbon atoms this may be substituted by from 1 to 3 halogen atoms (i.e. fluorine, chlorine, bromine or iodine), and is preferably a chloroacetyl group.

When the optional substituent B is an aralkyl group having from 7 to 19 carbon atoms this may be, for example, a benzyl, diphenylmethyl or triphenylmethyl group and is preferably a triphenylmethyl group.

When the optional substituent B is an alkoxycarbonyl group having from 2 to 5 carbon atoms this may be a straight or branched chain group, for example a methoxycarbonyl, ethoxycarbonyl, propoxycarbonyl, isopropoxycarbonyl, butoxycarbonyl, isobutoxycarbonyl, sec-butoxycarbonyl or t-butoxycarbonyl group, and is preferably a methoxycarbonyl group.

When the optional substituent B is a haloalkoxycarbonyl group having from 3 to 4 carbon atoms, this may be a straight or branched chain group substituted by from 1 to 3 halogen atoms (i.e. fluorine, chlorine, bromine or iodine) and is preferably a 2,2,2-trichloroethoxycarbonyl group.

When the optional substituent B is an arylcarbonyl group having from 7 to 11 carbon atoms this may be a benzoyl or naphthoyl group and is preferably a benzoyl group.

When the optional substituent B is an aralkyloxycarbonyl group having from 8 to 10 carbon atoms, this may have a straight or branched alkyl moiety and may be, for example, a benzyloxycarbonyl, phenylethoxycarbonyl or phenylpropyloxycarbonyl group, preferably a benzyloxycarbonyl group.

When the optional substituent B is an alkoxycarbonylaminoalkanoyl group having from 1 to 4 carbon atoms in its alkoxy moiety (which may be straight or branched) and from 2 to 3 carbon atoms in its alkanoyl moiety, these may be respectively one of the alkoxycarbonyl and alkanoyl groups mentioned above, and the whole substituent is preferably a methoxycarbonylaminoacetyl group.

When the optional substituent B is an alkoxycarbonylaminoarylcarbonyl group having from 1 to 4 carbon atoms in its alkoxy moiety (which may be straight or branched) and from 6 to 10 carbon atoms in its aryl moiety, these may be respectively one of the alkoxycarbonyl and arylcarbonyl groups mentioned above, and the whole substituent is preferably a 4-(methoxycarbonylamino)benzoyl group.

Substituents C

When the optional substituent C is an alkyl group having from 1 to 3 carbon atoms this may be a straight or branched chain group, for example a methyl, ethyl, propyl or isopropyl group, preferably a methyl or ethyl group, and more preferably a methyl group.

When the optional substituent C is an alkanoyl group having from 2 to 3 carbon atoms this may be, for example, an acetyl or propionyl group and is preferably an acetyl group.

When the optional substituent C is a haloalkanoyl group having from 2 to 4 carbon atoms this may be a straight or branched chain group substituted by from 1 to 3 halogen atoms (i.e. fluorine, chlorine, bromine or iodine), for example a chloroacetyl, bromoacetyl, trifluoroacetyl, 2,3-dichloropropionyl or α-bromoisobutyryl group; preferably a chloroacetyl or bromoacetyl group.

When the optional substituent C is an alkoxycarbonyl group having from 2 to 5 carbon atoms this may be a straight or branched chain group, for example a methoxycarbonyl, ethoxycarbonyl, propoxycarbonyl, isopropoxycarbonyl, butoxycarbonyl, isobutoxycarbonyl, sec-butoxycarbonyl or a t-butoxycarbonyl group, and is preferably an alkoxycarbonyl group having from 2 to 3 carbon atoms, particularly preferably a methoxycarbonyl group.

When the optional substituent C is a haloalkoxycarbonyl group having from 3 to 5 carbon atoms this my be a straight or branched chain group substituted by from 1 to 3 halogen atoms (i.e. fluorine, chlorine, bromine or iodine), for example a 2-fluoroethoxycarbonyl, 3,3,3-trichloroethoxycarbonyl, 3-bromopropoxycarbonyl or 4-chlorobutoxycarbonyl group, and is preferably a haloalkoxycarbonyl group having from 3 to 4 carbon atoms; more preferably a 3,3,3-trichloroethoxycarbonyl group.

When the optional substituent C is an arylcarbonyl group having from 7 to 11 carbon atoms this may be, for example, a benzoyl or naphthoyl group and is preferably a benzoyl group.

When the optional substituent C is an aralkyloxycarbonyl group having from 7 to 9 carbon atoms this may be, for example, a benzyloxycarbonyl, phenylethoxycarbonyl or phenylpropoxycarbonyl group and is preferably a benzyloxycarbonyl group.

The preferred compounds of the invention in which X represents a group of the formula (II) are those wherein:

$R^1$ represents a methyl, ethyl, isopropyl or sec-butyl group;

$R^3$ represents a hydrogen atom, or a methyl or ethyl group; and

Y represents a phenyl, pyridyl, furyl, thienyl, oxazolyl or thiazolyl group which may optionally be substituted with the 1 or 2 substituents selected from the Substituents $A^1$ defined below.

The more preferred compounds of the invention in which X represents a group of the formula (II) are those wherein:

$R^1$ and $R^3$ each represents a methyl or ethyl group; and

Y represents a furyl, thienyl, thiazolyl, pyridyl or phenyl group which may optionally be substituted with 1 or 2 substituents selected from Substituents $A^2$ defined below.

Particularly preferred compounds of the invention in which X represents a group of the formula (II) are those wherein Y represents a phenyl group which may optionally be substituted at the para-position with a group selected from Substituents $A^3$ defined below.

The most preferred compounds of the invention in which X represents a group of the formula (II) are those wherein:

$R^1$ represents an ethyl group;

$R^3$ represents a methyl group;

Y represents a phenyl group, or a phenyl group substituted in the para-position with a methylsulfonylamino group or with a methoxycarbonylaminoacetylamino group; and m=0 and n=1.

The preferred compounds of the invention in which X represents a group of the formula (III) are those wherein:

Z represents an alkanoyl group having 2 or 3 carbon atoms; an alkylsulfonyl group having from 1 to 3 carbon atoms; an alkoxycarbonyl group having 2 or 3 carbon atoms; an aminoalkanoyl group having from 2 to 6 carbon atoms (in which the amino group may optionally be substituted by 1 or 2 substituents, which may be the same or different, selected from Substituents $B^1$ defined below, and the alkanoyl group may optionally be substituted with a phenyl group or with an alkylthio group having 1 or 2 carbon atoms); a 5- or 6-membered heterocyclyl- carbonyl group containing a nitrogen heteroatom (in which the nitrogen heteroatom may optionally be substituted by a substituent selected from Substituents $B^1$ defined below, and the carbonyl group is attached to an atom other than said nitrogen atom); a 5-membered γ-lactamcarbonyl group (in which the nitrogen atom may optionally be substituted by a substituent selected from Substituents $B^1$ defined below, and the carbonyl group is attached to an atom at the 5-position); an α-alkoxyimino-α-heterocyclylacetoxy group, wherein the heterocyclyl moiety is a 5-membered aromatic heterocyclic group which may optionally be substituted by 1 or 2 substituents selected from an amino group and amino groups substituted by 1 or 2 substituents (which may be the same or different) selected from Substituents $B^1$ defined below, and in which the alkoxyimino moiety has 1 or 2 carbon atoms.

The more preferred compounds of the invention in which X represents a group of the formula (III) are those wherein:

$R^1$ represents a methyl or ethyl group;

Z represents an alkanoyl group having 2 or 3 carbon atoms; an alkylsulfonyl group having from 1 to 3 carbon atoms; an aminoalkanoyl group having from 2 to 5 carbon atoms (in which the amino group may be substituted by 1 or 2 substituents selected from Substituents $B^2$ defined below, and the alkanoyl group may optionally be substituted by a methylthio group); and a 5- or 6-membered heterocyclylcarbonyl group containing a nitrogen heteroatom (in which the nitrogen heteroatom may optionally be substituted by a substituent selected from Substituents $B^2$ defined below).

Particularly preferred compounds of the invention in which X represents a group of the formula (III) are those wherein the substituent Z—NH— is present in the para-position on the phenyl ring, and Z represents an alkylsulfonyl group having 2 or 3 carbon atoms; an aminoalkanoyl group having from 2 to 4 carbon atoms (in which the amino group may otionally be substituted by 1 or substituents selected from Substituents $B^2$ defined below); and a 5-membered heterocyclylcarbonyl group containing a nitrogen heteroatom (in which the nitrogen heteroatom may optionally be substituted by a substituent selected from Substituents $B^2$ defined below).

The most preferred compounds of the invention in which X represents a group of the formula (III) are those wherein:

$R^1$ represents an ethyl group;

$R^2$ represents a methyl group;

p is 0;

the substituent Z—NH— is present in the para-position on the phenyl ring; and

Z represents an aminoalkanoyl group having 2 or 3 carbon atoms (in which the amino group may optionally be substituted by a substituent selected from Substituents $B^3$ defined below) or a saturated 5-membered heterocyclylcarbonyl group containing a nitrogen heteroatom (in which the nitrogen heteroatom may optionally be substituted by a substituent selected from Substituents $B^3$ defined below).

Substituents $A^1$

A fluorine atom; a chlorine atom; a bromine atom; a nitro group; a hydroxy group; an alkoxy group having from 1 to 3 carbon atoms; an aralkyloxy group having from 7 to 10 carbon atoms; an amino group; an alkanoylamino group having 1 or 2 carbon atoms; a fluorine-, chlorine- or bromine-substituted alkanoylamino group having 2 or 3 carbon atoms; an alkylsulfonylamino group having from 1 to 3 carbon atoms; an alkoxycarbonylamino group having 2 or 3 carbon atoms; an aminoalkanoylamino group having from 2 to 5 carbon atoms (in which the amino group of the aminoalkanoyl moiety may optionally be substituted by a group which is selected from the Substituents $C^1$ defined below); a 6-membered saturated heterocyclylcarbonylamino group containing one nitrogen atom in the ring (in which the nitrogen atom may optionally be substituted by a group which is selected from Substituents $C^1$ defined below, and the carbonylamino group is substituted at an atom other than said nitrogen ring atom).

Substituents $A^2$

A fluorine atom; a chlorine atom; a bromine atom; a hydroxy group; a methoxy group; an ethoxy group; a benzyloxy group; an amino group; an acetylamino group; a monochloroacetylamino group; a monobromoacetylamino group; a trifluoroacetylamino group; an alkylsulfonylamino group having 1 or 2 carbon atoms; an aminoalkanoylamino group having 2 or 3 carbon atoms (in which the amino group of said aminoalkanoyl moiety may optionally be substituted by a group which is selected from Substituents $C^2$ defined below); a pyrrolidinecarbonylamino group (in which the nitrogen heteroatom may optionally be substituted by a group which is selected from the Substituents $C^2$ defined below, and the carbonylamino group is linked to any atom other than the nitrogen atom).

Substituents $A^3$

A fluorine atom; a chlorine atom; a bromine atom; a hydroxy group; a methoxy group; an ethoxy group; a benzyloxy group; an amino group; an acetylamino group; a monochloroacetylamino group; a monobromoacetylamino group; a trifluoroacetylamino group; an alkylsulfonylamino group having 1 or 2 carbon atoms; an acetylaminoacetylamino group; and an alkoxycarbonylaminoalkanoylamino group having 1 or 2 carbon atoms in its alkyl moiety and 2 or 3 carbon atoms in its alkanoylamino moiety.

Substituents $B^1$

An alkyl group having from 1 to 3 carbon atoms; an alkanoyl group having 2 or 3 carbon atoms; an alkoxycarbonyl group having from 2 to 5 carbon atoms; an arylcarbonyl group having from 7 to 11 carbon atoms; and an alkoxycarbonylaminoalkanoyl group in which the alkoxycarbonyl moiety has from 2 to 5 carbon atoms and the alkanoyl moiety has 2 or 3 carbon atoms.

Substituents $B^2$

An alkyl group having from 1 to 3 carbon atoms; an alkanoyl group having 2 or 3 carbon atoms; an alkoxycarbonyl group having from 2 to 5 carbon atoms; and an arylcarbonyl group having from 7 to 11 carbon atoms.

Substituents $B^3$

An alkyl group having from 1 to 3 carbon atoms; an alkanoyl group having 2 or 3 carbon atoms; and an alkoxycarbonyl group having 2 or 3 carbon atoms.

Substituents $C^1$

An alkyl group having 1 or 2 carbon atoms; a formyl group; an alkanoyl group having 2 or 3 carbon atoms which may optionally be substituted by from 1 to 3 halogen atoms; an alkoxycarbonyl group having 2 or 3 carbon atoms; a benzoyl group; and a benzyloxycarbonyl group.

Substituents $C^2$

A methyl group; an alkanoyl group having 2 or 3 carbon atoms; an alkoxycarbonyl group having 2 or 3 carbon atoms.

The compounds of the present invention may contain several asymmetric carbon atoms in their molecules, and can thus form optical isomers. Although these are all represented herein by a single molecular formula, the present invention includes both the individual, isolated isomers and mixtures, including racemates thereof. Where stereospecific synthesis techniques are employed or optically active compounds are employed as starting materials, individual isomers may be prepared directly; on the other hand, if a mixture of isomers is prepared, the individual isomers may be obtained by conventional resolution techniques. In particular, the compounds of the present invention can exist in the α- or β-configuration with respect to the stereochemistry of the 13-position of the milbemycin skelton. Although all such isomers and mixtures thereof form a part of the present invention, the preferred configuration is the β-configuration.

Milbemycin derivatives having an oximino substituent at the 13-position in accordance with the invention can exist in the form of syn and anti isomers with respect to the nitrogen atom of the oxime group. Where these oxime isomers can separated by column chromatography, a less polar milbemycin derivative is tentatively expressed as isomer A and a more polar one is expressed as isomer B.

Specific examples of compounds of the invention are listed in Tables 1, 2 and 3 below.

The compounds in Table 1 are all compounds having the formula (I), as defined above, wherein X represents a group having the said formula (II).

The compounds in Table 2 are all compounds having the formula (I), as defined above, wherein X represents a group having the said formula (II), and wherein:

(a) for compounds 2-1 to 2-96 inclusive, Y represents the group 4-(A—NH)-phenylin which A has the meaning shown for the said compounds in Table 2;

(b) for compounds 2-97 to 2-106 inclusive, Y represents the group

A—NH—thiazol-4-ylin which A has the meaning shown for the said compounds in Table 2;

and (c) for compounds 2-107 to 2-114 inclusive, Y represents the group

A—NH-phenylin which A has the meaning shown for the said compounds in Table 2 and the prefix numeral for each group A indicates the position of the substituent A—NH— on the phenyl ring.

The compounds in Table 3 are all compounds having the formula (I), as defined above, wherein X represents a group having the said formula (III) and, more preferably, a group having the formula 4-(Z—NH)-$C_6H_4$-(O)$_p$- in which Z and p have the meanings defined above.

In the following tables the abbreviations used have the following significance:

| | | | |
|---|---|---|---|
| Ac: | acetyl | AcNH: | acetylamino |
| BAc: | bromoacetyl | BAcNH: | bromoacetylamino |
| Bn: | benzyl | Bu: | butyl |
| BuO: | butoxy | BzO: | benzyloxy |
| CAc: | chloroacetyl | CAcNH: | chloroacetylamino |
| Et: | ethyl | EtO: | ethoxy |
| Fo: | formyl | Fu: | furyl |
| Hex: | hexyl | Lac: | lactam |
| Me: | methyl | MeO: | methoxy |
| Oxa: | oxazolyl | Pen: | pentyl |
| Ph: | phenyl | PhenO: | phenethyloxy |
| Pip: | piperidyl | Pr: | propyl |
| PrO: | propoxy | Pro: | propionyl |
| ProNH: | propionylamino | Py: | pyridyl |
| Pyr: | pyrrolidinyl | TfAcNH: | trifluoroacetylamino |
| Thd: | thiazolydinyl | Thi: | thienyl |
| Thiz: | thiazolyl | c-: | cycla |
| i: | iso | s: | secondary |
| t: | tertiary | | |

TABLE 1

| Comp. No. | $R^1$ | $R^3$ | Y | $-(CR_2^2)_m-(C=O)_n-$ |
|---|---|---|---|---|
| 1-1 | $CH_3$ | H | Ph | $-CH_2-$ |
| 1-2 | $CH_3$ | $CH_3$ | Ph | $-CH_2-$ |
| 1-3 | $CH_3$ | $CH_3$ | 2-Cl—Ph | $-CH_2-$ |
| 1-4 | $CH_3$ | $CH_3$ | 3-F—Ph | $-CH_2-$ |
| 1-5 | $CH_3$ | $CH_3$ | 3-Cl—Ph | $-CH_2-$ |
| 1-6 | $CH_3$ | $CH_3$ | 3-Fu | $-CH_2-$ |
| 1-7 | $CH_3$ | $CH_3$ | 2-Thi | $-CH_2-$ |
| 1-8 | $CH_3$ | $CH_3$ | 4-(2-$NH_2$—Thiz) | $-CH_2-$ |
| 1-9 | $CH_3$ | $CH_3$ | 4-(2-CAcNH—Thiz) | $-CH_2-$ |
| 1-10 | $C_2H_5$ | H | Ph | $-CH_2-$ |
| 1-11 | $C_2H_5$ | $CH_3$ | Ph | $-CH_2-$ |
| 1-12 | $C_2H_5$ | $CH_3$ | 2-Cl—Ph | $-CH_2-$ |
| 1-13 | $C_2H_5$ | $CH_3$ | 3-F—Ph | $-CH_2-$ |
| 1-14 | $C_2H_5$ | $CH_3$ | 3-Cl—Ph | $-CH_2-$ |
| 1-15 | $C_2H_5$ | $CH_3$ | 3-Fu | $-CH_2-$ |
| 1-16 | $C_2H_5$ | $CH_3$ | 2-Thi | $-CH_2-$ |
| 1-17 | $C_2H_5$ | $CH_3$ | 4-(2-$NH_2$—Thiz) | $-CH_2-$ |
| 1-18 | $C_2H_5$ | $CH_3$ | 4-(2-CAcNH—Thiz) | $-CH_2-$ |
| 1-19 | $i-C_3H_7$ | H | Ph | $-CH_2-$ |
| 1-20 | $i-C_3H_7$ | $CH_3$ | Ph | $-CH_2-$ |
| 1-21 | $i-C_3H_7$ | $CH_3$ | 2-Cl—Ph | $-CH_2-$ |
| 1-22 | $i-C_3H_7$ | $CH_3$ | 3-F—Ph | $-CH_2-$ |
| 1-23 | $i-C_3H_7$ | $CH_3$ | 3-Cl—Ph | $-CH_2-$ |
| 1-24 | $i-C_3H_7$ | $CH_3$ | 3-Fu | $-CH_2-$ |
| 1-25 | $i-C_3H_7$ | $CH_3$ | 2-Thi | $-CH_2-$ |
| 1-26 | $i-C_3H_7$ | $CH_3$ | 4-(2-$NH_2$—Thiz) | $-CH_2-$ |
| 1-27 | $i-C_3H_7$ | $CH_3$ | 4-(2-CAcNH—Thiz) | $-CH_2-$ |
| 1-28 | $s-C_4H_9$ | H | Ph | $-CH_2-$ |
| 1-29 | $s-C_4H_9$ | $CH_3$ | Ph | $-CH_2-$ |
| 1-30 | $s-C_4H_9$ | $CH_3$ | 2-Cl—Ph | $-CH_2-$ |
| 1-31 | $s-C_4H_9$ | $CH_3$ | 3-F—Ph | $-CH_2-$ |
| 1-32 | $s-C_4H_9$ | $CH_3$ | 3-Cl—Ph | $-CH_2-$ |
| 1-33 | $s-C_4H_9$ | $CH_3$ | 3-Fu | $-CH_2-$ |
| 1-34 | $s-C_4H_9$ | $CH_3$ | 2-Thi | $-CH_2-$ |
| 1-35 | $s-C_4H_9$ | $CH_3$ | 4-(2-$NH_2$—Thiz) | $-CH_2-$ |
| 1-36 | $s-C_4H_9$ | $CH_3$ | 4-(2-CAcNH—Thiz) | $-CH_2-$ |
| 1-37 | $CH_3$ | H | Ph | $-C=O-$ |
| 1-38 | $CH_3$ | $CH_3$ | Ph | $-C=O-$ |
| 1-39 | $CH_3$ | $CH_3$ | 2-Cl—Ph | $-C=O-$ |
| 1-40 | $CH_3$ | $CH_3$ | 3-F—Ph | $-C=O-$ |
| 1-41 | $CH_3$ | $CH_3$ | 3-Cl—Ph | $-C=O-$ |
| 1-42 | $CH_3$ | $CH_3$ | 4-Cl—Ph | $-C=O-$ |
| 1-43 | $CH_3$ | $CH_3$ | 4-Br—Ph | $-C=O-$ |
| 1-44 | $CH_3$ | $CH_3$ | 4-$NO_2$—Ph | $-C=O-$ |
| 1-45 | $CH_3$ | $CH_3$ | 4-$NH_2$—Ph | $-C=O-$ |
| 1-46 | $CH_3$ | $CH_3$ | 4-AcNH—Ph | $-C=O-$ |
| 1-47 | $CH_3$ | $CH_3$ | 4-ProNH—Ph | $-C=O-$ |
| 1-48 | $CH_3$ | $CH_3$ | 4-CAcNH—Ph | $-C=O-$ |
| 1-49 | $CH_3$ | $CH_3$ | 4-BrAcNH—Ph | $-C=O-$ |
| 1-50 | $CH_3$ | $CH_3$ | 4-TfAcNH—Ph | $-C=O-$ |
| 1-51 | $CH_3$ | $CH_3$ | 4-FoNH—Ph | $-C=O-$ |
| 1-52 | $CH_3$ | $CH_3$ | 4-OH—Ph | $-C=O-$ |
| 1-53 | $CH_3$ | $CH_3$ | 2-MeO—Ph | $-C=O-$ |
| 1-54 | $CH_3$ | $CH_3$ | 2-EtO—Ph | $-C=O-$ |
| 1-55 | $CH_3$ | $CH_3$ | 4-iPrO—Ph | $-C=O-$ |
| 1-56 | $CH_3$ | $CH_3$ | 4-sBuO—Ph | $-C=O-$ |
| 1-57 | $CH_3$ | $CH_3$ | BzOPh | $-C=O-$ |
| 1-58 | $CH_3$ | $CH_3$ | PhenOPh | $-C=O-$ |
| 1-59 | $CH_3$ | $CH_3$ | 3-Fu | $-C=O-$ |
| 1-60 | $CH_3$ | $CH_3$ | 2-(5-Br—Fu) | $-C=O-$ |
| 1-61 | $CH_3$ | $CH_3$ | 2-Thi | $-C=O-$ |
| 1-62 | $CH_3$ | $CH_3$ | 2-(5-Br—Thi) | $-C=O-$ |
| 1-63 | $CH_3$ | $CH_3$ | 4-Thiz | $-C=O-$ |
| 1-64 | $CH_3$ | $CH_3$ | 4-(2-$NH_2$—Thiz) | $-C=O-$ |
| 1-65 | $CH_3$ | $CH_3$ | 4-(2-CAcNH—Thiz) | $-C=O-$ |
| 1-66 | $CH_3$ | $CH_3$ | 4-(2-BAcNH—Thiz) | $-C=O-$ |
| 1-67 | $CH_3$ | $CH_3$ | 4-(2-FoNH—Thiz) | $-C=O-$ |
| 1-68 | $CH_3$ | $CH_3$ | 2-Py | $-C=O-$ |
| 1-69 | $CH_3$ | $CH_3$ | 2-(5-Cl—Py) | $-C=O-$ |
| 1-70 | $C_2H_5$ | H | Ph | $-C=O-$ |
| 1-71 | $C_2H_5$ | H | 2-Cl—Ph | $-C=O-$ (isomer A) |
| 1-72 | $C_2H_5$ | $CH_3$ | Ph | $-C=O-$ |
| 1-73 | $C_2H_5$ | $CH_3$ | Ph | $-C=O-$ (isomer B) |
| 1-74 | $C_2H_5$ | $CH_3$ | 2-Cl—Ph | $-C=O-$ |
| 1-75 | $C_2H_5$ | $CH_3$ | 3-F—Ph | $-C=O-$ |
| 1-76 | $C_2H_5$ | $CH_3$ | 3-Cl—Ph | $-C=O-$ |
| 1-77 | $C_2H_5$ | $CH_3$ | 4-Cl—Ph | $-C=O-$ (isomer A) |
| 1-78 | $C_2H_5$ | $CH_3$ | 4-Cl—Ph | $-C=O-$ (isomer B) |
| 1-79 | $C_2H_5$ | $C_2H_5$ | 4-Cl—Ph | $-C=O-$ (isomer A) |
| 1-80 | $C_2H_5$ | $C_2H_5$ | 4-Cl—Ph | $-C=O-$ (isomer B) |
| 1-81 | $C_2H_5$ | $CH_3$ | 4-$NO_2$—Ph | $-C=O-$ |
| 1-82 | $C_2H_5$ | $CH_3$ | 4-$NH_2$—Ph | $-C=O-$ |
| 1-83 | $C_2H_5$ | $CH_3$ | 4-AcNH—Ph | $-C=O-$ |
| 1-84 | $C_2H_5$ | $CH_3$ | 4-ProNH—Ph | $-C=O-$ |
| 1-85 | $C_2H_5$ | $CH_3$ | 4-CAcNH—Ph | $-C=O-$ |
| 1-86 | $C_2H_5$ | $CH_3$ | 4-BAcNH—Ph | $-C=O-$ |
| 1-87 | $C_2H_5$ | $CH_3$ | 4-TfAcNH—Ph | $-C=O-$ |
| 1-88 | $C_2H_5$ | $CH_3$ | 4-FoNH—Ph | $-C=O-$ |
| 1-89 | $C_2H_5$ | $CH_3$ | 2-OH—Ph | $-C=O-$ |
| 1-90 | $C_2H_5$ | $CH_3$ | 2-MeO—Ph | $-C=O-$ (isomer A) |
| 1-91 | $C_2H_5$ | $CH_3$ | 2-MeO—Ph | $-C=O-$ (isomer B) |
| 1-92 | $C_2H_5$ | $CH_3$ | 2-EtO—Ph | $-C=O-$ (isomer A) |
| 1-93 | $C_2H_5$ | $CH_3$ | 2-EtO—Ph | $-C=O-$ (isomer B) |
| 1-94 | $C_2H_5$ | $CH_3$ | 4-iPrO—Ph | $-C=O-$ (isomer A) |
| 1-95 | $C_2H_5$ | $CH_3$ | 4-iPrO—Ph | $-C=O-$ (isomer B) |
| 1-96 | $C_2H_5$ | $CH_3$ | 4-sBuO—Ph | $-C=O-$ (isomer A) |
| 1-97 | $C_2H_5$ | $CH_3$ | 4-sBuO—Ph | $-C=O-$ (isomer B) |
| 1-98 | $C_2H_5$ | $CH_3$ | 3-BzOPh | $-C=O-$ |
| 1-99 | $C_2H_5$ | $CH_3$ | 3-PhenOPh | $-C=O-$ |
| 1-100 | $C_2H_5$ | $CH_3$ | 3-Fu | $-C=O-$ |
| 1-101 | $C_2H_5$ | $CH_3$ | 2-(5-Br—Fu) | $-C=O-$ |

TABLE 1-continued

| Comp. No. | $R^1$ | $R^3$ | Y | $-(CR_2^2)_m-(C=O)_n-$ |
|---|---|---|---|---|
| 1-102 | $C_2H_5$ | $CH_3$ | 2-Thi | $-C=O-$ |
| 1-103 | $C_2H_5$ | $CH_3$ | 2-(5-Br—Thi) | $-C=O-$ |
| 1-104 | $C_2H_5$ | $CH_3$ | 4-Ox | $-C=O-$ |
| 1-105 | $C_2H_5$ | $CH_3$ | 4-(2-$NH_2$—Ox) | $-C=O-$ |
| 1-106 | $C_2H_5$ | $CH_3$ | 4-Thiz | $-C=O-$ |
| 1-107 | $C_2H_5$ | $CH_3$ | 4-(2-$NH_2$—Thiz) | $-C=O-$ |
| 1-108 | $C_2H_5$ | $CH_3$ | 4-(2-CAcNH—Thiz) | $-C=O-$ |
| 1-109 | $C_2H_5$ | $CH_3$ | 4-(2-BAcNH—Thiz) | $-C=O-$ |
| 1-110 | $C_2H_5$ | $CH_3$ | 4-(2-FoNH—Thiz) | $-C=O-$ |
| 1-111 | $C_2H_5$ | $CH_3$ | 2-Py | $-C=O-$ |
| 1-112 | $C_2H_5$ | $CH_3$ | 2-(5-Cl—Py) | $-C=O-$ |
| 1-113 | i-$C_3H_7$ | H | Ph | $-C=O-$ |
| 1-114 | i-$C_3H_7$ | $CH_3$ | Ph | $-C=O-$ |
| 1-115 | i-$C_3H_7$ | $CH_3$ | 2-Cl—Ph | $-C=O-$ |
| 1-116 | i-$C_3H_7$ | $CH_3$ | 3-F—Ph | $-C=O-$ |
| 1-117 | i-$C_3H_7$ | $CH_3$ | 3-Cl—Ph | $-C=O-$ |
| 1-118 | i-$C_3H_7$ | $CH_3$ | 4-Cl—Ph | $-C=O-$ |
| 1-119 | i-$C_3H_7$ | $CH_3$ | 4-Cl—Ph | $-C=O-$ |
| 1-120 | i-$C_3H_7$ | $CH_3$ | 4-$NO_2$—Ph | $-C=O-$ |
| 1-121 | i-$C_3H_7$ | $CH_3$ | 4-$NH_2$—Ph | $-C=O-$ |
| 1-122 | i-$C_3H_7$ | $CH_3$ | 4-AcNH—Ph | $-C=O-$ |
| 1-123 | i-$C_3H_7$ | $CH_3$ | 4-ProNH—Ph | $-C=O-$ |
| 1-124 | i-$C_3H_7$ | $CH_3$ | 4-CAcNH—Ph | $-C=O-$ |
| 1-125 | i-$C_3H_7$ | $CH_3$ | 4-BrAcNH—Ph | $-C=O-$ |
| 1-126 | i-$C_3H_7$ | $CH_3$ | 4-TfAcNH—Ph | $-C=O-$ |
| 1-127 | i-$C_3H_7$ | $CH_3$ | 4-FoNH—Ph | $-C=O-$ |
| 1-128 | i-$C_3H_7$ | $CH_3$ | 4-OH—Ph | $-C=O-$ |
| 1-129 | i-$C_3H_7$ | $CH_3$ | 2-MeO—Ph | $-C=O-$ |
| 1-130 | i-$C_3H_7$ | $CH_3$ | 2-EtO—Ph | $-C=O-$ |
| 1-131 | i-$C_3H_7$ | $CH_3$ | 4-iPrO—Ph | $-C=O-$ |
| 1-132 | i-$C_3H_7$ | $CH_3$ | 4-sBuO—Ph | $-C=O-$ |
| 1-133 | i-$C_3H_7$ | $CH_3$ | 3-BzOPh | $-C=O-$ |
| 1-134 | i-$C_3H_7$ | $CH_3$ | 3-PhenOPh | $-C=O-$ |
| 1-135 | i-$C_3H_7$ | $CH_3$ | 3-Fu | $-C=O-$ |
| 1-136 | i-$C_3H_7$ | $CH_3$ | 2-(5-Br—Fu) | $-C=O-$ |
| 1-137 | i-$C_3H_7$ | $CH_3$ | 2-Thi | $-C=O-$ |
| 1-138 | i-$C_3H_7$ | $CH_3$ | 2-(5-Br—Thi) | $-C=O-$ |
| 1-139 | i-$C_3H_7$ | $CH_3$ | 4-Thiz | $-C=O-$ |
| 1-140 | i-$C_3H_7$ | $CH_3$ | 4-(2-$NH_2$—Thiz) | $-C=O-$ |
| 1-141 | i-$C_3H_7$ | $CH_3$ | 4-(2-CAcNH—Thiz) | $-C=O-$ |
| 1-142 | i-$C_3H_7$ | $CH_3$ | 4-(2-BAcNH—Thiz) | $-C=O-$ |
| 1-143 | i-$C_3H_7$ | $CH_3$ | 4-(2-FoNH—Thiz) | $-C=O-$ |
| 1-144 | i-$C_3H_7$ | $CH_3$ | 2-Py | $-C=O-$ |
| 1-145 | i-$C_3H_7$ | $CH_3$ | 2-(5-Cl—Py) | $-C=O-$ |
| 1-146 | s-$C_4H_9$ | H | Ph | $-C=O-$ |
| 1-147 | s-$C_4H_9$ | $CH_3$ | Ph | $-C=O-$ |
| 1-148 | s-$C_4H_9$ | $CH_3$ | 2-Cl—Ph | $-C=O-$ |
| 1-149 | s-$C_4H_9$ | $CH_3$ | 3-F—Ph | $-C=O-$ |
| 1-150 | s-$C_4H_9$ | $CH_3$ | 3-Cl—Ph | $-C=O-$ |
| 1-151 | s-$C_4H_9$ | $CH_3$ | 4-Cl—Ph | $-C=O-$ |
| 1-152 | s-$C_4H_9$ | $CH_3$ | 4-Cl—Ph | $-C=O-$ |
| 1-153 | s-$C_4H_9$ | $CH_3$ | 4-$NO_2$—Ph | $-C=O-$ |
| 1-154 | s-$C_4H_9$ | $CH_3$ | 4-$NH_2$—Ph | $-C=O-$ |
| 1-155 | s-$C_4H_9$ | $CH_3$ | 4-AcNH—Ph | $-C=O-$ |
| 1-156 | s-$C_4H_9$ | $CH_3$ | 4-ProNH—Ph | $-C=O-$ |
| 1-157 | s-$C_4H_9$ | $CH_3$ | 4-CAcNH—Ph | $-C=O-$ |
| 1-158 | s-$C_4H_9$ | $CH_3$ | 4-BrAcNH—Ph | $-C=O-$ |
| 1-159 | s-$C_4H_9$ | $CH_3$ | 4-TfAcNH—Ph | $-C=O-$ |
| 1-160 | s-$C_4H_9$ | $CH_3$ | 4-FoNH—Ph | $-C=O-$ |
| 1-161 | s-$C_4H_9$ | $CH_3$ | 4-OH—Ph | $-C=O-$ |
| 1-162 | s-$C_4H_9$ | $CH_3$ | 2-MeO—Ph | $-C=O-$ |
| 1-163 | s-$C_4H_9$ | $CH_3$ | 2-EtO—Ph | $-C=O-$ |
| 1-164 | s-$C_4H_9$ | $CH_3$ | 4-iPrO—Ph | $-C=O-$ |
| 1-165 | s-$C_4H_9$ | $CH_3$ | 4-sBuO—Ph | $-C=O-$ |
| 1-166 | s-$C_4H_9$ | $CH_3$ | 3-BzOPh | $-C=O-$ |
| 1-167 | s-$C_4H_9$ | $CH_3$ | 3-PhenOPh | $-C=O-$ |
| 1-168 | s-$C_4H_9$ | $CH_3$ | 3-Fu | $-C=O-$ |
| 1-169 | s-$C_4H_9$ | $CH_3$ | 2-(5-Br—Fu) | $-C=O-$ |
| 1-170 | s-$C_4H_9$ | $CH_3$ | 2-Thi | $-C=O-$ |
| 1-171 | s-$C_4H_9$ | $CH_3$ | 2-(5-Br—Thi) | $-C=O-$ |
| 1-172 | s-$C_4H_9$ | $CH_3$ | 4-Thiz | $-C=O-$ |
| 1-173 | s-$C_4H_9$ | $CH_3$ | 4-(2-$NH_2$—Thiz) | $-C=O-$ |
| 1-174 | s-$C_4H_9$ | $CH_3$ | 4-(2-CAcNH—Thiz) | $-C=O-$ |
| 1-175 | s-$C_4H_9$ | $CH_3$ | 4-(2-BAcNH—Thiz) | $-C=O-$ |
| 1-176 | s-$C_4H_9$ | $CH_3$ | 4-(2-FoNH—Thiz) | $-C=O-$ |
| 1-177 | s-$C_4H_9$ | $CH_3$ | 2-Py | $-C=O-$ |
| 1-178 | s-$C_4H_9$ | $CH_3$ | 2-(5-Cl—Py) | $-C=O-$ |
| 1-179 | $CH_3$ | H | Ph | $-CH_2-C=O-$ |
| 1-180 | $CH_3$ | $CH_3$ | Ph | $-CH_2-C=O-$ |
| 1-181 | $CH_3$ | $CH_3$ | 3-Fu | $-CH_2-C=O-$ |
| 1-182 | $CH_3$ | $CH_3$ | 2-Thi | $-CH_2-C=O-$ |
| 1-183 | $CH_3$ | $CH_3$ | 4-(2-$NH_2$—Thiz) | $-CH_2-C=O-$ |
| 1-184 | $CH_3$ | $CH_3$ | 2-Py | $-CH_2-C=O-$ |
| 1-185 | $C_2H_5$ | H | Ph | $-CH_2-C=O-$ |
| 1-186 | $C_2H_5$ | $CH_3$ | Ph | $-CH_2-C=O-$ |
| 1-187 | $C_2H_5$ | $CH_3$ | 3-Fu | $-CH_2-C=O-$ |
| 1-188 | $C_2H_5$ | $CH_3$ | 2-Thi | $-CH_2-C=O-$ |
| 1-189 | $C_2H_5$ | $CH_3$ | 4-(2-$NH_2$—Thiz) | $-CH_2-C=O-$ |
| 1-190 | $C_2H_5$ | $CH_3$ | 2-Py | $-CH_2-C=O-$ |
| 1-191 | i-$C_3H_7$ | H | Ph | $-CH_2-C=O-$ |
| 1-192 | i-$C_3H_7$ | $CH_3$ | Ph | $-CH_2-C=O-$ |
| 1-193 | i-$C_3H_7$ | $CH_3$ | 3-Fu | $-CH_2-C=O-$ |
| 1-194 | i-$C_3H_7$ | $CH_3$ | 2-Thi | $-CH_2-C=O-$ |
| 1-195 | i-$C_3H_7$ | $CH_3$ | 4-(2-$NH_2$—Thiz) | $-CH_2-C=O-$ |
| 1-196 | i-$C_3H_7$ | $CH_3$ | 2-Py | $-CH_2-C=O-$ |
| 1-197 | s-$C_4H_9$ | H | Ph | $-CH_2-C=O-$ |
| 1-198 | s-$C_4H_9$ | $CH_3$ | Ph | $-CH_2-C=O-$ |
| 1-199 | s-$C_4H_9$ | $CH_3$ | 3-Fu | $-CH_2-C=O-$ |
| 1-200 | s-$C_4H_9$ | $CH_3$ | 2-Thi | $-CH_2-C=O-$ |
| 1-201 | s-$C_4H_9$ | $CH_3$ | 4-(2-$NH_2$—Thiz) | $-CH_2-C=O-$ |
| 1-202 | s-$C_4H_9$ | $CH_3$ | 2-Py | $-CH_2-C=O-$ |
| 1-203 | $CH_3$ | $CH_3$ | 4-(2-AcNH—Thiz) | $-C=O-$ |
| 1-204 | $C_2H_5$ | $CH_3$ | 4-(2-AcNH—Thiz) | $-C=O-$ |

TABLE 2

| Comp. No. | $R^1$ | $R^3$ | A | $-(CR_2^2)_m-(C=O)_n-$ |
|---|---|---|---|---|
| 2-1 | Et | Me | MeOCO | $-CH_2-$ |
| 2-2 | Et | Me | EtOCO | $-CH_2-$ |
| 2-3 | Et | Me | $Cl_3CH_2OCO$ | $-CH_2-$ |
| 2-4 | Et | Me | t-BuOCO | $-CH_2-$ |
| 2-5 | Et | Me | $FoNHCH_2CO$ | $-CH_2-$ |
| 2-6 | Me | Me | $AcNHCH_2CO$ | $-CH_2-$ |

TABLE 2-continued

| Comp. No. | $R^1$ | $R^3$ | A | $-(CR_2^2)_m-(C=O)_n-$ |
|---|---|---|---|---|
| 2-7 | Et | Me | AcNHCH$_2$CO | —CH$_2$— |
| 2-8 | Et | Me | ProNHCH$_2$CO | —CH$_2$— |
| 2-9 | Et | Me | BAcNHCH$_2$CO | —CH$_2$— |
| 2-10 | Et | Me | CAcNHCH$_2$CO | —CH$_2$— |
| 2-11 | i-Pr | Me | AcNHCH$_2$CO | —CH$_2$— |
| 2-12 | s-Bu | Me | AcNHCH$_2$CO | —CH$_2$— |
| 2-13 | Me | Me | MeOCONHCH$_2$CO | —CH$_2$— |
| 2-14 | Et | Me | MeOCONHCH$_2$CO | —CH$_2$— |
| 2-15 | Me | Me | MeSO$_2$ | —CH$_2$— |
| 2-16 | Et | Me | MeSO$_2$ | —CH$_2$— |
| 2-17 | i-Pr | Me | MeSO$_2$ | —CH$_2$— |
| 2-18 | s-Bu | Me | MeSO$_2$ | —CH$_2$— |
| 2-19 | Et | Me | EtSO$_2$ | —CH$_2$— |
| 2-20 | Me | H | MeSO$_2$ | —CO— |
| 2-21 | Me | Me | MeSO$_2$ | —CO— |
| 2-22 | Et | Me | MeSO$_2$ | —CO— |
| 2-23 | Et | Et | MeSO$_2$ | —CO— |
| 2-24 | i-Pr | Me | MeSO$_2$ | —CO— |
| 2-25 | s-Bu | Me | MeSO$_2$ | —CO— |
| 2-26 | Me | Me | EtSO$_2$ | —CO— |
| 2-27 | Et | Me | EtSO$_2$ | —CO— |
| 2-28 | Et | Me | PrSO$_2$ | —CO— |
| 2-29 | Et | Me | i-PrSO$_2$ | —CO— |
| 2-30 | Me | Me | MeOCO | —CO— |
| 2-31 | Et | Me | MeOCO | —CO— |
| 2-32 | Et | Me | EtOCO | —CO— |
| 2-33 | Et | Me | Cl$_3$CH$_2$OCO | —CO— |
| 2-34 | Et | Me | i-PrOCO | —CO— |
| 2-35 | Et | Me | t-BuOCO | —CO— |
| 2-36 | Et | Me | H$_2$NCH$_2$CO | —CO— |
| 2-37 | Et | Me | FoNHCH$_2$CO | —CO— |
| 2-38 | Me | Me | AcNHCH$_2$CO | —CO— |
| 2-39 | Et | Me | AcNHCH$_2$CO | —CO— |
| 2-40 | Et | Me | CAcNHCH$_2$CO | —CO— |
| 2-41 | Et | Me | BAcNHCH$_2$CO | —CO— |
| 2-42 | Et | Me | ProNHCH$_2$CO | —CO— |
| 2-43 | Me | Me | MeOCONHCH$_2$CO | —CO— |
| 2-44 | Et | H | MeOCONHCH$_2$CO | —CO— |
| 2-45 | Et | Me | MeOCONHCH$_2$CO | —CO— |
| 2-46 | Et | Et | MeOCONHCH$_2$CO | —CO— |
| 2-47 | Et | Pr | MeOCONHCH$_2$CO | —CO— |
| 2-48 | Et | i-Pr | MeOCONHCH$_2$CO | —CO— |
| 2-49 | i-Pr | Me | MeOCONHCH$_2$CO | —CO— |
| 2-50 | s-Bu | Me | MeOCONHCH$_2$CO | —CO— |
| 2-51 | Et | H | EtOCONHCH$_2$CO | —CO— |
| 2-52 | Et | Me | EtOCONHCH$_2$CO | —CO— |
| 2-53 | Et | Me | Cl$_3$CH$_2$OCONHCH$_2$CO | —CO— |
| 2-54 | Et | Me | PrOCONHCH$_2$CO | —CO— |
| 2-55 | Et | Me | i-PrOCONHCH$_2$CO | —CO— |
| 2-56 | Et | Me | t-BuOCONHCH$_2$CO | —CO— |
| 2-57 | Et | Me | BnOCONHCH$_2$CO | —CO— |
| 2-58 | Et | Me | PhenOCONHCH$_2$CO | —CO— |
| 2-59 | Et | Me | PhCONHCH$_2$CO | —CO— |
| 2-60 | Et | Me | MeOCON(Me)CH$_2$CO | —CO— |
| 2-61 | Et | Me | EtOCON(Me)CH$_2$CO | —CO— |
| 2-62 | Et | Me | MeOCONHCH$_2$CH$_2$CO | —CO— |
| 2-63 | Et | Me | EtOCONHCH$_2$CH$_2$CO | —CO— |
| 2-64 | Me | Me | MeOCONHCH(Me)CO | —CO— |
| 2-65 | Et | Me | MeOCONHCH(Me)CO | —CO— |
| 2-66 | Et | Me | MeOCONHCH(Et)CO | —CO— |
| 2-67 | Me | Me | MeOCONHC(Me)$_2$CO | —CO— |
| 2-68 | Et | Me | MeOCONHC(Me)$_2$CO | —CO— |
| 2-69 | Et | Me | MeOCONHCH(i-Pr)CO | —CO— |
| 2-70 | Et | Me | MeOCONHCH(Bu)CO | —CO— |
| 2-71 | Me | Me | EtOCONHCH(i-Bu)CO | —CO— |
| 2-72 | Et | Me | MeOCONHCH(i-Bu)CO | —CO— |
| 2-73 | Et | Me | MeOCONHCH(t-Bu)CO | —CO— |
| 2-74 | Et | Me | MeOCONHCH(Ph)CO | —CO— |
| 2-75 | Et | Me | MeOCONHCH(Bn)CO | —CO— |
| 2-76 | Et | Me | MeOCONHCH(CH$_2$CH$_2$SMe)CO | —CO— |
| 2-77 | Et | Me | MeOCONHCH(CH$_2$SMe)CO | —CO— |
| 2-78 | Et | Me | MeOCONHCH(CH$_2$SEt)CO | —CO— |
| 2-79 | Et | Me | 1-(MeOCONH)c-Pen-1-CO | —CO— |
| 2-80 | Et | Me | 1-(MeOCONH)c-Hex-1-CO | —CO— |
| 2-81 | Me | Me | 1-(MeOCO)Pyr-2-CO | —CO— |
| 2-82 | Et | Me | 1-(MeOCO)Pyr-2-CO | —CO— |

TABLE 2-continued

| Comp. No. | $R^1$ | $R^3$ | A | $-(CR_2^2)_m-(C=O)_n-$ |
|---|---|---|---|---|
| 2-83 | Et | Me | 1-AcPyr-2-CO | —CO— |
| 2-84 | Et | Me | 1-(MeOCO)Pip-2-CO | —CO— |
| 2-85 | Me | Me | MeSO₂ | —CH₂—CO— |
| 2-86 | Et | Me | MeSO₂ | —CH₂—CO— |
| 2-87 | i-Pr | Me | MeSO₂ | —CH₂—CO— |
| 2-88 | s-Bu | Me | MeSO₂ | —CH₂—CO— |
| 2-89 | Me | Me | AcNHCH₂CO | —CH₂—CO— |
| 2-90 | Et | Me | AcNHCH₂CO | —CH₂—CO— |
| 2-91 | i-Pr | Me | AcNHCH₂CO | —CH₂—CO— |
| 2-92 | s-Bu | Me | AcNHCH₂CO | —CH₂—CO— |
| 2-93 | Me | Me | MeOCONHCH₂CO | —CH₂—CO— |
| 2-94 | Et | Me | MeOCONHCH₂CO | —CH₂—CO— |
| 2-95 | i-Pr | Me | MeOCONHCH₂CO | —CH₂—CO— |
| 2-96 | s-Bu | Me | MeOCONHCH₂CO | —CH₂—CO— |
| 2-97 | Me | Me | 2-MeOCONHCH₂CO | —CO— |
| 2-98 | Et | Me | 2-MeSO₂ | —CO— |
| 2-99 | Et | Me | 2-MeOCO | —CO— |
| 2-100 | Et | Me | 2-EtOCO | —CO— |
| 2-101 | Et | Me | 2-CCl₃CH₂OCO | —CO— |
| 2-102 | Et | Me | 2-AcNHCH₂CO | —CO— |
| 2-103 | Et | Me | 2-MeOCONHCH₂CO | —CO— |
| 2-104 | Et | Me | 2-EtOCONHCH₂CO | —CO— |
| 2-105 | Et | Me | 2-i-PrOCO | —CO— |
| 2-106 | Et | Me | 2-[2-(1-MeOCOPyr)CO] | —CO— |
| 2-107 | Me | Me | 2-MeOCONHCH₂CO | —CO— |
| 2-108 | Me | Me | 3-MeOCONHCH₂CO | —CO— |
| 2-109 | Et | Me | 2-MeOCONHCH₂CO | —CO— |
| 2-110 | Et | Me | 3-MeOCONHCH₂CO | —CO— |
| 2-111 | Et | Me | 2-AcNHCH₂CO | —CO— |
| 2-112 | Et | Me | 3-AcNHCH₂CO | —CO— |
| 2-113 | Et | Me | 2-MeSO₂ | —CO— |
| 2-114 | Et | Me | 3-MeSO₂ | —CO— |

TABLE 3

| Comp. No. | $R^1$ | $R^2$ | p | Z |
|---|---|---|---|---|
| 3-1 | Et | Me | 1 | Ac |
| 3-2 | Me | Me | 0 | Ac |
| 3-3 | Et | Me | 0 | Ac |
| 3-4 | Et | Et | 0 | Ac |
| 3-5 | Et | Pr | 1 | Ac |
| 3-6 | i-Pr | Me | 0 | Ac |
| 3-7 | s-Bu | Me | 0 | Ac |
| 3-8 | Me | Me | 0 | EtCO |
| 3-9 | Et | Me | 0 | EtCO |
| 3-10 | Me | Me | 0 | MeSO₂ |
| 3-11 | Et | Me | 1 | MeSO₂ |
| 3-12 | Et | Et | 0 | MeSO₂ |
| 3-13 | i-Pr | Me | 0 | MeSO₂ |
| 3-14 | s-Bu | Me | 0 | MeSO₂ |
| 3-15 | Et | Me | 0 | EtSO₂ |
| 3-16 | Et | Me | 1 | PrSO₂ |
| 3-17 | Et | Me | 0 | i-PrSO₂ |
| 3-18 | Me | Me | 1 | Ac |
| 3-19 | Et | Me | 1 | EtOCO |
| 3-20 | Et | Me | 0 | MeOCO |
| 3-21 | Et | Me | 0 | EtOCO |
| 3-22 | Et | Me | 1 | PrOCO |
| 3-23 | Et | Me | 0 | i-PrOCO |
| 3-24 | Me | Me | 1 | H₂NCH₂CO |
| 3-25 | Et | Me | 0 | H₂NCH₂CO |
| 3-26 | Me | Me | 0 | MeOCONHCH₂CO |
| 3-27 | Et | Me | 0 | MeOCONHCH₂CO |
| 3-28 | Et | Et | 0 | MeOCONHCH₂CO |
| 3-29 | Et | Me | 1 | MeOCONHCH₂CO |
| 3-30 | i-Pr | Me | 0 | MeOCONHCH₂CO |
| 3-31 | s-Bu | Me | 0 | MeOCONHCH₂CO |
| 3-32 | Et | Me | 0 | Cl₃CCH₂OCONHCH₂CO |
| 3-33 | Et | Me | 0 | t-BuOCONHCH₂CO |
| 3-34 | Et | Me | 0 | BnOCONHCH₂CO |
| 3-35 | Et | Me | 1 | AcNHCH₂CO |
| 3-36 | Et | Me | 0 | PhCONHCH₂CO |
| 3-37 | Et | Me | 0 | MeOCON(Me)CH₂CO |
| 3-38 | Et | Me | 0 | EtOCON(Me)CH₂CO |
| 3-39 | Et | Me | 0 | i-PrOCONHCH₂CO |
| 3-40 | Et | Me | 0 | MeOCONHCH(Ph)CO |
| 3-41 | Et | Me | 0 | EtOCONHCH₂CONHCH₂CO |
| 3-42 | Et | Me | 0 | 4-(MeOCONH)PhCONHCH₂CO |
| 3-43 | Et | Me | 0 | MeOCONHCH₂CONHCH₂CO |
| 3-44 | Et | Me | 1 | H₂NCH₂ CH₂CO |
| 3-45 | Me | Me | 1 | MeOCONHCH₂CH₂CO |
| 3-46 | Et | Me | 0 | MeOCONHCH₂CH₂CO |
| 3-47 | Et | Me | 0 | MeOCONHCH(Me)CO |
| 3-48 | Et | Me | 0 | AcNHCH₂CO |
| 3-49 | Et | Me | 0 | EtOCONHCH₂CH₂CO |
| 3-50 | Et | Me | 0 | ClCH₂CONHCH₂CO |
| 3-51 | Et | Me | 1 | EtOCONHCH₂CO |
| 3-52 | Et | Pr | 0 | MeOCONHCH₂CO |
| 3-53 | Et | Me | 0 | MeOCONHCH(Bn)CO |
| 3-54 | Et | Me | 0 | MeOCONHCH(Et)CO |
| 3-55 | Me | Me | 1 | MeOCONHCH(Et)CO |
| 3-56 | Et | Me | 0 | MeOCONHC(Me)₂CO |
| 3-57 | Me | Et | 0 | MeOCONHC(Me)₂CO |
| 3-58 | Et | Me | 0 | MeOCONHCH(CH₂CH₂SMe)CO |
| 3-59 | Et | Me | 1 | MeOCONHCH(CH₂SMe)CO |
| 3-60 | Me | Me | 0 | MeOCONHCH(CH₂SEt)CO |
| 3-61 | Et | Me | 0 | MeOCONHCH(i-Pr)CO |
| 3-62 | Et | Me | 1 | EtOCONHCH(i-Pr)CO |
| 3-63 | Me | Me | 0 | EtOCONHCH(i-Bu)CO |
| 3-64 | Et | Me | 0 | MeOCONHCH(i-Bu)CO |
| 3-65 | Et | Me | 0 | MeOCONHCH(t-Bu)CO |
| 3-66 | Et | Me | 1 | 1-(MeOCONH)c-Hex-1-CO |
| 3-67 | Me | Me | 0 | 1-(MeOCONH)c-Pne-1-CO |
| 3-68 | Et | Me | 0 | 1-(MeOCONH)c-Hex-1-CO |
| 3-69 | Et | Me | 0 | 1-(MeOCO)Pyr-2-CO |
| 3-70 | Me | Me | 0 | 1-(MeOCO)Pyr-2-CO |

TABLE 3-continued

| Comp. No. | R¹ | R² | p | Z |
|---|---|---|---|---|
| 3-71 | Et | Me | 0 | 1-(MeOCO)Pip-2-CO |
| 3-72 | Et | Me | 0 | 1-(MeOCO)Pip-4-CO |
| 3-73 | Et | Me | 0 | 3-(MeOCO)Thd-4-CO |
| 3-74 | Me | Me | 0 | 3-(EtOCO)Thd-4-CO |
| 3-75 | Et | Me | 0 | —Lac-6-CO |
| 3-76 | Et | Me | 0 | —Lac-5-CO |
| 3-77 | Et | Me | 0 | 2-(ClCH$_2$CONH)Thiz-4-C(=N—OMe)CO |
| 3-78 | Et | Me | 0 | 2-(MeOCONH)Thiz-4-C(=N—OMe)CO |
| 3-79 | Me | Me | 0 | 2-(MeOCONH)Thiz-4-C(=N—OMe)CO |
| 3-80 | Et | Me | 0 | 2-(NH$_2$)Thiz-4-C(=N—OMe)CO |
| 3-81 | Et | Me | 0 | 2-(EtOCONH)Thiz-4-C(=N—OMe)CO |
| 3-82 | Et | Me | 1 | MeOCON(Me)CH$_2$CO |
| 3-83 | Et | Me | 1 | 1-(MeOCO)Pyr-2-CO |
| 3-84 | Et | Me | 1 | Thi-2-C(=N—OMe)CO |

The preferred compounds of Table 1 are Compound No. 1-11, 1-12, 1-38, 1 72, 1-73, 1-74, 1-75, 1-77, 1-78, 1-79, 1-80, 1-81, 1-89, 1-90, 1-91, 1-92, 1-93, 1-98, 1-100, 1-102, 1-107, 1-111, 1-114, 1-147 and 1-186. The more preferred compounds are Compound No. 1-38, 1-72, 1-73, 1-77, 1-78, 1-79, 1-80, 1-89, 1-92, 1-93 and 1-98. The particularly preferred compounds are Compound No. 1-72 and 1-73.

The preferred compounds of Table 2 are Compound No. 2-7, 2-16, 2-22, 2-39, 2-43, 2-45, 2-60, 2-61, 2-62 and 2-65. The more preferred compounds are Compound No. 2-7, 2-22, 2-39, 2-43 and 2-45.

The preferred compounds of Table 3 are Compound No. 3-1, 3-11, 3-19, 3-26, 3-27, 3-33, 3-34, 3-36, 3-37, 3-38, 3-39, 3-40, 3-43, 3-46, 3-47, 3-48, 3-49, 3-56, 3-58, 3-61, 3-64, 3-65, 3-68, 3-69, 3-70, 3-71, 3-72, 3-76, 3-77 and 3-78. The more preferred compounds are Compound No. 3-11, 3-26, 3-27, 3-36, 3-37, 3-38, 3-39, 3-47, 3-48, 3-56, 3-68, 3-69 and 3-71. The particularly preferred compounds are Compound No. 3-26, 3-27, 3-36, 3-37, 3-47, 3-56 and 3-69.

In accordance with the invention, the compounds of formula (I) can be prepared by a process comprising the following steps:

(a) reacting a compound of formula (IV)

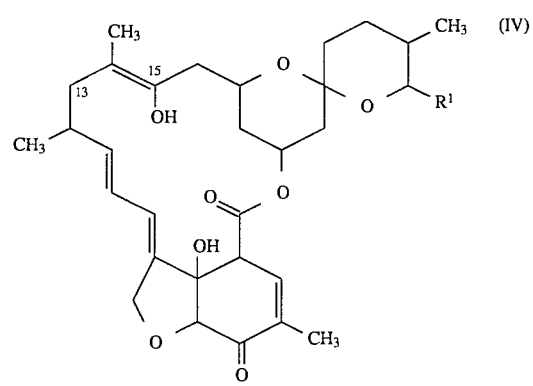

[wherein R¹ has the same meaning as defined for formula (I)]

with a compound of formula (V)

$$B—(CR^2{}_2)_m—(C=O)_n—OH \qquad (V)$$

[wherein R², m and n have the same meanings as defined for formula (I), and B is a group of formula (II) (as defined above) or a group of formula (VI)

wherein p has the same meaning as defined for formula (I)]

to give a compound of formula (VII)

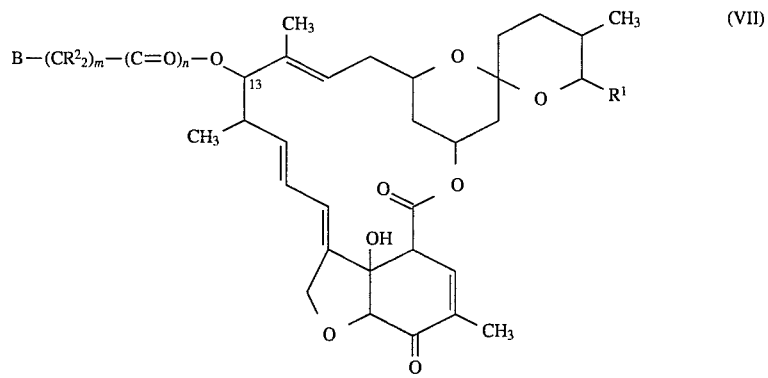

(b) reducing said compound of formula (VII) to give a compound of formula (VIII)

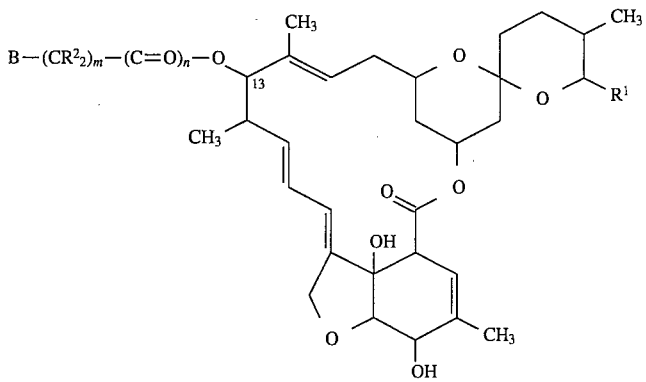

and optionally
either
(c¹) when group B in the compound of formula (VIII) is a group of said formula (II) [in which Y represents a nitro-substituted aryl group having having from 6 to 10 carbon atoms or a nitro-substituted heterocyclyl group] or a group of formula (VI), reducing said compound of formula (VIII) to give a compound of formula (IX)

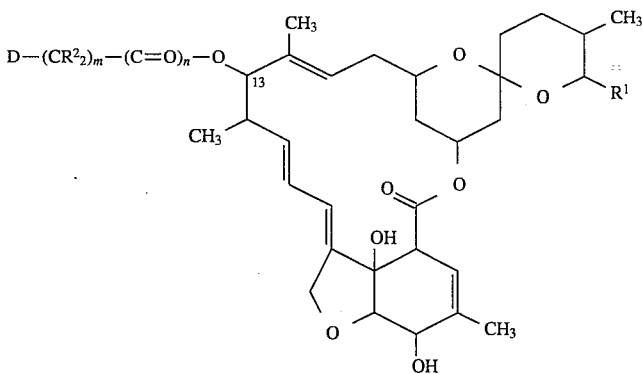

[wherein $R^1$, $R^2$, m and n have the meanings defined for formula (I), and D represents a group of formula (II) (as defined above, wherein Y represents an amino-substituted aryl group having from 6 to 10 carbon atoms or an amino-substituted heterocyclyl group), or a group of formula (X)

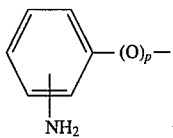

in which p has the meaning defined for formula (I)];
or
(c²) when group B in the compound of formula (VIII) is a group of said formula (II) [in which Y represents an aryl group having from 6 to 10 carbon atoms or a heterocyclyl group, said aryl or heterocyclyl group having at least one alkanoylamino substituent having from 1 to 4 carbon atoms, haloalkanoylamino substituent having from 2 to 4 carbon atoms, alkoxycarbonylamino substituent having from 2 to 5 carbon atoms or haloalkoxycarbonylamino substituent having from 3 to 5 carbon atoms], deacylating said compound of formula (VIII) to give a compound of said formula (IX) wherein Y represents an amino-substituted aryl group having from 6 to 10 carbon atoms or an amino-substituted heterocyclyl group;

and further optionally
(d) reacting said compound of formula (IX) with a compound of formula (XI)

E—OH    (XI)

[wherein E represents an alkanoyl group having from 1 to 4 carbon atoms, a haloalkanoyl group having from 2 to 4 carbon atoms, an alkylsulfonyl group having from 1 to 3 carbon atoms, an alkoxycarbonyl group having from 2 to 5 carbon atoms, a haloalkoxy- carbonyl group having from 3 to 5 carbon atoms, an aminoalkanoyl group having from 2 to 7 carbon atoms (in which the amino group may optionally be substituted by 1 or 2 substituents, which may be the same or different, selected from Substituents C as defined above, and in which the alkanoyl moiety of said aminoalkanoyl group may optionally be substituted by a phenyl group or by an alkylthio group having from 1 to 3 carbon atoms), a saturated 5- or 6-membered heterocyclylcarbonyl group containing nitrogen as a ring atom (in which said nitrogen ring atom may optionally be substituted by a substituent selected from Substituents C as defined above, and in which the carbonyl group is attached to an atom other than the ring nitrogen atom), or a group of formula Z as defined for formula (I)], or a reactive derivative thereof, to give a compound of formula (XII)

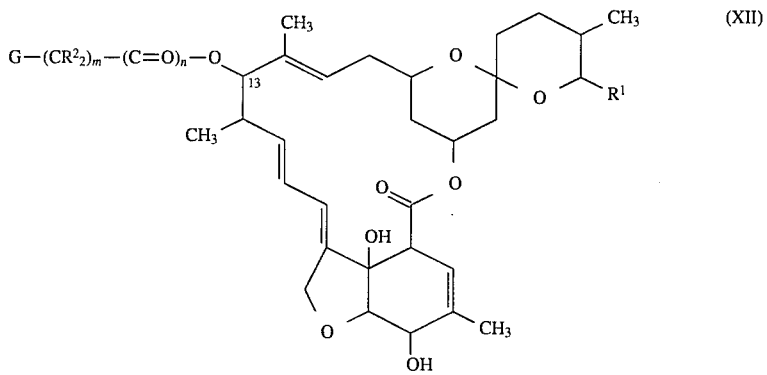

[wherein:

$R^1$, $R^2$, m and n have the same meanings as defined for formula (I); and

G represents a group of formula (III) as defined above; or G represents a group of formula (II) as defined above in which Y represents an aryl group having from 6 to 10 carbon atoms or a heterocyclyl group, and in which said aryl group or said heterocyclyl group has at least one substituent of formula (XIII)

$E^1$—NH— (XIII)

wherein $E^1$ represents the same groups as defined for group E above with the exception of group Z].

In more detail, the compounds of formula (I) of the present invention wherein X represents a group of formula (II), as defined above, may be prepared as illustrated by the following Reaction Scheme A:

REACTION SCHEME A

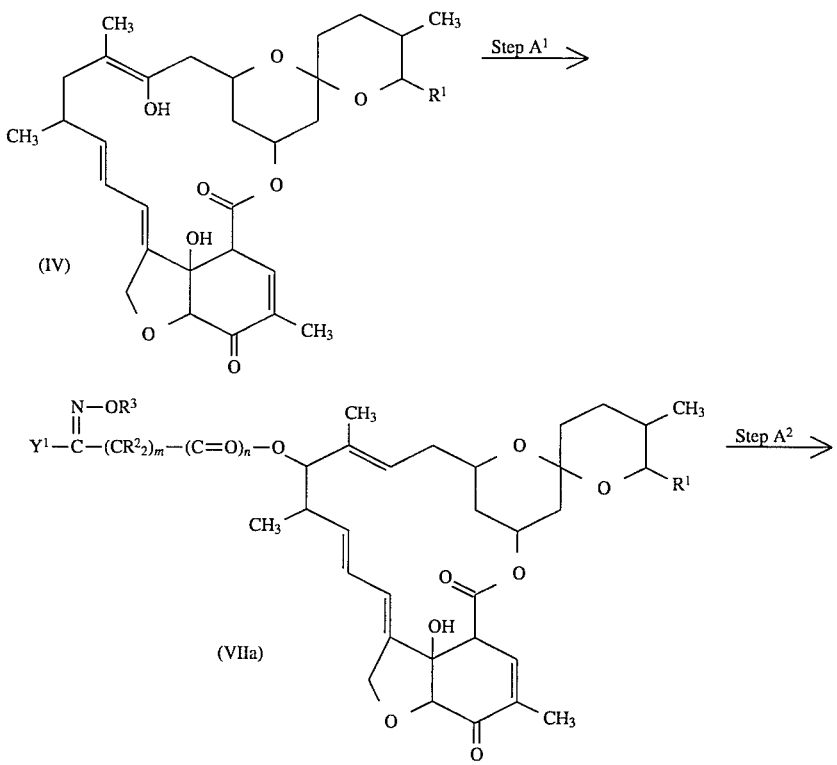

-continued
REACTION SCHEME A

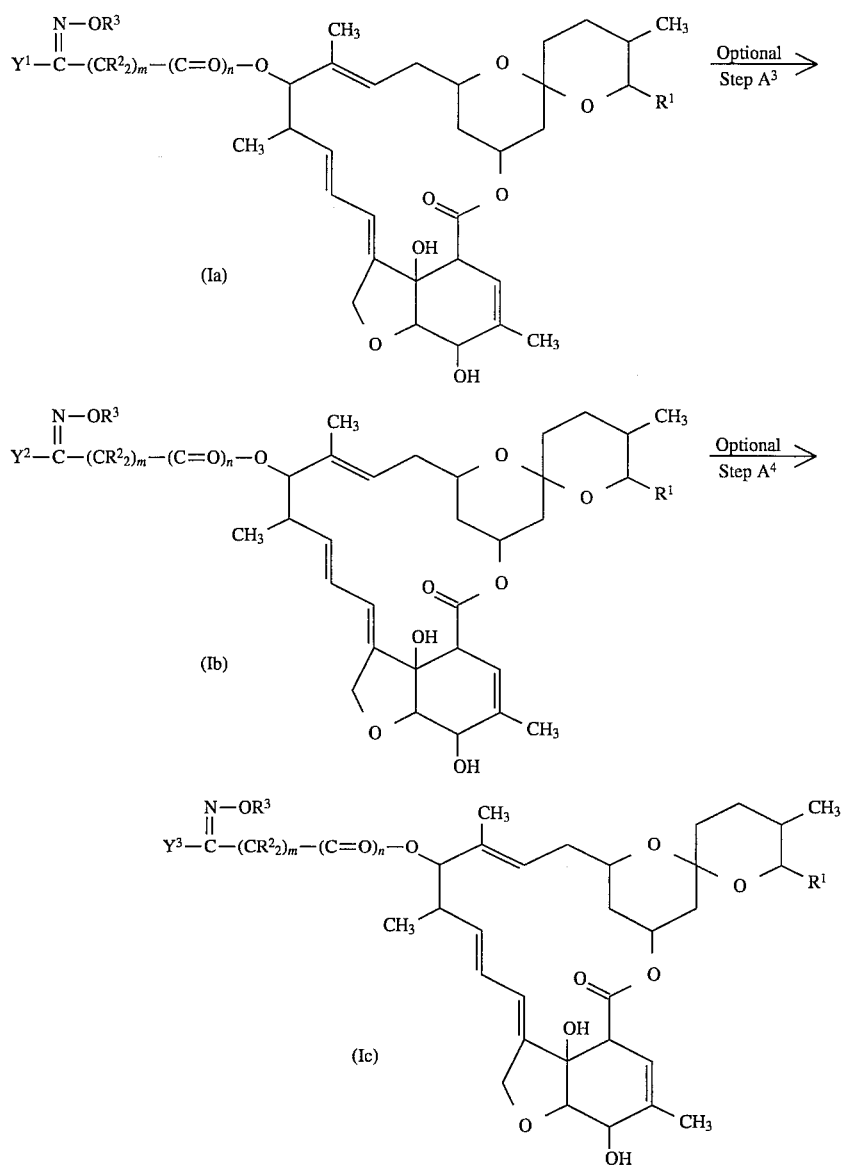

In the above formulae $R^1$, $R^2$, $R^3$, m and n are as defined above; $Y^1$ represents any of the moieties represented by Y as defined above except that any amino-substituted aryl or amino-substituted heterocyclyl moiety is replaced by the corresponding nitro-substituted aryl or nitro-substituted heterocyclyl moiety; $Y^2$ represents an amino-substituted aryl or amino-substituted heterocyclyl moiety as defined above for group Y; and $Y^3$ represents an aryl or heterocyclyl moeity as defined above for group Y wherein said aryl or heterocyclyl moiety is substituted by a group $E^1$—NH (XIII) as defined above.

The 15-hydroxymilbemycin derivative of formula (IV), which is used as a starting material in Step $A^1$ of Reaction Scheme A, can be prepared by the procedure described in European Patent Publication 147,852.

The other starting material in Step $A^1$ of Reaction Scheme A is represented by formula (Va):

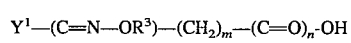

(wherein $R^3$, $Y^1$, m and n are as defined above).

Where m is 0 and n is 1, α-alkoxyiminophenylacetic acids can be prepared using a commercially available ethyl phenylglyoxylate as a starting material, by the procedure described in U.S. Pat. No. 4,024,133. α-alkoxyimino-2-furylacetic acids can be prepared, using commercially available 2-furylcarboxylic acids as a starting material, by the procedure described in GB Patent Publication 1,557,423. α-Alkoxyimino-2-thienylacetic acids can be prepared, using commercially available 2-thienylglyoxylic acid as a starting material, by the procedure described in U.S. Pat. No. 4,024,133. α-Alkoxyimino-(2-amino-4-thiazolyl)acetic acid and its derivatives can be prepared, using commercially available 2-amino-4-thiazolylglyoxylic acid as a starting material, by the procedure described in U.S. Pat. No. 4,024,133.

α-Alkoxyimino(substituted phenyl)acetic acids can be prepared by using 2-(substituted phenyl)-1,2-ethanediol (which is described in J. Med. Chem., 24, 1360(1981) as a starting material, using the procedure described in Chem. Lett., 1350(1985) to produce t-butyldimethylsilyl-2-oxo- (substituted phenethyl)ether, which is then reacted with O-alkoxyhydroxylamine by conventional means to produce 2-alkoxyimino-2-(substituted phenyl)ethanol, which is then oxidised by conventional means to give the desired α-alkoxyimino(substituted phenyl)acetic acid. For example, 2-alkoxyimino-2-(4-nitrophenyl)acetic acid can be prepared by the procedure described in J. Med. Chem., 24, 1360(1981). The procedure consists of converting the starting material, 2-(4-nitrophenyl)-1,2-ethanediol, to t-butyldimethylsilyl-2-oxo-2-(4-nitrophenethyl) ether [this reaction is described in Chem. Lett., 1359(1985)], reacting said ether with O-alkoxyhydroxylamine to produce 2-alkoxyimino-2-(4-nitrophenyl)ethanol, and then oxidizing by conventional means.

2-Alkoxyimino-2-(4-nitrophenyl)acetic acid can also be prepared by using an alternative procedure in which ethyl 4-nitrophenyl glyoxylate [described in Synthesis, 850(1990)], is reacted with O-alkoxyhydroxylamine, followed by hydrolysis of the ester thus obtained.

2-Hydroxyimino-2-(4-nitrophenyl)acetic acid can be prepared by the procedure described above using hydroxylamine in place of O-alkoxyhydroxylamine.

Where m is 1 and n is 0, 2-alkoxyimino-2-(substituted or unsubstituted phenyl)ethanol derivatives, 2-alkoxyimino-2-(2-furyl)ethanol derivatives, 2-alkoxyimino-2-(2-thienyl)ethanol derivatives and 2-alkoxyimino-2-(2-amino-4-thiazolyl)ethanol derivatives can be prepared as described above, when such compounds are intermediates in the α-alkoxyiminoacetic acid derivative synthesis.

Where m is 1 and n is 1, 3-alkoxyimino-3-(substituted or unsubstituted phenyl)propionic acid derivatives can be prepared using the procedure described above for the synthesis of α-alkoxyiminophenylacetic acid, using as a starting material commercially available ethyl benzoylacetate or ethyl (substituted benzoyl)acetate, which is prepared by conventional methods.

3-Alkoxyimino-3-(4-nitrophenyl)propionic acid can be prepared using as a starting material ethyl (4-nitrobenzoyl)acetate, prepared by a known method, in a similar procedure as that described above for the synthesis of 2-alkoxyimino-2-(4-nitrophenyl)acetic acid. 3-Hydroxyimino-3-(4-nitrophenyl)propionic acid can be prepared from the corresponding propionic acid derivative in a similar manner to that described above.

3-Alkoxyimino-3-(3-furyl)propionic acid derivatives, 3-alkoxyimino-3-(2-thienyl)propionic acid derivatives and 3-alkoxyimino-3-(2-amino-4-thiazolyl)propionic acid derivatives can be prepared by the procedure described above for the production of 3-alkoxyimino-3-(substituted phenyl)propionic acid derivatives.

Step $A^1$ of Reaction Scheme A involves the preparation of a compound of general formula (VIIa) by reacting a compound of general formula (IV) with a carboxylic acid or alcohol of general formula (Va) in the presence of a strong organic acid, such as sulphuric, hydrochloric, methanesulfonic, trifluoromethanesulfonic, benzenesulfonic, 4-chlorobenzenesulfonic or trifluoroacetic acid, and preferably trifluoromethanesulfonic acid.

The amount of trifluoromethanesulfonic or other strong acid used can vary considerably, depending upon the reactivity of the carboxylic acid or alcohol (Va) to be used, but it is not more than 1 equivalent, and is generally a catalytic amount.

The reaction can sometimes be accelerated by adding an inorganic compound to the reaction system. Examples of such inorganic compounds include: metal salts such as copper trifluoromethanesulfonate, copper iodide, zinc iodide, cobalt iodide or nickel iodide, celite, silica gel, alumina or the like; preferably copper salts such as copper trifluoromethanesulfonate or copper iodide; and most preferably copper iodide.

There is no particular limitation upon the nature of the reaction solvent used, provided that it has no adverse effect upon the reaction and can dissolve the starting material, at least to some extent. The carboxylic acid or alcohol compound of general formula (Va) itself can sometimes serve as a solvent. Examples of preferred solvents include: aromatic hydrocarbons such as benzene, toluene or xylene; halogenated hydrocarbons such as dichloromethane, 1,2-dichloroethane or chloroform; esters such as ethyl acetate or propyl acetate; ethers such as diethyl ether, tetrahydrofuran, dioxane or dimethoxyethane; amides such as dimethylformamide, dimethylacetamide or hexamethylphosphoric triamide; sulfoxides such as dimethylsulfoxide; and nitriles such as acetonitrile.

The reaction can be performed over a wide range of temperatures, and the precise temperature is not critical to the present invention, but it is conveniently carried out at a temperature of −10° C. to 100° C., preferably 0° C. to 50° C.

The time required for the reaction varies, depending on many factors, notably the reaction temperature and the nature of the reagents and of the solvent, but a reaction time of from 5 minutes to 6 hours, particularly from 10 minutes to 2 hours, is usually sufficient under suit-able reaction conditions.

Step $A^2$ of Reaction Scheme A involves the preparation of the compound of general formula (Ia) by reacting the compound of general formula (VIIa) with a reducing agent to reduce the carbonyl group at the 5-position to a hydroxyl group.

There is no particular limitation upon the reducing agent used, provided that it is capable of reducing the carbonyl group at the 5-position and provided that other functional groups of the compound of formula (VIIa) are not affected when the carbonyl group is reduced. Examples of such reducing agents include those capable of generating a hydride anion, such as sodium borohydride or diborane, preferably sodium borohydride.

There is no particular limitation upon the nature of the reaction solvent used, provided that it has no adverse effect upon the reaction. Where the reducing agent used is sodium borohydride, examples of particularly preferred solvents include lower alcohols such as methanol, ethanol or propanol.

Although the reaction can be performed over a wide range of temperatures, and the temperature is not critical to the present invention, it is conveniently carried out at a temperature of from 0° C. to 50° C. The time required for the reaction can also vary widely, and is not critical to the present invention. However, a period of from 5 minutes to 2 hours is usually sufficient under suitable reaction conditions.

Optional Step $A^3$ of Reaction Scheme A involves the preparation of a compound of general formula (Ib), wherein $Y^2$ represents an amino-substituted aryl or heterocyclyl moiety as defined for Y above. This can be achieved by two alternative processes. The first of these processes involves reducing the nitro group of a compound of general formula (Ia) wherein $Y^1$ represents a nitro-substituted aryl or heterocyclyl moiety.

Reduction of the nitro group of the compound of formula (Ia) can be carried out by any conventional means, provided that said reduction means does not have an effect on any of the other functional groups of the compound of general formula (Ia). One example of such a technique is catalytic reduction using a noble metal catalyst. Examples of preferred catalysts to be used in the reaction include palladium on charcoal, palladium on barium sulfate and platinum oxide.

The reaction is normally and preferably carried out in the presence of a solvent. There is no particular restriction on the nature of the solvent used, provided that it has no adverse effect on the reaction or on the reagents involved and that it can dissolve the reagents, at least to some extent. Examples of suitable solvents to be used in the reaction include: alcohols such as methanol or ethanol; ethers such as tetrahydrofuran or dioxane; and esters such as ethyl acetate.

The reaction can take place over a wide range of temperatures, and the precise reaction temperature is not critical to the present invention. The reaction is conveniently carried out at a temperature of from 10° C. to 80° C. The time required for the reaction can also vary widely, depending on many factors, notably the reaction temperature and the nature of the reagents and solvent used. Typically, a reaction period from 10 minutes to 5 hours is sufficient, under suitable conditions.

Another preferred method for reduction of the nitro group is reaction of compound (Ia) with zinc powder in the presence of acetic acid. The reaction can take place at a wide range of temperatures, and the precise temperature is not critical to the present invention. However, the reaction is conveniently conducted at a temperature of from 0° C. to room temperature. The time required for the reaction can also vary widely, depending on many factors, notably the reaction temperature and the nature of the reagents and solvent used. A reaction period of from 30 minutes to 12 hours is usually sufficient, under suitable conditions.

The second of the alternative processes for Optional Step $A^3$ of Reaction Scheme A involves deacylation of a compound of general formula (Ia) wherein $Y^1$ represents an aryl or heterocyclyl group substituted by at least one alkanoylamino substituent having from 1 to 4 carbon atoms, haloalkanoylamino substituent having from 2 to 4 carbon atoms, alkoxycarbonylamino substituent having from 2 to 5 carbon atoms or haloalkoxycarbonylamino substituent having from 3 to 5 carbon atoms.

Suitable alkanoylamino substituents include formylamino and acetylamino groups. Suitable haloalkanoylamino substituents include monochloroacetylamino and monobromoacetylamino groups. Suitable alkoxycarbonylamino substituents include a t-butoxycarbonylamino group, and suitable haloalkoxycarbonylamino substituents include a trichloroethoxycarbonylamino group.

Deacylation of the alkanoylamino, haloalkanoylamino, alkoxycarbonylamino or haloalkoxycarbonylamino moiety of the compound of formula (Ia) can be carried out by any conventional means, provided that said deacylation does not have an effect on any of the other functional groups of the compound of general formula (Ia).

Deacylation of the t-butoxycarbonylamino group can, for example, be performed by reaction of the compound of formula (Ia) with hydrochloric acid in dioxane. The reaction can take place over a wide range Of temperatures, and the precise reaction temperature is not critical to the present invention. However, the reaction can be conveniently carried out at room temperature. The time required for the reaction can also vary widely, depending on many factors, notably the reaction temperature and the nature of the reagents and solvent used. Typically, a reaction period of from 1 to 3 hours is sufficient, under suitable conditions.

Deacylation of the formylamino group can, for example, be performed by reaction of the compound of formula (Ia) with hydrochloric acid in methanol. The reaction can take place over a wide range of temperatures, and the precise reaction temperature is not critical to the present invention. However, the reaction can be conveniently carried out at a temperature of approximately 10° C. The time required for the reaction can also vary widely, depending on many factors, notably the reaction temperature and the nature of the reagents and solvent used. Typically, a reaction period of around 1 hour is sufficient, under suitable conditions.

Deacylation of the trichloroethoxycarbonylamino group can, for example, be performed by reaction of the compound of formula (Ia) with cadmium powder in the presence of dimethylformamide. Again, the reaction can take place over a wide range of temperatures, and the precise reaction temperature is not critical to the present invention. However, the reaction can be conveniently carried out at room temperature. The time required for the reaction can also vary widely, and is not critical to the present invention, and depends on many factors, notably the reaction temperature and the nature of the reagents and solvent used. However, a reaction period of from 1 to 3 hours is usually sufficient, under suitable conditions.

Another example for a suitable method for deacylation of the trichloroethoxycarbonylamino group is treatment of the compound of formula (Ia) with zinc and acetic acid. The reaction can take place over a wide range of temperatures, and the precise reaction temperature is not critical to the present invention. However, the reaction can conveniently be performed at room temperature. The time required for the reaction can vary widely, depending on many factors, notably the reaction temperature and the nature of the reagents and solvent used, and is not critical to the present invention. However, a reaction period of from 30 minutes to 1 hour is usually sufficient, under suitable conditions.

Deacylation of the monochloroacetylamino or monobromoacetylamino group can, for example, be performed by treatment of the compound of formula (Ia) with thiourea in dimethylformamide. The reaction can take place over a wide range of temperatures, and the precise reaction temperature is not critical to the present invention. However, the reaction can be conveniently carried out at a temperature of from room temperature to 50° C. The time required for the reaction can also vary widely, depending on many factors, notably the reaction temperature and the nature of the reagents and solvent used. A reaction period of from 1 to 3 hours is usually sufficient, under suitable conditions.

Optional Step $A^4$ of Reaction Scheme A involves the preparation of a compound of general formula (Ic) by reacting an amino group of a compound of general formula (Ib) with an acid of a formula $E^1$—OH (wherein $E^1$ is as defined above) or its reactive derivative.

Suitable reactive derivatives of the acid of formula $E^1$—OH include those used in conventional condensation reactions such as, for example, an acid halide (usually an acid chloride or acid bromide), an acid anhydride, a mixed acid anhydride, an activated ester or an activated amide.

Where an acid represented by a formula $E^1$—OH is used, the reaction is carried out in the presence of a dehydrating agent such as, for example, dicyclohexylcarbodiimide (DCC), 2-chloro-1-methylpyridinium iodide, p-toluenesulfonic acid or sulfuric acid, preferably 2-chloro-1-methylpyridinium iodide. The amount of the reagent used is not critical to the invention, but is normally in the range of 1 to 5 equivalents, preferably 1 to 2 equivalents per mol of the acid of a formula $E^1$—OH.

There is no particular limitation upon the nature of the reaction solvent used, provided that it has no adverse effect upon the reaction and can dissolve the starting material to some extent. Examples of preferred solvents include: hydrocarbons such as hexane, petroleum ether, benzene or toluene; halogenated hydrocarbons such as chloroform, dichloromethane or 1,2-dichloroethane; ethers such as diethyl ether or tetrahydrofuran; amides such as N,N-dimethylformamide; sulfoxides such as dimethylsulfoxide; nitriles such as acetonitrile; and a mixture of one or more of these solvents. Dichloromethane or 1,2-dichloroethane are particularly preferred.

The reaction can take place over a wide range of temperatures, and the precise reaction temperature is not critical to the present invention. The reaction is conveniently carried out at a temperature of from −70° C. to 90° C., preferably 0° to 60° C. The time required for the reaction varies, mainly depending upon the reaction temperature and upon the nature of the starting materials, reagents and solvents used, and is not critical to the present invention. The reaction period is typically 15 minutes to a whole day, and usually 30 minutes to 6 hours, under suitable reaction conditions.

Where an acid halide of an acid represented by a formula $E^1$—OH is used, the reaction is preferably carried out in the presence of a base. The base used is not critical to the present invention. Examples of preferred bases include organic bases such as, for example, triethylamine, N,N-dimethylaniline, pyridine, 4-dimethylaminopyridine, 1,5-diazabicyclo [4.3.0]non-5-ene (DBN) or 1,8-diazabicyclo[5.4.0]undec-7-ene (DBU).

The precise quantities of acid halide and base used are not critical to the present invention. However, the reaction can conveniently be conducted using 1 to 10 equivalents of an acid halide of an acid of formula $E^1$—OH and 2 to 8 equivalents of a base relative to the compound of general formula (Ib).

The solvent, the reaction temperature and the time required for the reaction, which are used for the reaction with an acid halide of an acid of formula $E^1$—OH, are essentially the same as those used in reaction of a compound of formula (Ib) with a carboxylic acid itself. Typically, the reaction is carried out at a temperature of 0° C. to 50° C., and for a reaction period of from 5 minutes to 2 hours.

After completion of the reaction in each step, the desired compounds of formulae (VIa), (Ia), (Ib) and (Ic) can be recovered from the reaction mixture by conventional means and, if necessary, can be purified by conventional means such as column chromatography.

The milbemycins and analogous natural products, which may be used as the starting material for the synthesis of the compounds of formula (IV) are obtainable as a single compound or as mixtures at various ratios of related compounds, and they may be reacted after being separated into the various fractions or they may be used in the above reactions as mixtures. Therefore, the compound used in each step of the above reactions may be either a single compound or a mixture of compounds. Accordingly, the compounds of formula (Ia), (Ib) or (Ic) may be prepared as a single compound or as a mixture of compounds, and, if prepared as a mixture of compounds, may be used as such or may be separated into the individual compounds prior to use.

The compounds of the present invention of formula (I) wherein X represents a group of formula (III), as defined above, my be prepared as illustrated by the following Reaction Scheme B:

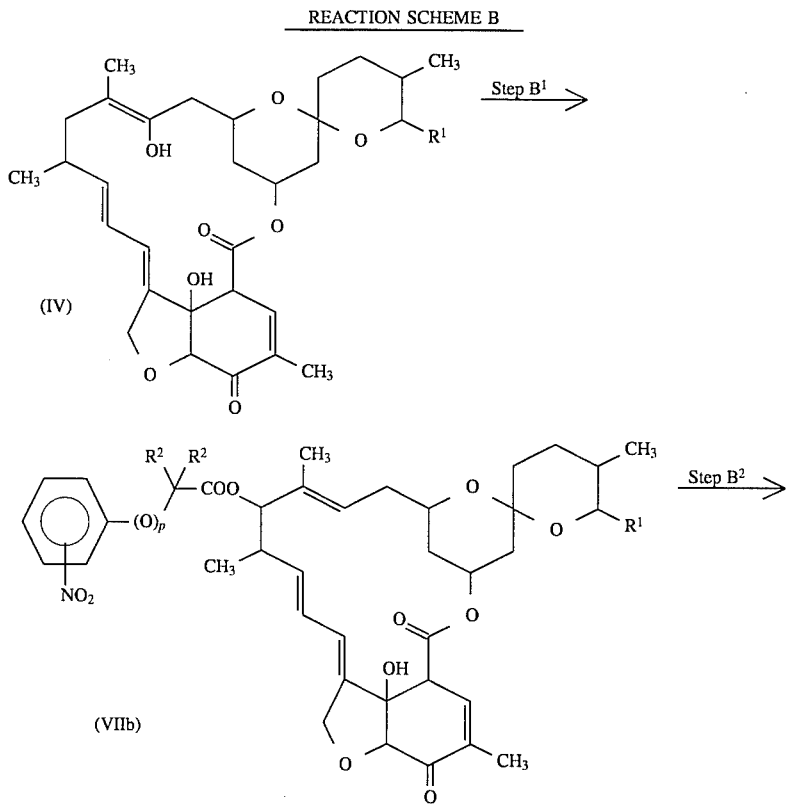

REACTION SCHEME B

-continued
REACTION SCHEME B

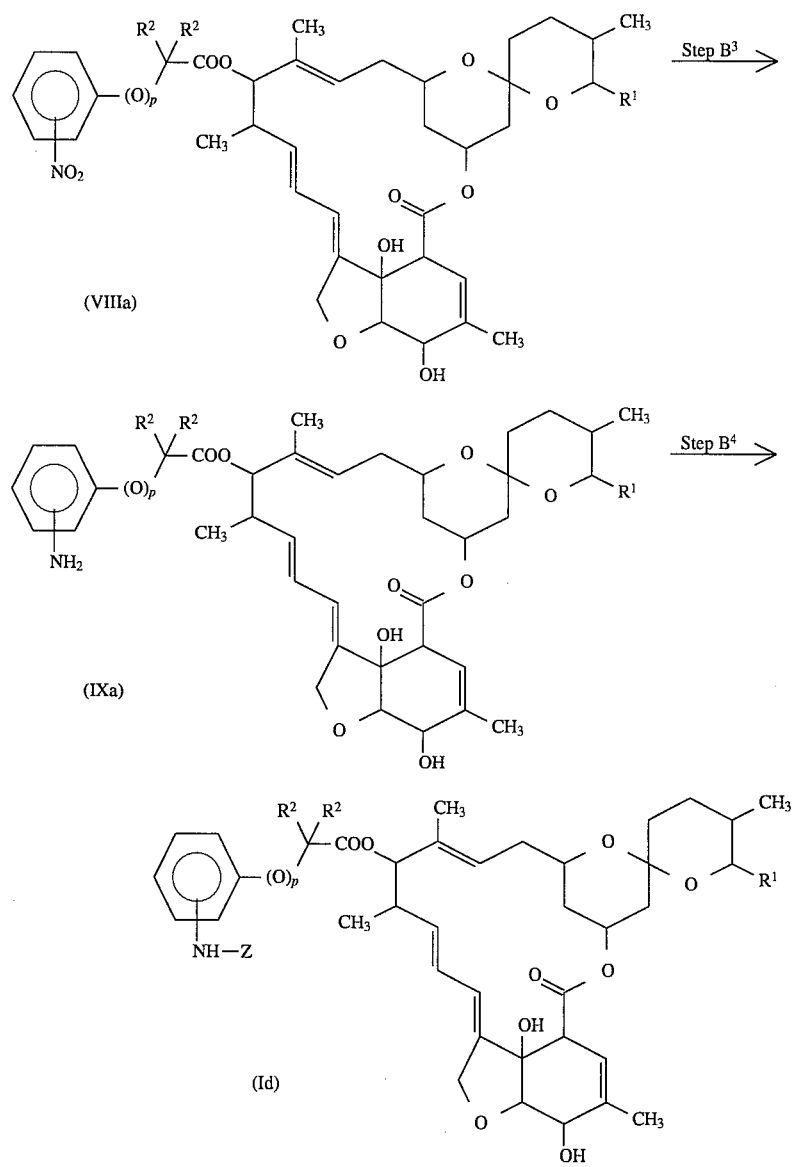

In the formulae of Reaction Scheme B, $R^1$, $R^2$, p and Z are as defined above.

The 15-hydroxymilbemycin derivatives of formula (IV), which are used as a starting material in Step $B^1$, are known compounds disclosed in European Patent Publication 147, 582.

The compound, which is used as the other starting material in Step $B^1$, is represented by formula (Vb):

$$[NO_2C_6H_4-(O)_p-C(R^2)_2-COOH] \quad (Vb)$$

(wherein $R^2$ and p are as defined above) and can be prepared using commercially available reagents as starting materials, by using well-known methods.

Where p is 1, the desired compound (Vb) can be prepared by hydrolysis of an α-(nitrophenoxy)-α-alkylalkanoic acid ester (e.g. an α-(4-nitrophenoxy)-α-alkylalkanoic acid ester) which can be produced by the following steps:

(a) alkylation at the a-position of a commercially available alkanoic acid ester, using an alkyl halide in the presence of a base;

(b) halogenation at the a-position of the α-alkylalkanoic acid ester thus obtained; and (c) reaction of the α-alkyl-α-haloalkanoic acid ester thus obtained (or a commercially available compound) with nitrophenol (e.g. 4-nitrophenol) in the presence of a base.

Where p is 0, the desired compound (Vb) can be prepared by hydrolysis of an α-(nitrophenyl)-α,α-dialkylacetate (e.g. α-(4-nitrophenyl)-α,α-dialkylacetate), which can be produced by alkylation of commercially available nitrophenylacetate (e.g. 4-nitrophenylacetate) at the m-position with an alkyl halide in the presence of a base.

Step $B^1$ of Reaction Scheme B involves the preparation of a compound of general formula (VIIb) by treating a compound of general formula (IV) with a carboxylic acid of general formula (Vb) in the presence of a strong organic acid, such as used for Step $A^1$ of Reaction Scheme A, e.g. trifluoromethanesulfonic acid. The amount of strong organic acid used, preferred conditions such as use of an inorganic accelerator, solvents, reaction time and temperature are suitably all as for Step $A^1$ of Reaction Scheme A.

Step $B^2$ of Reaction Scheme B involves the preparation of the compound of general formula (VIIIa) by reacting a compound of general formula (VIIb) with a reducing agent, to reduce the carbonyl group at the 5-position to a hydroxyl group.

There is no particular limitation upon the reducing agent used, provided that other parts of the compound of formula (VIIb) are not affected when the carbonyl group is reduced. Examples of such reducing agents include those capable of generating a hydride anion, such as sodium borohydride or diborane, preferably sodium borohydride.

The solvent used, the range of reaction temperatures and reaction periods are all suitably as for Step $A^2$ of Reaction Scheme A above.

Step $B^3$ of Reaction Scheme B involves the preparation of a compound of general formula (IXa) having an amino substituent, by reducing the nitro substituent on the phenyl or phenoxy moiety of the compound of general formula (VIIIa) produced in Step $B^2$.

Reduction of the nitro group of the compound of general formula (VIIIa) can be carried out by the conventional means described for optional Step $A^3$ of Reaction Scheme A. Examples of suitable reducing agents, solvents, reaction temperatures and reaction times are all suitably as described above for optional Step $A^3$ of Reaction Scheme A.

Step $B^4$ involves the preparation of a compound of general formula (Id), as defined above, by reacting the ring amino substituent of a compound of general formula (IXa) produced in Step $B^3$ with an acid of the formula Z—OH (in which Z is as defined above) or a reactive derivative thereof.

Suitable reactive derivatives of the acid of formula Z—OH include those used in conventional condensation reactions such as, for example, an acid halide (usually acid chloride or acid bromide), an acid anhydride, a mixed acid anhydride, an activated ester or an activated amide.

Where an acid represented by the formula Z—OH is used, the reaction is preferably carried out in the presence of a dehydrating agent such as, for example, dicyclohexylcarbodiimide (DCC), 2-chloro-1-methylpyridinium iodide, p-toluenesulfonic acid or sulfuric acid, preferably 2-chloro-1-methylpyridinium iodide. The amount of the reagent used is not critical to the invention, but is normally in a range of 1 to 5 equivalents, preferably 1 to 2 equivalents per mol of the acid of a formula Z—OH.

There is no particular limitation upon the nature of the solvent used, provided that it has no adverse effect upon the reaction and can dissolve the starting material to some extent. Examples of preferred solvents include: hydrocarbons such as hexane, petroleum ether, benzene or toluene; halogenated hydrocarbons such as chloroform, dichloromethane or 1,2-dichloroethane; ethers such as diethyl ether or tetrahydrofuran; amides such as N,N-dimethylformamide; sulfoxides such as dimethylsulfoxide; nitriles such as acetonitrile; and a mixture of one or more of these solvents. Dichloromethane or 1,2-dichloroethane are particularly preferred.

The reaction can take place over a wide range of temperatures, and the precise reaction temperature is not critical to the present invention. The reaction is conveniently performed at a temperature of from −70° C. to 90° C., preferably 0° to 60° C. The time required for the reaction varies, mainly depending upon the reaction temperature and upon the nature of the starting materials, reagents and solvents used, and it is not critical to the present invention. The reaction period is typically from 15 minutes to a whole day, and usually 30 minutes to 6 hours, under suitable reaction conditions.

Where an acid halide of an acid represented by the formula Z—OH is used, the reaction is preferably carried out in the presence of a base. The base used is not critical to the present invention. Examples of preferred bases include organic bases such as, for example, triethylamine, N,N-dimethylaniline, pyridine, 4-dimethylaminopyridine, 1,5-diazabicyclo[4.3.0]non-5-ene (DBN) or 1,8-diazabicyclo [5.4.0]undec-7-ene (DBU).

The precise quantities of acid halide and base used are not critical to the present invention. However, the reaction can conveniently be conducted using 1 to 10 equivalents of an acid halide of a formula Z—OH and 2 to 8 equivalents of a base relative to the compound of general formula (IXa).

The solvent, the reaction temperature and the time required for the reaction, which are used for reaction of compounds of formula (IXa) with acid halides of acids of formula Z—OH, are essentially the same as those for reaction with a carboxylic acid itself. Typically, the reaction is carried out at a temperature of 0° C. to 50° C., and a reaction period of from 5 minutes to 2 hours is usually sufficient.

After completion of the reaction in each step, the desired compounds of formulae (VIIb), (VIIIa), (IXa) and (Id) can be recovered from the reaction mixture by conventional means and, if necessary, can be purified by conventional means such as column chromatography.

The milbemycins and analogous natural products, which may be used as the starting material for the synthesis of the compounds of formula (IV) are obtainable as a single compound or as mixtures at various ratios of related compounds, and they may be reacted after being separated into the various fractions or they may be used in the above reactions as mixtures. Therefore, the compound used in each step of the above reactions may be either a single compound or a mixture of compounds. Accordingly, the compound of formula (Id) may be prepared as a single compound or as a mixture of compounds, and, if prepared as a mixture of compounds, may be used as such or may be separated into the individual compounds prior to use.

The compounds of the invention have a strong acaricidal activity against adults and eggs of red spider mites belonging to the families Tetranychidae, Eriophyidae and the like, which are parasitic to fruit trees, vegetables and flowers. They are also active against mites of the families Ixodidae, Dermanyssidae, Sarcoptidae and the like, which are parasitic to animals. Further, they are active against resistant mites, which are difficult to control with known acaricides and which have recently caused much trouble.

The compounds of the invention also have a strong insecticidal activity and can therefore be used as insecticides. The active compounds of the invention exhibit precise preventive effects against noxious insects but have no phytotoxicity, and so agricultural and horticultural plants are never damaged by these compounds. The compounds of the invention can be used to exterminate a variety of noxious insects, including noxious insects which damage plants by sucking or eating them, noxious insects parasitic to plants, noxious insects which damage materials in store, noxious insects for sanitary reasons and the like.

Examples of noxious insects which are susceptible to the compounds of the present invention include: insects of the orders: Coleoptera, for example the azuki bean weevil (*Callosobruchus chinensis*), the rice weevil (*Sitophilus zeamais*), the red flour beetle (*Tribolium castaneum*), the twentyeight spotted ladybird (*Epilachna vigitioctomaculata*), the barley wire (*Agriotes fuscicollis*), the soybean beetle (*Anomala rufocuprea*), the Colorado potato beetle (*Leptinotarsa decemkineata*), diabrotica (Diabrotica spp.), the pine sawyer (*Monochamus alternatus*), the rice water weevil (*Lissorhoptrus oryzophilus*), and the powder post beetle (*Lyctus bruneus*); Lepidoptera, for example the gypsy moth (*Lymantria dispar*), the tent caterpillar (*Malacosoma neustria*), the common cabbage worm (*Pieris rapae*), the common cutworm (*Spodoptera litura*), the cabbage armyworm (*Mamestra brassicae*), the rice stem borer (*Chilo suppressalis*), the oriental corn borer (*Pyrausta nubilalis*), the Mediterranean flour moth (*Ephestia cautella*), the smaller tea tortrix (*Adoxophyes orana*), the codling moth (*Carpocapsa pomenella*), the cutworm (*Agrotis fucosa*), the greater wax moth (*Galleria mellonella*), the diamondback moth (*Plutella mylostella*) and the citrus leafminer (*Phyllocnistis citrella*); Hemiptera, for example the green rice leafhopper (*Nephotettix cincticeps*), the brown rice planthopper (*Nilaparvata lugens*), the Comstock mealybug (*Pseudococus comstocki*), the arrowhead scale insect (*Unaspis yanonensis*), the green peach aphid (*Myzus persicae*), the apple leafcurling aphid (*Aphis pomi*), the cotton aphid (*Aphis gossypii*), the turnip aphid (*Rhopalosiphum pseudobrassicac*), the pear lace bug (*Stephaniris nashi*), the green vegetable bug (Nazara spp.), the bed bug (*Cimex lectularius*), the greenhouse whitefly (*Trialeurodes vaporariorum*) and psylla (Psylla spp); Orthoptera, for example the German cockroach (*Blatella germanica*), the American cockroach (*Periplaneta americana*), the African mole cricket (*Gryllotalpa africana*) and grasshoppers (*Locusta migratoria migratorioides*); Isoptera, for example the Yamato termite (*Deucotermes speratus*) and the Formosan subterranean termite (*Coptotermes formosamus*); and Diptera, for example the house fly (*Mucus domestica*), the seedcorn maggot (*Hylemia platura*), the yellow fever mosquito (*Aedes aegypti*), the common house mosquito (*Culex piplens*), the anopheles mosquito (*Anopheles slnensis*) and the smaller common house mosquito (*Culex tritaeniorhynchus*).

Moreover, in the field of veterinary medicine, the compounds of the invention are effective against various animal helminths (both endo- and ectoparasites), for example insects and worms. Examples of noxious animal helminths include: the horse botfly (Gastrophilus spp.), the stable fly (Stomoxys spp.), the biting louse (Trichodectes spp.), the assassin bug (Rhodnius spp.), and the dog flea (*Ctenocephalides canis*).

The compounds are also effective against various nematodes which affect animals of agricultural importance. In particular, typical genera of nematodes which are parasitic on livestock, poultry and pet animals, such as pigs, sheep, goats, cows, horses, dogs, cats or fowls and against which the compound of the invention are effective include: Haemonchus, Trichostrongylus, Ostertagia, Nematodirus, Cooperia, Ascaris, Bunostomum, Oesophagostomum, Chabertia, Trichuris, Storongylus, Trichonema, Dictyocaulus, Capillaria, Heterakis, Toxocara, Ascaridia, Oxyuris, Ancylostoma, Uncinaria, Toxascaris and Parascaris.

Certain parasitical species of the genera Nematodirus, Cooperia and Oesophagostomum attack the intestines, while certain species of the general Haemonchus and Ostertagia parasitize the stomach, and parasites belonging to the genus Digtyocaulus are found in the lungs. Parasites belonging to families Filariidae and Setariidae are found in the internal tissues and organs, for example, the heart, the blood vessels, the subcutaneous tissues and the lymphatic vessels. The compounds of the invention are active against all these parasites.

The compounds of the invention are also effective against other parasites, such as parasites of the genera Ancylostoma, Necator, Ascaris, Strongyloides, Trichinella, Capillaria, Trichuris and Enterobius.

The compounds are also active against parasites of the genera Wuchereria, Brugia, Onchoceca and Loa of the family Filariidae (which are found in blood, tissues and organs other than the digestive tract and are medically important), parasites of the genus Dracunculus of the family Dracunculidae and endoinestinal parasites of the genera Strongyloides and Trichinell, which especially infest the exointestinal canal.

Where the compounds of the invention are used as anthelmintics in animals, they can be administered orally in the form of a liquid drink. The drink may comprise a solution, suspension or dispersion of the active compound in an appropriate non-toxic solvent or water and in admixture with a suspending agent, such as bentonite, a wetting agent or other excipients. The drink, in general, may also contain an anti-foaming agent. The active compound is normally present in the drink in an amount of from about 0.01 to 0.5% by weight, more preferably from 0.01 to 0.1% by weight.

Compositions can be administered orally in the form of dry solids, preferably in unit dosage form, such as capsules, pills or tablets containing the desired amount of the active compound. These compositions can be prepared by mixing the active compound uniformly with suitable pulverized diluents, fillers, disintegrators and/or binding agents, for example starch, lactose, talc, magnesium stearate and vegetable gum. The weight and contents of the preparation may vary widely, depending upon the nature of the animal to be treated, the degree of infection, the nature of the parasite and the body weight of the animal to be treated.

The compounds can also be administered as an additive to animal feedstuffs, in which case they can be dispersed uniformly in the feedstuffs, used as a top dressing or used in the form of pellets. The content of active compound in the feedstuff is preferably from 0.0001 to 0.02%, in order to achieve the desired anthelmintic activity.

The compounds of the invention, when dissolved or dispersed in a liquid vehicle, can be administered parenterally to animals by injection into the proventriculus, a muscle or the traches or by subcutaneous injection. For parenteral administration, the active compound is preferably mixed with suitable vegetable oil, such as peanut oil or cottonseed oil. The content of the active compound in the formulation is generally from 0.05 to 50% by weight.

The compounds of the invention can also be administered topically in admixture with a suitable carrier, such as dimethyl sulfoxide or a hydrocarbon solvent. Such preparations are applied directly to the outside of the animal by spraying or by dipping.

The dose of the active compound may vary, depending upon the nature of the animal to be treated, and the nature and degree of parasitic infection. However, best results for oral administration are achieved when the dose is from about 0.01 to 100 mg, more preferably from 0.5 to 50 mg, per 1 kg body weight. The compound can be administered in a single dose or in divided doses for a relatively short period, such as from 1 to 5 days.

Where the composition of the invention is intended for agricultural or horticultural use, a variety of forms and formulations are possible. For example, it can be formulated as dusts, coarse dusts, soluble powders, microgranules, fine microgranules, wettable powders, dilute emulsions, emusifiable concentrates, aqueous or oily suspensions or aqueous or oily solutions (which can be directly sprayable or can be used for dilution), aerosols or capsules in polymeric substances. The carrier used can be natural or synthetic and organic or inorganic, and it is generally employed to assist the active compound to reach the substrate to be treated, and to make it easier to store, transport or handle the active compound. Solid, liquid and gaseous carriers can be chosen from carriers well known in the art for use with composition of this type.

Such formulations may be prepared by conventional means, e.g. by intimate mixing and/or grinding of the active ingredient(s) with a carrier or diluent (solvent) and, optionally, one or more surfactants.

Examples of suitable solvents include: aromatic hydrocarbons, particularly $C_8$ to $C_{12}$ fractions from petroleum distillation, such as xylene mixtures or substituted naphthalenes; esters of phthalic acid, such as dibutyl or dioctyl phthalate; aliphatic or alicyclic hydrocarbons, such as cyclohexane or paraffins; alcohols, such as ethanol, ethylene glycol, ethylene glycol monomethyl ether or ethylene glycol monoethyl ether; glycols or ethers thereof; ketones, such as cyclohexanone; polar solvents, such as N-methyl-2-pyrrolidone, dimethyl sulfoxide or dimethylformamide; optionally epoxidized vegetable oils, such as epoxidized coconut oil or soybean oil; and water.

Examples of carriers which may be used, for example, in dusts and dispersible powders include: natural mineral fillers, such as calcite, talc, kaolin, montmorillonite or attapulgite. In order to improve the physical properties of the composition, it is also possible to add highly dispersed silicic acid or highly dispersed absorbent polymers. Examples of suitable granulated adsorptive carriers include: porous substances, such as pumice, ground brick, sepiolite and bentonite; and non-porous substances, such as calcite and sand. A wide variety of pregranulated materials, organic and inorganic, can be used: examples include dolomite and ground plant residues.

When one or more surfactants are used, these can be cationic, anionic and non-ionic compounds having good emulsifying, dispersing and wetting properties, which are per se conventional in the formulation of agrochemicals and the like. A single such surfactant or mixtures of such surfactants can also be used.

Non-ionic surfactants which can be employed include: polyoxyethylenealkyl ethers; polyoxyethylenealkyl esters; polyoxyethylenealkyl aryl ethers; polyoxyethylenearyl aryl ethers; polyoxyethylenesorbitan alkyl esters; sorbitan alkyl esters; fatty acid esters of sugars; fatty acid esters of glycerol or of pentaerythritol; surfactants of the Pluronic type; acetylenealcohols, acetylenediols, and their ethylene oxide adducts; silicone surfactants; and alkylglucosides. Anionic surfactants which can be employed include: alkylbenzenesulfonic acid salts; dialkylsulfosuccinic acid salts; alkylsulfate salts; alkylmethyltauride salts; anionic surfactants prepared by esterification of sulfuric acid or phosphoric acid with the aforementioned ethylene oxide adduct non-ionic surfactants followed, if necessary, by neutralization with a suitable alkali; ligninsulfonic acid salts; alkylnaphthalenesulfonic acid salts and condensates thereof; phenolsulfonic acid salts and condensates thereof; polysoaps of polycarboxylic acids or polysulfonic acids in the form of salts or of condensates with, for example, acrylic acid, maleic acid, styrenesulfonic acid or with a vinyl radical; surfactants of the starch type, consisting of additives of starch or dextrin with 1-(2-octenoyl)-sodium succinate; carboxymethylcellulose salts; soaps such as the sodium or potassium salts of higher fatty acids; and salts of α-olefin-sulfonic acids.

Cationic surfactants which can be employed include amine salt or quaternary ammonium surfactants, and ethylene dioxide adducts of higher aliphatic amines or fatty acid amides.

Amphoteric surfactants which can be employed include those of the amino acid type or betaine type, or lecithin.

Derivatives of the various aforementioned surfactants in which one or more hydrogen atoms have been substituted by fluorine have been found to exhibit a strong surface tension lowering effect, and can be used advantageously in the compositions of the present invention.

The compositions of the invention can also contain one or more additives selected from the group consisting of stabilizers, anti-foaming agents, viscosity regulators, binders and adhesives or any combination thereof, as well as fertilizers and other active substances to achieve special effects.

Insecticidal and acaricidal compositions generally contain: from 0.01 to 99%, more preferably from 0.1 to 95%, of the active compound; from 1 to 99.99% of a solid or liquid additive; and from 0 to 25%, more preferably from 0.1 to 25%, of a surface-active agent. Where commercial products are generally sold as concentrated compositions, they are generally diluted by the end-user to a concentration of from 0.001 to 0.0001% by weight (from 10 to 1 ppm).

In the above, percentages are by weight.

The compounds of the present invention can be formulated in admixture with or used in association with other active compounds, for example, insecticides, poisonous feeds, bacteriocides, acaricides, nematocides, fungicides, plant growth regulators or herbicides. Examples of the said insecticides include: organic phosphorus chemicals, carbamate chemicals, carboxylate chemicals, chlorinated hydrocarbon chemicals and insecticidal substances produced by microorganism.

The compounds of the invention can also be formulated in admixture with or used in association with synergists. It is required that preparations of such chemicals and the form of the intended use are commercially useful. The synergist is, independently of the activity, in itself a compound capable of enhancing the effect of the active compounds.

The invention is further illustrated by the following non-limiting Examples, Preparations and Formulation Examples, which illustrate respectively the preparation of certain of the compounds of the invention, starting materials used in preparing the compounds of the invention, and agrochemical formulations containing the compounds of the invention. The compounds of the present invention are identified by the numbers assigned to them in the foregoing Tables 1, 2 and 3.

EXAMPLE 1

13-(α-Methoxyiminophenylacetoxy)milbemycin $A_4$ (isomer A)

(Step A)

13-(α-Methoxyiminophenylacetoxy)-5-ketomilbemycin $A_4$

One drop of trifluoromethanesulfonic acid was added, with ice-cooling under a stream of argon, to a mixture of 100 mg (0.18 mmol) of 15-hydroxy-5-ketomilbemycin $A_4$, 64.5 mg (0.36 mmol) of α-methoxyiminophenylacetic acid (a less polar isomer) and 68 mg of copper iodide (I) in 5 ml of dichloromethane. The resulting mixture was stirred at room temperature for one hour. At the end of this time, the reaction mixture was poured into water and extracted with ethyl acetate. The extract was washed with a 5% aqueous solution of sodium bicarbonate then with a saturated aqueous solution of sodium chloride, and dried over anhydrous magnesium sulfate. The solvent was distilled off and the resulting residue was purified by column chromatography through silica gel, eluted with a stepwise gradient of ethyl acetate (10–50%) in hexane, to give 53 mg of the title compound (yield 41%).

Mass spectrum (m/z): 717 (M$^+$), 659, 539, 520, 502.

Nuclear Magnetic Resonance Spectrum (CDCl$_3$, 200 MHz) δ ppm: 7.46–7.54 (2H, multiplet), 7.31–7.41 (3H, multiplet), 6.55 (1H, singlet), 5.78–5.93 (2H, multiplet), 5.38–5.57 (3H, multiplet), 5.20 (1H, doublet, J=10.9 Hz), 3.99 (3H, singlet), 3.86 (1H, singlet).

(Step B)

13-(α-Methoxyiminophenylacetoxy)milbemycin A$_4$ (isomer A)

[Compound No. 1- 72]

3.0 mg (0.08 mmol) of sodium borohydride were added with ice-cooling to a solution of 43.2 mg (0.06 mmol) of 13-(α-methoxyiminophenylacetoxy)-5-ketomilbemycin A$_4$ in 4 ml of methanol, and the resulting mixture was stirred at 0° C. for 30 minutes. At the end of this time, the reaction mixture was poured into water followed by extracting with ethyl acetate. The extract was washed with water then with a saturated aqueous solution of sodium chloride, and dried over anhydrous magnesium sulfate. The solvent was distilled off and the resulting residue was purified by column chromatography through silica gel, eluted with a stepwise gradient of ethyl acetate (25–50%) in hexane, to give 38 mg (64%) of the title compound.

Mass spectrum (m/z): 719 (M$^+$), 591, 540, 412, 394, 279.

Nuclear Magnetic Resonance Spectrum (CDCl$_3$, 270 MHz) δppm: 7.48–7.54 (2H, multiplet), 7.31–7.42 (3H, multiplet), 5.78–5.87 (2H, multiplet), 5.51 (1H, doublet of doublets, J=8.0, 12.0 Hz), 5.31–5.47 (3H, multiplet), 5.20 (1H, doublet, J=10.9 Hz), 3.99 (3H, singlet), 3.98 (1H, singlet).

EXAMPLES 2 TO 27

The compounds of Examples 2 to 27 were synthesized by following procedures similar to those described in the above Example 1. As in Example 1, the 5-keto derivative of the desired milbemycin compound was first prepared in Step A, and this was then converted to the final product in Step B. The yield (%) of each Step is specified after each compound number. An asterisk in parentheses (*) denotes that the product obtained was used in the subsequent reaction without further purification, and thus its yield was not estimated in that Step.

EXAMPLE 2

13-(2-Methoxyimino-2-phenylethoxy)milbemycin A$_4$

[Compound No. 1-11: Step A (*)–Step B (48%)]

Mass spectrum (m/z): 750 (M$^+$), 687, 656, 554, 540, 504.

Nuclear Magnetic Resonance Spectrum (CDCl$_3$, 200 MHz) δ ppm: 7.60–7.69 (2H, multiplet), 7.28–7.39 (3H, multiplet), 5.63–5.81 (2H, multiplet), 5.13–5.46 (4H, multiplet), 4.45 (2H, singlet), 3.98 (3H, singlet), 3.21–3.30 (2H, multiplet).

EXAMPLE 3

13-[2-Methoxyimino-2-(2-chlorophenyl)ethoxy]milbemycin A$_4$

[Compound No. 1-12: Step A (*)–Step B (74%)]

Mass spectrum (m/z): 739 (M$^+$), 721, 690, 540, 460.

Nuclear Magnetic Resonance Spectrum (CDCl$_3$, 200 MHz) δ ppm: 7.25–7.40 (4H, multiplet), 5.57–5.78 (2H, multiplet), 5.14–5.42 (4H, multiplet), 4.37 and 4.54 (2H, AB-quartet, J=15.7 Hz), 3.96 (3H, multiplet), 3.16 (1H, doublet, J=9.9 Hz).

EXAMPLE 4

13-[2-Methoxyimino-2-(3-fluorophenyl)ethoxy]milbemycin A$_4$

[Compound No. 1-13: Step A (*)–Step B (55%)]

Mass spectrum (m/z): 723 (M$^+$), 674, 572, 540, 444, 414.

Nuclear Magnetic Resonance Spectrum (CDCl$_3$, 200 MHz) δ ppm: 7.28–7.46 (3H, multiplet), 6.99–7.07 (1H, multiplet), 5.67–5.81 (2H, multiplet), 5.14–5.46 (4H, multiplet), 3.98 (3H, singlet).

EXAMPLE 5

13-[2-Methoxyimino-2-(3-chlorophenyl)ethoxy]milbemycin A$_4$

[Compound No. 1-14: Step A (*)–Step B (61%)]

Mass spectrum (m/z): 739 (M$^+$), 690, 611, 540, 460.

Nuclear Magnetic Resonance Spectrum (CDCl$_3$, 200 MHz) δ ppm: 7.65 (1H, singlet), 7.52–7.58 (1H, multiplet), 7.25–7.36 (2H, multiplet), 5.65–5.80 (2H, multiplet), 5.15–5.45 (4H, multiplet), 4.42 (2H, singlet), 3.98 (3H, singlet).

EXAMPLE 6

13-(α-Methoxyiminophenylacetoxy)milbemycin A$_4$ (isomer B)

[Compound No. 1-73: Step A (*)–Step B (55%)]

Mass spectrum (m/z): 719 (M$^+$), 591, 540, 458, 412, 394.

Nuclear Magnetic Resonance Spectrum (CDCl$_3$, 200 MHz) δ ppm: 7.30–7.46 (5H, multiplet), 5.70–5.89 (2H, multiplet), 5.29–5.48 (4H, multiplet), 5.10 (1H, doublet, J=10.5 Hz), 4.04 (3H, singlet).

EXAMPLE 7

13-(α-Methoxyiminophenylacetoxy)milbemycin A$_3$

[Compound No. 1-38: Step A (78%)–Step B (75%)]

Mass spectrum (m/z): 705 (M$^+$), 577, 526, 398, 380.

Nuclear Magnetic Resonance Spectrum (CDCl$_3$, 200 MHz) δ ppm: 7.45–7.55 (2H, multiplet), 7.28–7.40 (3H, multiplet), 5.71–5.91 (2H, multiplet), 5.29–5.60 (4H, multiplet), 5.19 (1H, doublet, J=10.6 Hz), 3.98 (3H, singlet).

EXAMPLE 8

13-(α-Methoxyimino-2-chlorophenylaacetoxy)milbemycin A$_4$

[Compound No. 1-74: Step A (*)–Step B (20%)]

Mass spectrum (m/z): 753 (M$^+$), 625, 540.

Nuclear Magnetic Resonance Spectrum (CDCl$_3$, 200 MHz) δ ppm: 7.55–7.60 (2H, multiplet), 7.25–7.41 (3H, multiplet), 5.78–5.91 (2H, multiplet), 5.28–5.52 (4H, multiplet), 5.12 (1H, doublet, J=10.5 Hz), 4.04 (3H, singlet).

EXAMPLE 9

13-(α-Methoxyimino-3-fluorophenylacetoxy)milbemycin A$_4$

[Compound No. 1-75: Step A (*)–Step B (60%)]

Mass spectrum (m/z): 737 (M$^+$), 680, 609, 552, 522.

Nuclear Magnetic Resonance Spectrum (CDCl$_3$, 200 MHz) δ ppm: 5.77–5.98 (2H, multiplet), 5.30–5.61 (4H, multiplet), 5.20 (1H, doublet, J=10.6 Hz), 4.00 (3H, singlet).

EXAMPLE 10

13-(α-Methoxyimino-3-chlorophenylacetoxy)milbemycin $A_4$
[Compound No. 1-76: Step A (*)–Step B (55%)]
  Mass spectrum (m/z): 753 ($M^+$), 625, 540, 456, 412, 394.
  Nuclear Magnetic Resonance Spectrum ($CDCl_3$, 200 MHz) δ ppm: 7.25–7.55 (4H, multiplet), 5.72–5.87 (2H, multiplet), 5.30–5.49 (4H, multiplet), 5.20 (1H, doublet, J=10.4 Hz), 4.01 (3H, singlet).

EXAMPLE 11

13-(α-Methoxyimino-4-chlorophenylacetoxy)milbemycin $A_4$ (isomer A)
[Compound No. 1-77: Step A (*)–Step B (34.0%)]
  Mass spectrum (m/z): 753 ($M^+$), 625, 522, 456, 412.
  Nuclear Magnetic Resonance Spectrum ($CDCl_3$, 270 MHz) δ ppm: 7.42–7.46 (2H, multiplet), 7.31–7.36 (2H, multiplet), 5.82–5.90 (2H, multiplet), 5.34–5.54 (4H, multiplet), 5.19 (1H, doublet, J=10.5 Hz), 3.99 (3H, singlet), 3.97 (1H, doublet, J=6.0 Hz).

EXAMPLE 12

13-(α-Methoxyimino-4-chlorophenylacetoxy)milbemycin $A_4$ (isomer B)
[Compound No. 1-78: Step A (55.8%)–Step B (70.8%)]
  Mass spectrum (m/z): 753 ($M^+$), 625, 522, 444, 412.
  Nuclear Magnetic Resonance Spectrum ($CDCl_3$, 270 MHz) δ ppm: 7.32–7.40 (4H, multiplet), 5.77–5.88 (2H, multiplet), 5.33–5.47 (4H, multiplet), 5.10 (1H, doublet, J=10.5 Hz), 4.05 (3H, singlet), 3.96 (1H, doublet, J=6.5 Hz).

EXAMPLE 13

13-(α-Ethoxyimino-4-chlorophepylacetoxy)milbemycin $A_4$ (isomer A)
[Compound No. 1-79: Step A (45%)–Step B (44%)]
  Mass spectrum (m/z): 767 ($M^+$), 639, 554, 522, 412.
  Nuclear Magnetic Resonance Spectrum ($CDCl_3$, 270 MHz) δ ppm: 7.43–7.48 (2H, multiplet), 7.30–7.37 (2H, multiplet), 5.79–5.90 (2H, multiplet), 5.34–5.54 (4H, multiplet), 5.20 (1H, doublet, J=10.5 Hz), 4.24 (2H, quartet, J=5.2 Hz), 3.96 (1H, doublet, J=6.4 Hz), 1.28 (3H, triplet, J=7.3 Hz).

EXAMPLE 14

13-(α-Ethoxyimino-4-chlorophenylacetoxy)milbemycin $A_4$ (isomer B)
[Compound No. 1-80: Step A (33%)–Step B (65%)]
  Mass spectrum (m/z): 767 ($M^+$), 639, 540, 444, 412.
  Nuclear Magnetic Resonance Spectrum ($CDCl_3$, 270 MHz) δ ppm: 7.32–7.44 (4H, multiplet), 5.75–5.88 (2H, multiplet), 5.30–5.46 (4H, multiplet), 5.09 (1H, doublet, J=10.9 Hz), 4.31 (2H, quartet, J=7.1 Hz), 3.96 (1H, doublet, J=6.5 Hz), 1.30 (3H, triplet, J=7.1 Hz).

EXAMPLE 15

13-(α-Methoxyimino-4-nitrophenylacetoxy)milbemycin $A_4$
[Compound No. 1-81: Step A (*)–Step B (40%)]
  Mass spectrum (m/z): 764 ($M^+$), 540, 504.
  Nuclear Magnetic Resonance Spectrum ($CDCl_3$, 200 MHz) δ ppm: 8.27 (2H, doublet, J=8.6 Hz), 7.56 (2H, doublet, J=8.6 Hz), 5.72–5.90 (2H, multiplet), 5.26–5.51 (4H, multiplet), 5.11 (1H, doublet, J=10.7 Hz), 4.08 (3H, singlet).

EXAMPLE 16

13-(α-Methoxyimino-2-hydroxyphenylacetoxy)milbemycin $A_4$
[Compound No. 1-89: Step A (*)–Step B (24%)]
  Mass spectrum (m/z): 735 ($M^+$), 703, 634, 556, 540.
  Nuclear Magnetic Resonance Spectrum ($CDCl_3$, 270 MHz) δ ppm: 9.96 (1H, singlet), 7.38–7.48 (1H, multiplet), 6.91–7.18 (3H, multiplet), 5.90–6.03 (2H, multiplet), 5.63–5.71 (1H, multiplet), 5.40–5.58 (3H, multiplet), 5.34 (1H, doublet, J=10.0 Hz), 4.12 (3H, singlet).

EXAMPLE 17

13-(α-Methoxyimino-2-methoxyphenylacetoxy)milbemycin $A_4$ (isomer A)
[Compound No. 1-90: Step A (*)–Step B (20%)]
  Mass spectrum (m/z): 749 ($M^+$), 634, 600, 558, 506, 472, 412.
  Nuclear Magnetic Resonance Spectrum ($CDCl_3$, 270 MHz) δ ppm: 7.82 (1H, doublet of doublets, J=1.7, 7.6 Hz), 7.46 (1H, doublet of triplets, J=1.7, 7.6 Hz), 7.06 (1H, triplet, J=7.6 Hz), 6.95 (1H, doublet, J=7.6 Hz), 5.85–5.99 (2H, multiplet), 5.41–5.64 (4H, multiplet), 5.25 (1H, doublet, J=10.4 Hz), 4.08 (3H, singlet), 3.76 (3H, singlet).

EXAMPLE 18

13-(α-Methoxyimino-2-methoxyphenylacetoxy)milbemycin $A_4$ (isomer B)
[Compound No. 1-91: Step A (*)–Step B (15%)]
  Mass spectrum (m/z): 749 ($M^+$), 621, 522, 412, 394, 355.
  Nuclear Magnetic Resonance Spectrum ($CDCl_3$, 270 MHz) δ ppm: 7.27–7.42 (1H, multiplet), 7.08 (1H, doublet, J=8.1 Hz), 6.87–7.01 (1H, multiplet), 6.78 (1H, doublet, J=8.1 Hz), 5.74–5.89 (2H, multiplet), 5.23–5.45 (4H, multiplet), 5.09 (1H, doublet, J=10.4 Hz), 4.03 (3H, singlet), 3.72 (3H, singlet).

EXAMPLE 19

13-(α-Methoxyimino-2-ethoxyphenylacetoxy)milbemycin $A_4$ (isomer A)
[Compound No. 1-92: Step A (*)–Step B (15%)]
  Mass spectrum (m/z): 763 ($M^+$), 586, 540.
  Nuclear Magnetic Resonance Spectrum ($CDCl_3$, 270 MHz) δ ppm: 7.64 (1H, doublet of doublets, J=1.7, 7.5 Hz), 7.34 (1H, doublet of triplets, J=1.7, 7.5 Hz), 6.96 (1H, triplet, J=7.5 Hz), 6.85 (1H, doublet, J=7.5 Hz), 5.71–5.90 (2H, multiplet), 5.31–5.53 (4H, multiplet), 5.10 (1H, doublet, J=10.4 Hz), 3.99 (3H, singlet), 3.90–4.05 (3H, multiplet).

EXAMPLE 20

13- (α-Methoxyimino-2-ethoxyphenylacetoxy)milbemycin $A_4$ (isomer B)
[Compound No. 1-93: Step A (*)–Step B (12%)]
  Mass spectrum (m/z): 763 ($M^+$), 634, 540, 506, 442, 412.
  Nuclear Magnetic Resonance Spectrum ($CDCl_3$, 200 MHz) δ ppm: 7.25–7.39 (1H, multiplet), 6.72–7.14 (3H, multiplet), 5.70–5.90 (2H, multiplet), 5.28–5.50 (4H, multiplet), 5.08 (1H, doublet, J=10.7 Hz), 4.03 (3H, singlet), 3.89–4.11 (3H, multiplet).

EXAMPLE 21

13-(α-Methoxyimino-2-benzyloxyphenylacetoxy)milbemycin $A_4$
[Compound No. 1-98: Step A (*)–Step B (15%)]

Mass spectrum (m/z): 825 ($M^+$), 697, 630, 540, 522, 412.

Nuclear Magnetic Resonance Spectrum ($CDCl_3$, 270 MHz) δ ppm: 7.67–7.71 (1H, multiplet), 7.23–7.35 (6H, multiplet)m 6.75–6.94 (2H, multiplet), 5.72–5.88 (2H, multiplet), 5.29–5.42 (4H, multiplet), 5.22 (1H, doublet, J=10.3 Hz), 5.01–5.09 (2H, multiplet), 4.00 (3H, singlet).

EXAMPLE 22

13-[α-Methoxyimino-(2-pyridyl)acetoxy)milbemycin $A_4$
[Compound No. 1-111: Step A (15%)–Step B (78%)]

Mass spectrum (m/z): 720 ($M^+$), 702, 540, 522, 412.

Nuclear Magnetic Resonance Spectrum ($CDCl_3$, 270 MHz) δ ppm: 8.66–8.68 (1H, doublet, J=4.8 Hz), 7.73–7.79 (1H, multiplet), 7.59–7.62 (1H, doublet, J=8.1 Hz), 7.28–7.33 (1H, multiplet), 5.74–5.85 (2H, multiplet), 5.20–5.44 (4H, multiplet), 5.11 (1H, doublet, J=10.5 Hz), 4.06 (1H, singlet), 3.96 (1H, doublet, J=6.0 Hz).

EXAMPLE 23

13-(3-Methoxyimino-3-phenylpropionyloxy)milbemycin $A_4$
[Compound No. 1-186: Step A (61%)–Step B (74%)]

Mass spectrum (m/z): 733 ($M^+$), 702, 605, 586, 572, 554, 540.

Nuclear Magnetic Resonance Spectrum ($CDCl_3$, 200 MHz) δ ppm: 7.68–7.77 (2H, multiplet), 7.41–7.50 (3H, multiplet), 5.84–5.91 (2H, multiplet), 5.39–5.51 (4H, multiplet), 5.03 (1H, doublet, J=10.5 Hz), 4.07 (3H, singlet), 3.83 (2H, broad singlet).

EXAMPLE 24

13-(α-Hydroxyiminophenylacetoxy)milbemycin $A_4$
[Compound No. 1-70: Step A (61%)–Step B (41%)]

Mass spectrum (m/z): 705 ($M^+$), 577, 540, 522, 504, 412, 394, 279.

Nuclear Magnetic Resonance Spectrum ($CDCl_3$, 200 MHz) δ ppm: 9.45 (1H, broad singlet), 5.71–5.90 (2H, multiplet), 5.21–5.51 (4H, multiplet,) 5.12 (1H, doublet, J=10.5 Hz), 4.68 (2H, broad singlet), 4.30 (1H, triplet, J=7.4 Hz), 4.10 (1H, singlet), 3.97 (1H, doublet, J=6.2 Hz).

EXAMPLE 25

13-(α-Methoxyimino-2-thienylacetoxy)milbemycin $A_4$
[Compound No. 1-102: Step A (*)–Step B (93%)]

Mass spectrum (m/z): 725 ($M^+$), 597, 554, 522.

Nuclear Magnetic Resonance Spectrum ($CDCl_3$, 200 MHz) δ ppm: 7.32–7.38 (1H, multiplet), 6.95–7.04 (4H, multiplet), 5.74–5.92 (2H, multiplet), 5.27–5.58 (4H, multiplet), 5.18 (1H, doublet, J=10.5Hz), 4.69 (2H, broad singlet), 4.30 (1H, multiplet), 4.09 (1H, singlet), 3.96 (4H, broad singlet).

EXAMPLE 26

13-[α-Methoxyimino-(2-chloroacetylaminothiazol-4-yl)acetoxy]milbemycin $A_4$
[Compound No. 1-108: Step A (*)–Step B (60%)]

Fast atom bombardment mass spectrum (m/z): 967 ($M^+$+ 150, $C_{40}H_{52}ClN_3O_{11}S$+triethanolamine+H).

Nuclear Magnetic Resonance Spectrum ($CDCl_3$, 200 MHz) δ ppm: 9.85 (1H, broad singlet), 7.07 (1H, singlet), 5.76–5.93 (2H, multiplet), 5.28–5.69 (4H, multiplet), 5.18 (1H, doublet, J=10.4 Hz), 4.69 (2H, broad singlet), 4.29 (3H, broad singlet), 4.09 (1H, singlet), 4.03 (2H, singlet), 3.97(1H, doublet, J=6.2 Hz).

EXAMPLE 27

13-(α-Methoxyimino-3-furanylacetoxy)milbemycin $A_4$
[Compound No. 1-100: Step A (,) Step B (64%)]

Nuclear Magnetic Resonance Spectrum ($CDCl_3$, 200 MHz) δ ppm: 7.50 (1H, doublet, J=1.8 Hz), 6.45–6.53 (2H, multiplet), 5.78–5.92 (2H, multiplet), 5.29–5.54 (4H, multiplet), 5.16 (1H, doublet, J=10.6 Hz), 4.69 (2H, broad singlet), 4.30 (1H, multiplet), 4.08 (1H, singlet), 3.99 (4H, broad singlet).

EXAMPLE 28

13-[α-Methoxyimino)-(2-aminothiazol-4-yl)acetoxy]milbemycin $A_4$
[Compound No. 1-107]

340 mg of cadmium powder were added, at room temperature, to a solution of 92 mg (0.1 mmol) of 13-[2-methoxyimino-{2-(2,2,2-trichloroethoxycarbonylamino)thiazol-4-yl}acetoxy]milbemycin $A_4$ (produced by the procedure of Example 37 below) in dimethlyformamide and acetic acid (1:1 by volume), and the resulting mixture was stirred for 2 hours. The reaction mixture was then poured into a mixture of 5 ml of ethyl acetate and 5 ml of water, and stirred for few minutes. Insolubles were filtered off and the filtrate was separated into an ethyl acetate layer and an aqueous layer. The aqueous layer was extracted several times with a few ml of ethyl acetate. The combined ethyl acetate extracts were collected, washed first with a 4% aqueous solution of sodium bicarbonate and then with a saturated aqueous solution of sodium chloride, and dried over anhydrous sodium sulfate. The solvent was evaporated off in vacuo and the residue was purified by column chromatography through silica gel, eluted with a stepwise gradient of ethyl acetate (25–50%) in hexane, to give 33.2 mg of the title compound (45% yield).

Fast atom bombardment mass spectrum (m/z): 891 ($M^+$+ 150, $C_{38}H_{51}N_3O_{10}S$+triethanolamine+H).

Nuclear Magnetic Resonance Spectrum ($CDCl_3$, 200 MHz) δppm: 6.56 (1H, singlet), 5.73–5.90 (2H, multiplet), 5.29–5.55 (4H, multiplet), 5.20 (2H, singlet), 5.15 (1H, doublet, J=10.6 Hz), 4.69 (2H, broad singlet), 4.29 (1H, multiplet), 4.09 (1H, singlet), 3.99 (4H, broad singlet).

EXAMPLE 29

13-[α-Methoxyimino-(4-methoxycarbonylaminoacetylaminophenyl)acetoxy]milbemycin $A_4$
[Compound No. 2-45]
(Step A)
13-(α-Methoxyimino-4-nitrophenylacetoxy)-5-ketomilbemycin $A_4$ One drop of trifluoromethanesulfonic acid was added, under a stream of argon while cooling with ice, to a solution of 843 mg (1.52 mmol) of 15-hydroxy-5-ketomilbemycin $A_4$, 694 mg (3.03 mmol) of α-methoxyimino4-nitrophenylacetic acid and 289 mg of copper(I) iodide in 5 ml of dichloromethane. The resulting mixture was stirred at room temperature for an hour, then the reaction mixture was poured into water and extracted with ethyl acetate. The extract was washed first with a 5% aqueous solution of sodium bicarbonate and then with a saturated aqueous solution of sodium chloride, and dried over anhydrous magnesium sulfate. The solvent was distilled off and the residue was purified by column chromatography through silica gel, eluted with a stepwise gradient of ethyl acetate (20–40%) in hexane, to give 663 mg (57% yield) of the title compound.

Nuclear Magnetic Resonance Spectrum (CDCl$_3$, 200 MHz) δ ppm: 8.27 (2H, doublet, J=9.0 Hz), 7.56 (2H, doublet, J=9.0 Hz), 6.54 (1H, multiplet), 5.74–5.94 (2H, multiplet), 5.32–5.54 (3H, multiplet), 5.12 (1H, doublet, J=10.5 Hz), 4.74 (2H, broad singlet), 4.08 (3H, singlet), 4.01 (1H, singlet), 3.88 (1H, singlet).

(Step B)
13-(α-Methoxyimino-4-nitrophenylacetoxy)milbemycin A$_4$ 87 mg (0.44 mmol) of sodium borohydride were added to a solution of 337 mg (0.44 mmol) of 13-(α-methoxyimino-4-nitrophenylacetoxy)-5-ketomilbemycin A$_4$ in 40 ml of methanol, while cooling with ice, and the resulting mixture was stirred at 0° C. for 30 minutes. The reaction mixture was then poured into water and extracted with ethyl acetate. The extract was washed, in turn, with water and with a saturated aqueous solution of sodium chloride, and dried over anhydrous magnesium sulfate. The solvent was distilled off and the residue was purified by column chromatography through silica gel, eluted with a stepwise gradient of ethyl acetate (30–50%) in hexane, to give 332 mg (98% yield) of the title compound.

Mass spectrum (m/z): 764 (M$^+$), 540, 504.

Nuclear Magnetic Resonance Spectrum (CDCl$_3$, 200 MHz) δ ppm: 8.27 (2H, doublet, J=8.6 Hz), 7.56 (2H, doublet, J=8.6 Hz), 5.72–5.90 (2H, multiplet), 5.26–5.51 (4H, multiplet), 5.11 (1H, doublet, J=10.7 Hz), 4.08 (3H, singlet).

(Step C)
13-(α-Methoxyimino-4-aminophenylacetoxy)milbemycin A$_4$ 1.19 g of zinc powder were added at room temperature to a solution of 1.98 g (2.59 mmol) of 13-(α-methoxyimino-4-nitrophenylacetoxy)milbemycin A$_4$ in 20 ml of acetic acid, and the resulting mixture was stirred for 2 hours. The reaction mixture was then mixed with ethyl acetate and insolubles were filtered off. The filtrate was diluted with water and extracted with ethyl acetate. The extract was washed with a 4% aqueous solution of sodium bicarbonate and dried over anhydrous sodium sulfate. The solvent was distilled off and the residue was purified by column chromatography through silica gel, eluted with a stepwise gradient of ethyl acetate (40–100%) in hexane, to give 789 mg (41% yield) of the title compound.

Nuclear Magnetic Resonance Spectrum (CDCl$_3$, 200 MHz) δ ppm: 7.30 (2H, doublet, J=7.1 Hz), 6.61 (2H, doublet, J=7.1 Hz), 5.78–5.88 (2H, multiplet), 5.28–5.54 (4H, multiplet), 5.17 (1H, doublet, J=10.6 Hz), 4.66 and 4.70 (2H, AB-quartet, J=15.5 Hz), 4.30 (1H, triplet, J=7.0 Hz), 3.93 (3H, singlet).

(Step D: Acylation step)
13-[α-Methoxyimino-(4-methoxycarbonylaminoacetylaminophenyl)acetoxy]milbemycin A$_4$ 1.50 g (2.04 mmol) of 13-(α-methoxyimino-4-aminophenylacetoxy)milbemycin A$_4$, 0.597 ml (4.28 mmol) of triethylamine and 1.095 g (4.28 mmol) of 2-chloro-2-methylpyridinium iodide were added in turn to a solution of 0.815 g (6.12 mmol) of N-methoxycarbonyl glycine in 10 ml of dichloromethane, and the resulting mixture was stirred at room temperature for 1.5 hours. At the end of this time, the reaction mixture was poured into water and extracted with ethyl acetate. The extract was dried over anhydrous magnesium sulfate and concentrated. The concentrate was purified by column chromatography through silica gel, eluted with a stepwise gradient of ethyl acetate (30–100%) in hexane, to give 268 mg (92% yield) of the title compound.

Fast atom bombardment mass spectrum: 999 (M$^+$+150, C$_{45}$H$_{59}$N$_3$O$_{13}$+triethanolamine+H).

Nuclear Magnetic Resonance Spectrum (CDCl$_3$, 200 MHz) δ ppm: 8.13–8.25 (1H, broad singlet), 7.55 (2H, doublet, J=8.7 Hz), 7.47 (2H, doublet, J=8.7 Hz), 5.75–5.92 (2H, multiplet), 5.27–5.69 (4H, multiplet), 5.19 (1H, doublet, J=10.4 Hz), 4.69 (2H, broad singlet), 4.50 (1H, multiplet), 4.11 (1H, singlet), 3.97 (3H, broad singlet), 3.76 (3H, singlet).

EXAMPLES 30 TO 36

The compounds of Examples 30 to 36 were synthesized by following procedures similar to those described in the above Example 29. The yield (%) obtained in the acylation step (Step D) is specified after each compound number.

EXAMPLE 30

13-(α-Methoxyimino-4-acetylaminophenylacetoxy)milbemycin A$_4$
[Compound No. 1-83: Step D (70%)]
Mass spectrum (m/z): 776 (M$^+$), 758, 522.

Nuclear Magnetic Resonance Spectrum (CDCl$_3$, 200 MHz) δ ppm: 7.42–7.59 (4H, multiplet), 7.29 (1H, singlet), 5.75–5.93 (2H, multiplet), 5.28–5.59 (4H, multiplet), 5.20 (1H, doublet, J=10.5 Hz), 4.70 (2H, broad singlet), 4.31 (1H, multiplet), 4.11 (1H, singlet),

EXAMPLE 31

13-[α-Methoxyimino-(2-acetylaminothiazol-4-yl)acetoxy]milbemycin A$_4$
[Compound No. 1-204: Step D (55%)]
Fast atom bombardment mass spectrum (m/z): 933 (M$^+$+150, C$_{40}$H$_{53}$N$_3$O$_{11}$S+triethanolamine+H).

Nuclear Magnetic Resonance Spectrum (CDCl$_3$, 200 MHz) δ ppm: 9.37 (1H, singlet), 7.00 (1H, singlet), 5.74–5.90 (2H, multiplet), 5.29–5.59 (4H, multiplet), 5.17 (1H, doublet, J=10.4 Hz), 4.69 (2H, broad singlet), 4.34 (1H, multiplet), 4.12 (1H, singlet), 3.99 (4H, broad singlet).

EXAMPLE 32

13-[2-Methoxyimino-2-(4-acetylaminoacetylaminophenyl)ethoxy]milbemycin A$_4$
[Compound No. 2-7, Step D (65%)]
Fast atom bombardment mass spectrum: 912 (M$^+$+150, C$_{43}$H$_{58}$N$_2$O$_{10}$+triethanolamino+H).

Nuclear Magnetic Resonance Spectrum (CDCl$_3$, 200 MHz) δ ppm: 7.62 (2H, doublet, J=8.8 Hz), 7.50 (2H, doublet, J=8.8 Hz), 5.64–5.80 (2H, multiplet), 5.18–5.43 (4H, multiplet), 4.66 (2H, broad singlet), 4.42 (2H, broad singlet), 4.28 (1H, multiplet), 3.99 (1H, singlet), 3.96 (4H, broad singlet).

EXAMPLE 33

13-[2-Methoxyimino-2-(4-methanesulfonylaminophenyl)ethoxy]milbemycin A$_4$
[Compound No. 2-16, Step D (70%)]
Fast atom bombardment mass spectrum: 948 (M$^+$+150, C$_{42}$H$_{58}$N$_2$O$_{11}$S+triethanolamine+H).

Nuclear Magnetic Resonance Spectrum (CDCl$_3$, 200 MHz) δ ppm: 7.65 (2H, doublet, J=8.7 Hz), 7.21 (2H, doublet, J=8.7 Hz), 6.83 (1H, singlet), 5.64–5.82 (2H, multiplet), 5.17–5.43 (4H, multiplet), 4.66 (2H, broad singlet), 4.43 (2H, broad singlet), 4.30 (1H, broad singlet), 3.97 (3H, singlet), 3.92 (1H, doublet, J=3.8 Hz).

EXAMPLE 34

13-[α-Methoxyimino-(4-methanesulfonylaminophenyl)acetoxy]milbemycin A$_4$
[Compound No. 2-22, Step D (75%)]

Mass spectrum (m/z): 812 (M$^+$), 522.

Nuclear Magnetic Resonance Spectrum (CDCl$_3$, 200 MHz) δ ppm: 7.51 (2H, doublet, J=8.6 Hz), 7.12 (2H, doublet, J=8.6 Hz), 6.67 (1H, singlet), 5.77–5.94 (2H, multiplet), 5.28–5.59 (4H, multiplet), 5.20 (1H, doublet, J=10.7 Hz), 4.69 (2H, broad singlet), 4.30 (1H, doublet, J=6.2 Hz), 3.98 (4H, broad singlet).

EXAMPLE 35

13-[α-Methoxyimino-(4-acetylaminoacetylaminophenyl)acetoxy]milbemycin A$_4$
[Compound No. 2-39, Step D (45%)]

Fast atom bombardment mass spectrum: 983 (M$^+$+150, C$_{45}$H$_{59}$N$_3$O$_{12}$S+triethanolamine+H).

Nuclear Magnetic Resonance Spectrum (CDCl$_3$, 200 MHz) δ ppm: 8.77 (1H, singlet), 7.56 (2H, doublet, J=8.8 Hz), 7.47 (2H, doublet, J=8.8 Hz), 6.43 (1H, triplet, J=5.1 Hz), 5.76–5.92 (2H, multiplet), 5.28–5.59 (4H, multiplet), 5.19 (1H, doublet, J=10.7 Hz), 4.69 (2H, broad singlet), 4.30 (1H, multiplet), 4.12 (3H, broad singlet), 3.98 (4H, broad singlet).

EXAMPLE 36

13-[α-Methoxyimino-(4-methoxycarbonylaminoacetylaminophenyl)acetoxy]milbemycin A$_3$
[Compound No. 2-43, Step D (85%)]

Nuclear Magnetic Resonance Spectrum (CDCl$_3$, 200 MHz) δ ppm: 8.14 (1H, broad singlet), 7.55 (2H, doublet, J=8.8 Hz), 7.47 (2H, doublet, J=8.8 Hz), 5.72–5.91 (2H, multiplet), 5.27–5.59 (4H, multiplet), 5.20 (1H, doublet, J=10.4 Hz), 4.69 (2H, broad singlet), 4.30 (1H, multiplet), 3.85–4.12 (4H, multiplet), 3.97 (3H, singlet).

EXAMPLE 37

13-[α-Methoxyimino-(2-(2,2,2-trichloroethoxycarbonylamino)thiazol-4-yl)acetoxy]milbemycin A$_4$
[Compound No. 2-101: Step A (*)–Step B (65%)]

Fast atom bombardment mass spectrum (m/z): 1065 (M+150, C$_{41}$H$_{52}$Cl$_3$N$_3$O$_{12}$S+triethanolamine+H).

Nuclear Magnetic Resonance Spectrum (CDCl$_3$, 200 MHz) δ ppm: 7.07 (1H, singlet), 5.77–5.92 (2H, multiplet), 5.28–5.49 (4H, multiplet), 5.17 (1H, doublet, J=10.5 Hz), 4.88 (2H, singlet), 4.69 (2H, broad singlet), 4.31 (1H, multiplet), 4.00 (4H, broad singlet).

EXAMPLE 38

13-[α-methoxyimino-(2-methoxycarbonylaminothiazol-4-yl)acetoxy]milbemycin A$_4$
[Compound No. 2-99: Step D (50%)]

Fast atom bombardment mass spectrum (m/z): 949 (M++150, C$_{40}$H$_{53}$N$_3$O$_{12}$S+triethanolamine+H).

Nuclear Magnetic Resonance Spectrum (CDCl$_3$, 200 MHz) δ ppm: 8.39 (1H, broad singlet), 6.96 (1H, singlet), 5.76–5.91 (2H, multiplet), 5.27–5.58 (4H, multiplet), 5.17 (1H, doublet, J=10.4 Hz), 4.69 (2H, broad singlet), 4.30 (1H, multiplet), 4.09 (1H, singlet), 4.00 (4H, broad singlet).

EXAMPLE 39

13-[α-Methoxyimino-(2-ethoxycarbonylaminothiazol-4-yl) acetoxy]milbemycin A$_4$
[Compound No. 2-100: Step D (55%)]

Fast atom bombardment mass spectrum (m/z): 963 (M++150, C$_{41}$H$_{55}$N$_3$O$_{12}$S+triethanolamine+H).

Nuclear Magnetic Resonance Spectrum (CDCl$_3$, 200 MHz) δ ppm: 8.24 (1H, broad singlet), 6.98 (1H, singlet), 5.76–5.91 (2H, multiplet), 5.28–5.57 (4H, multiplet), 5.17 (1H, doublet, J=10.4 Hz), 4.69 (2H, broad singlet), 4.32 (3H, quartet, J=7.0 Hz), 4.09 (1H, singlet), 4.00 (3H, singlet), 3.97 (1H, doublet, J=6.7 Hz),

EXAMPLE 40

13-[α-Methoxyimino-(2-isopropoxycarbonylaminothiazol-4-yl) acetoxy]milbemycin A$_4$
[Compound No. 2-105: Step D (60%)]

Fast atom bombardment mass spectrum (m/z): 977 (M++150, C$_{42}$H$_{57}$N$_3$O$_{12}$S+triethanolamine+H).

Nuclear Magnetic Resonance Spectrum (CDCl$_3$, 200 MHz) δ ppm: 8.31 (1H, broad), 6.98 (1H, singlet), 5.76–5.92 (2H, multiplet), 5.28–5.58 (4H, multiplet), 5.17 (1H, doublet, J=10.4 Hz), 5.08 (multiplet, J=6.3 Hz), 4.69 (2H, broad singlet), 4.31 (1H, triplet, J=6.2 Hz), 4.10 (1H, singlet), 4.00 (3H, singlet), 3.98 (1H, doublet, J=6 Hz).

EXAMPLE 41

13-[α-Methoxyimino-[2-(1-methoxycarbonylpyrrolydine-2-ylcarbonylamino)thiazol-4-yl] acetoxy] milbemycin A$_4$
[Compound No. 2-106: Step D (50%)]

Fast atom bombardment mass spectrum (m/z): 1046 (M$^+$+150, C$_{45}$H$_{60}$N$_4$O$_3$S+triethanolamine+H).

Nuclear Magnetic Resonance Spectrum (CDCl$_3$, 200 MHz) δ ppm: 10.22 (1H, broad singlet), 7.05 (1H, singlet), 5.74–5.91 (2H, multiplet), 5.28–5.57 (4H, multiplet), 5.17 (1H, doublet, J=10.4 Hz), 4.69 (2H, broad singlet), 4.53 (1H, broad), 4.30 (1H, triplet, J=6.1 Hz), 4.09 (1H, singlet), 4.02 ( 3H, singlet), 3.97 (1H, doublet, J=6 Hz),

EXAMPLE 42

13-[α-Methoxyimino-(2-methoxycarbonylaminoacetylaminothiazol-4-yl)acetoxy]milbemycin A$_4$
[Compound No. 2-103: Step D (45%)]

Fast atom bombardment mass spectrum (m/z): 1006 (M$^+$+150, C$_{42}$H$_{56}$N$_4$O$_{13}$S+triethanolamine+H).

Nuclear Magnetic Resonance Spectrum (CDCl$_3$, 200 MHz) δ ppm: 9.8 (1H, broad singlet), 7.03 (1H, singlet), 5.76–5.91 (2H, multiplet), 5.27–5.66 (4H, multiplet), 5.17 (1H, doublet, J=10.6 Hz), 4.69 (2H, broad singlet), 4.30 (1H, multiplet), 4.12 (1H, singlet), 4.09 (2H, singlet), 4.00 (4H, broad singlet), 3.77 (3H, singlet).

EXAMPLE 43

13-[2-(4-Methoxycarbonylaminoacetylaminophenyl)-2-methylpropionyloxy]milbemycin $A_4$
(Step A)
13-[2-(4-Nitrophenyl)-2-methylpropionyloxy]-5-ketomilbemycin $A_4$ 15 μl of trifluoromethanesulfonic acid were added, with ice-cooling under a stream of argon, to a solution of 188 mg (0.34 mmol) of 15-hydroxy-5-ketomilbemycin $A_4$ and 212 mg (1.01 mmol) of 2-(4-nitrophenyl)-2-methylpropionic acid in 8 ml of dichloromethane. The resulting mixture was stirred at room temperature for 30 minutes. At the end of this time, the reaction mixture was poured into water and extracted with ethyl acetate. The extract was washed first with a 5% aqueous solution of sodium bicarbonate then a saturated aqueous solution of sodium chloride, and dried over anhydrous magnesium sulfate. The solvent was distilled off and the residue was purified by column chromatography through silica gel, eluted with a stepwise gradient of ethyl acetate (10–35%) in hexane, to give 502 mg (58% yield) of the title compound.

Nuclear Magnetic Resonance Spectrum ($CDCl_3$, 270 MHz) δ ppm: 8.16 (2H, doublet, J=9.8 Hz), 6.54 (1H, triplet, J=1.8 Hz), 5.69–5.91 (2H, multiplet), 5.29–5.47 (3H, multiplet), 4.91 (1H, doublet, J=10.5 Hz), 4.70 (2H, broad singlet), 3.84 (1H, singlet), 1.63 (6H, singlet).

(Step B):
13-[2-(4-Nitrophenyl)-2-methylpropionyloxy]milbemycin $A_4$ 38 mg of sodium borohydride were added, with ice-cooling, to a solution of 502 mg (0.671 mmol) of 13-[2-(4-nitrophenyl)-2-methylpropionyloxy)-5-ketomilbemycin $A_4$ in 5 ml of methanol, and the resulting mixture was stirred at 0° C. for 30 minutes. The reaction mixture was then poured into water and extracted with ethyl acetate. The extract was washed first with water then with a saturated aqueous solution of sodium chloride, and dried over anhydrous magnesium sulfate. The solvent was distilled off and the residue was purified by column chromatography through silica gel, eluted with a stepwise gradient of ethyl acetate (20–40%) in hexane, to give 300.4 mg (60% yield) of the title compound.

Nuclear Magnetic Resonance Spectrum ($CDCl_3$, 200 MHz) δ ppm: 8.17 (2H, doublet, J=9.0 Hz), 7.46 (2H, doublet, J=9.0 Hz), 5.66–5.81 (2H, multiplet), 5.25–5.48 (3H, multiplet), 4.90 (1H, doublet, J=10.6 Hz), 4.65 (2H, broad singlet), 4.28 (1H, triplet, J=6.1 Hz), 4.07 (1H, singlet), 3.94 (1H, doublet, J=6.1 Hz).

(Step C)
13-[2-(4-Aminophenyl)-2-methylpropionyloxy]milbemycin $A_4$ 10 mg of zinc powder were added at room temperature to a solution of 23 mg (0.0307 mmol) of 13-[2-(4-nitrophenyl)-2-methylpropionyloxy)milbemycin $A_4$ in 1 ml of acetic acid, and the resulting mixture was stirred for 2 hours. The reaction mixture was then diluted with ethyl acetate, and the diluted mixture was filtered to remove insolubles. The filtrate was mixed with water and extracted with ethyl acetate. The extract was washed first with a 4% aqueous solution of sodium bicarbonate then with a saturated aqueous solution of sodium chloride, and dried over anhydrous sodium sulfate. The solvent was distilled off and the residue was purified by column chromatography through silica gel, eluted with a stepwise/radient of ethyl acetate (30–100%) in hexane, to give 14.7 mg (67% yield) of the title compound.

Nuclear Magnetic Resonance Spectrum ($CDCl_3$, 200 MHz) δ ppm: 7.08 (2H, doublet, J=8.6 Hz), 6.62 (2H, doublet, J=8.6 Hz), 5.68–5.81 (2H, multiplet), 5.21–5.44 (4H, multiplet), 4.85 (1H, doublet, J=10.6 Hz), 4.66 (2H, broad singlet), 4.79 (1H, broad singlet), 4.07 (1H, broad singlet),
3.95 (1H, doublet, J=6.1 Hz).

(Step D)
13-[2-(4-Methoxycarbonylaminoacetylaminophenyl)-2-methylpropionyloxy]milbemycin $A_4$
[Compound No. 3-27]

3.61 g (5.0 mmol) of 13-[2-(4-aminophenyl)-2-methylpropionyloxy]milbemycin $A_4$, 1.012 g (10.0 mmol) of triethylamine and 2.56 g (10.0 mmol) of 2-chloro-1-methylpyridinium iodide were added in turn to a solution of 2.0 g (15.0 mmol) of N-methoxycarbonylglycine in 20 ml of dichloromethane. The resulting mixture was stirred at room temperature for 1.5 hours. At the end of this time, the reaction mixture was poured into water and extracted with ethyl acetate. The extract was dried over anhydrous magnesium sulfate, the solvent was distilled off and the residue was purified by column chromatography through silica gel, eluted with a stepwise gradient of ethyl acetate (30–100%) in hexane, to give 3.53 g (84.4% yield) of the title compound.

Fast atom bombardment mass spectrum: 984 ($M^+$+150, $C_{46}H_{62}O_{12}N_2$+triethanolamine+H).

Nuclear Magnetic Resonance Spectrum ($CDCl_3$, 270 MHz) δ ppm: 8.25 (1H, broad singlet), 7.46 (2H, doublet, J=8.9 Hz), 7.25 (2H, doublet, J=8.9 Hz), 5.70–5.84 (2H, multiplet), 5.61 (1H, broad singlet), 5.21–5.41 (4H, multiplet), 4.86 (1H, doublet, J=10.8 Hz), 4.63 and 4.68 (2H, AB-quartet, J=15.0 Hz), 4.29 (1H, triplet, J=6.0 Hz), 4.12 (1H, singlet), 4.01 (1H, doublet, J=5.6 Hz), 3.94 (1H, doublet, J=6.0 Hz), 3.74 (3H, singlet).

EXAMPLES 44 TO 78

The compounds of Examples 44 to 78 were synthesized by following procedures similar to those described in the Example 37. In order to illustrate in more detail the process of the present invention which is employed, the yields (%) in step D is specified after each compound number.

EXAMPLE 44

13-[2-(4-Acetylaminophenoxy)-2-methylpropionyloxy]milbemycin $A_4$
[Compound No. 3-1 (69%)]

Mass spectrum (m/z): 777 ($M^+$), 759, 741, 540, 522, 412.

Nuclear Magnetic Resonance Spectrum ($CDCl_3$, 270 MHz) δ ppm: 7.29 (2H, doublet, J=9.8 Hz), 7.04 (1H, broad singlet), 6.75 (2H, doublet, J=9.8 Hz), 5.75–5.87 (2H, multiplet), 5.28–5.46 (4H, multiplet), 5.01 (1H, doublet, J=10.5 Hz), 4.64 and 4.70 (2H, AB-quartet, J=15.0 Hz), 4.29 (1H, doublet, J=6.0 Hz), 4.07 (1H, broad singlet), 3.96 (1H, doublet, J=6.0 Hz), 2.15 (3H, singlet).

EXAMPLE 45

13-[2-(4-Acetylaminophenyl)-2-methylpropionyloxy]milbemycin $A_4$
[Compound No. 3-3 (87%)]

Nuclear Magnetic Resonance Spectrum ($CDCl_3$, 200 MHz) δ ppm: 7.43 (2H, doublet, J=8.7 Hz), 7.19 (2H, doublet, J=8.7 Hz), 5.75–5.83 (2H, multiplet), 5.23–5.45 (4H, multiplet), 4.86 (1H, doublet, J=10.5 Hz), 4.65 (2H, broad singlet), 4.29 (1H, triplet, J=6.2 Hz), 4.07 (1H, singlet), 3.95 (1H, doublet, J=6.2 Hz).

EXAMPLE 46

13-[2-(4-Methanesulfonylaminophenoxy)-2-methylpropionyloxy]milbemycin $A_4$
[Compound No. 3-11 (72%]
Mass spectrum (m/z ): 813 (M$^+$), 685, 540, 412, 394.
Nuclear Magnetic Resonance Spectrum (CDCl$_3$, 270 MHz) δ ppm: 7.08 (2H, doublet, J=9.8 Hz), 6.77 (2H, doublet, J=9.8 Hz), 6.39 (1H, singlet), 5.72–5.88 (2H, multiplet), 5.29–5.46 (4H, multiplet), 4.99 (1H, doublet, J=10.8 Hz), 4.64 and 4.69 (2H, AB-quartet, J=15.4 Hz), 4.29 (1H, doublet, J=6.5 Hz), 4.08 (1H, broad singlet), 3.96 (1H, doublet, J=6.5 Hz), 2.95 (3H, singlet).

EXAMPLE 47

13-[2-(4-Ethoxycarbonylaminophenoxy)-2-methylpropionyloxy]milbemycin $A_4$
[Compound No. 3-19 (80%]
Mass spectrum (m/z): 807 (M$^+$), 633, 522, 504.
Nuclear Magnetic Resonance Spectrum (CDCl$_3$, 270 MHz) δ ppm: 7.18 (2H, doublet, J=9.6 Hz), 6.74 (2H, doublet, J=9.6 Hz), 6.48 (1H, broad singlet), 5.71–5.88 (2H, multiplet), 5.27–5.48 (4H, multiplet), 5.01 (1H, doublet, J=10.4 Hz), 4.65 and 4.71 (2H, AB-quartet, J=15.5 Hz), 4.28 (1H, broad singlet), 4.18 (2H, quartet, J=6.9 Hz), 4.08 (1H, broad singlet), 3.96 (1H, doublet, J=6.5 Hz).

EXAMPLE 48

13-[2-(4-Methoxycarbonylaminoacetylaminophenyl)-2-methylpropionyloxy]milbemycin $A_3$
[Compound No. 3-26 (79%)]
Nuclear Magnetic Resonance Spectrum (CDCl$_3$, 200 MHz) δ ppm: 8.02 (1H, broad singlet), 7.45 (2H, doublet, J=8.6 Hz), 7.26 (2H, doublet, J=8.6 Hz), 5.67–5.82 (2H, multiplet), 5.21–5.55 (5H, multiplet), 4.86 (1H, doublet, J=10.6 Hz), 4.65 (2H, broad singlet), 4.28 (1H, triplet, J=6.2 Hz), 4.08 (1H, singlet), 4.00 (2H, doublet, J=6.0 Hz), 3.94 (1H, doublet, J=6.2 Hz), 3.75 (3H, singlet).

EXAMPLE 49

13-[2-(4-Methoxycarbonylaminoacetylaminophenyl)-2-ethylbutyryloxy]milbemycin $A_4$
[Compound No. 3-28 (45%)]
Nuclear Magnetic Resonance Spectrum (CDCl$_3$, 200 MHz) δ ppm: 7.92 (1H, broad singlet), 7.44 (2H, doublet, J=8.5 Hz), 7.18 (2H, doublet, J=8.5 Hz), 5.71–5.75 (2H, multiplet), 5.21–5.46 (4H, multiplet), 4.90 (1H, doublet, J=10.5 Hz), 4.64 (2H, broad singlet), 4.12–4.34 (1H, multiplet), 4.10 (1H, singlet), 3.99 (2H, doublet, J=5.9 Hz), 3.94 (1H, doublet, J=6.2 Hz).

EXAMPLE 50

13-[2-(4-Methoxycarbonylaminoacetylaminophenoxy)-2-methylpropionyloxy]milbemycin $A_4$
[Compound No. 3-29 (23%)]
Nuclear Magnetic Resonance Spectrum (CDCl$_3$, 200 MHz) δ ppm: 7.85 (1H, broad singlet), 7.32 (2H, doublet, J=9.1 Hz), 6.75 (2H, doublet, J=9.1 Hz), 5.72–5.90 (2H, multiplet), 5.25–5.52 (5H, multiplet), 5.01 (1H, doublet, J=10.6 Hz), 4.67 (2H, broad singlet), 4.29 (1H, triplet, J=6.0 Hz), 4.08 (1H, singlet), 3.98 (2H, doublet, J=4.6 Hz), 3.95 (1H, doublet, J=6.0 Hz), 3.74 ( 3H, singlet).

EXAMPLE 51

13-[2-(4-tert-Butoxycarbonylaminoacetylaminophenyl)-2-methylpropionyloxy]milbemycin $A_4$
[Compound No. 3-33) (76%)]
Nuclear Magnetic Resonance Spectrum (CDCl$_3$, 200 MHz) δ ppm: 8.05 (1H, broad singlet), 7.44 (2H, doublet, J=8.7 Hz), 7.26 (2H, doublet, J=8.7 Hz), 5.67–5.84 (2H, multiplet), 5.14–5.95 (4H, multiplet), 4.87 ( 1H, doublet, J=10.5 Hz), 4.66 (2H, broad singlet), 4.28 (1H, triplet, J=6.0 Hz), 4.08 (1H, singlet), 3.95 (2H, doublet, J=6.2 Hz), 3.92 (1H, doublet, J=6.0 Hz).

EXAMPLE 52

13-[2-(4-Benzyloxycarbonylaminoacetylaminophenyl)-2-methylpropionyloxy]milbemycin $A_4$
[Compound No. 3-34 (69%)]
Nuclear Magnetic Resonance Spectrum (CDCl$_3$, 200 MHz) δ ppm: 7.84 (1H, broad singlet), 7.42 (2H, doublet, J=8.8 Hz), 7.37 (5H, singlet), 7.25 (1H, doublet, J=8.8 Hz), 5.68–5.72 (2H, multiplet), 5.24–5.49 (6H, multiplet), 5.18 (2H, singlet), 4.87 (1H, doublet, J=10.4 Hz), 4.65 (2H, broad singlet), 4.29 (1H, triplet, J=6.2 Hz), 4.07 (1H, singlet), 4.00 (2H, doublet, J=5.9 Hz), 3.95 (1H, doublet, J=6.2 Hz).

EXAMPLE 53

13-[2-(4-Benzoylaminoacetylaminophenyl)-2-methylpropionyloxy]milbemycin $A_4$
[Compound No. 3-36 (45%)]
Nuclear Magnetic Resonance Spectrum (CDCl$_3$, 200 MHz) δ ppm: 9.17 (1H, singlet), 7.89 (2H, doublet, J=7.6 Hz), 7.41–7.61 (5H, multiplet), 7.25 (2H, doublet, J=7.6 Hz), 5.66–5.84 (2H, multiplet), 5.21–5.44 (4H, multiplet), 4.86 (1H, doublet, J=10.4 Hz), 4.64 (2H, broad singlet), 4.40 (2H, doublet, J=4.8 Hz), 4.28 (1H, broad singlet), 4.16 (1H, singlet), 3.94 (1H, doublet, J=6.2 Hz).

EXAMPLE 54

13-[2-(4-(N-Methyl)methoxycarbonylaminoacetylaminophenyl)-2-methylpropionyloxy]milbemycin $A_4$
[Compound No. 3-37 (75%)]
Nuclear Magnetic Resonance Spectrum (CDCl$_3$, 200 MHz) δ ppm: 8.60 (1H, broad singlet), 7.45 (2H, doublet, J=8.7 Hz), 7.26 (2H, doublet, J=8.7 Hz), 5.68–5.85 (2H, multiplet), 5.21–5.45 (4H, multiplet), 4.87 (1H, doublet, J=10.3 Hz), 4.66 (2H, broad singlet), 4.29 (1H, triplet, J=6.2 Hz), 4.07 (1H, singlet), 4.03 (2H, singlet), 3.95 (1H, doublet, J=6.2 Hz), 3.78 (3H, singlet).

EXAMPLE 55

13-[2-[4-(N-Methyl)ethoxycarbonylaminoacetylaminophenyl]-2-methylpropionyloxy]milbemycin $A_4$
[Compound No. 3-38 (89%)]
Nuclear Magnetic Resonance Spectrum (CDCl$_3$, 200 MHz) δ ppm: 8.15 (1H, broad singlet), 7.44 (2H, doublet, J=8.7 Hz), 7.25 (2H, doublet, J=8.7 Hz), 5.68–5.88 (2H, multiplet), 5.23–5.45 (4H, multiplet), 4.87 (1H, doublet, J=10.5 Hz), 4.66 (2H, broad singlet), 4.29 (1H, triplet, J=6.2 Hz), 4.22 (2H, quartet, J=14 Hz), 4.07 (1H, singlet), 4.02 (2H, singlet), 3.95 (1H, doublet, J=6.2 Hz).

EXAMPLE 56

13-[2-(4-Isopropoxycarbonylaminoacetylaminophenyl)-2-methylpropionyloxy]milbemycin $A_4$
[Compound No. 3-39 (68%)]

Nuclear Magnetic Resonance Spectrum (CDCl$_3$, 200 MHz) δ ppm: 8.00 (1H, broad singlet), 7.44 (2H, doublet, J=8.7 Hz), 7.26 (2H, doublet, J=8.7 Hz), 5.68–5.85 (2H, multiplet), 5.22–5.45 (5H, multiplet), 4.98 (1H, heptuplet, J=6.2 Hz), 4.87 (1H, doublet, J=10.6 Hz), 4.66 (2H, broad singlet), 4.28 (1H, triplet, J=5.9 Hz), 4.08 (1H, singlet), 3.98 (2H, doublet, J=5.5 Hz), 3.95 (1H, doublet, J=5.9 Hz).

EXAMPLE 57

13-[2-α-(4-Methoxycarbonylamino)-α-phenylacetylaminophenyl)-2-methylpropionyloxy]milbemycin $A_4$
[Compound No. 3-40 (76%)]

Nuclear Magnetic Resonance Spectrum (CDCl$_3$, 200 MHz) δ ppm: 7.29–7.48 (7H, multiplet), 7.22 (2H, doublet, J=8.6 Hz), 6.02 (1H, doublet, J=5.9 Hz), 5.67–5.82 (2H, multiplet), 5.19–5.45 (4H, multiplet), 4.86 (1H, doublet, J=10.6 Hz), 4.65 (2H, broad singlet), 4.28 (1H, triplet, J=6.2 Hz), 4.08 (1H, singlet), 3.95 (1H, doublet, J=6.2 Hz), 3.69 (3H, singlet).

EXAMPLE 58

13-[2-(4-Ethoxycarbonylaminoacetylaminoacetylaminophenyl)-2-methylpropionyloxy]milbemycin $A_4$
[Compound No. 3-41 (53%)]

Nuclear Magnetic Resonance Spectrum (CDCl$_3$, 200 MHz), δ ppm: 8.38 (1H, singlet), 7.51 (2H, doublet, J=8.4 Hz), 7.24 (2H, doublet, J=8.4 Hz), 6.98 (1H, broad singlet), 5.68–5.85 (2H, multiplet), 5.23–5.49 (5H, multiplet), 4.86 (1H, doublet, J=10.5 Hz), 4.65 (2H, broad singlet), 4.06–4.36 (6H, multiplet), 3.87–3.99 (3H, multiplet),

EXAMPLE 59

13-[2-[4-(Methoxycarbonylamino)benzoylaminoacetylaminophenyl]-2-methylpropionyloxy]milbemycin $A_4$
[Compound No. 3-42 (69%)]

Nuclear Magnetic Resonance Spectrum (CDCl$_3$, 200 MHz) δ ppm: 8.71 (1H, singlet), 7.82 (2H, doublet, J=8.6 Hz), 7.48 (doublet, 4H, J=8.3 Hz), 7.25 (2H, doublet, J=8.6 Hz), 6.94 (1H, singlet), 5.69–5.85 (2H, multiplet), 5.23–5.44 (4H, multiplet), 4.87 (1H, doublet, J=10.6 Hz), 4.65 (2H, broad singlet), 4.23–4.48 (3H, multiplet), 4.09 (1H, singlet), 3.94 (1H, doublet, J=6.1 Hz), 3.81 (3H, singlet).

EXAMPLE 60

13-[2-(4-Methoxycarbonylaminoacetylaminoacetylaminophenyl)-2-methylpropionyloxy]milbemycin $A_4$
[Compound No. 3-43 (48%)]

Nuclear Magnetic Resonance Spectrum (CDCl3, 200 MHz) δ ppm: 8.51 (1H, singlet), 7.51 (2H, doublet, J=8.2 Hz), 7.24 (2H, doublet, J=8.2 Hz), 5.70–5.84 (2H, multiplet), 5.63 (1H, broad), 5.23–5.42 (5H, multiplet), 4.65 (2H, broad singlet), 3.83–4.35 (7H, multiplet).

EXAMPLE 61

13-[2-[4-{3-(Methoxycarbonylamino)propionylamino}phenyl]-2-methylpropionyloxy]milbemycin $A_4$
[Compound No. 3-46 (66%)]

Nuclear Magnetic Resonance Spectrum (CDCl$_3$, 200 MHz) δ ppm: 7.44 (2H, doublet, J=8.6 Hz), 7.25 (2H, doublet, J=8.6 Hz), 5.68–5.83 (2H, multiplet), 5.24–5.46 (5H, multiplet), 4.87 (1H, doublet, J=10.3 Hz), 4.65 (2H, broad singlet), 4.28 (1H, triplet, J=6.1 Hz), 4.07 (1H, singlet), 3.95 (1H, doublet, J=6.1 Hz), 3.67 (3H, singlet).

EXAMPLE 62

13-[2-[4-{2-(Methoxycarbonylamino)propionylamino}phenyl]-2-methylpropionyloxy]milbemycin $A_4$
[Compound No. 3-47 (78%)]

Nuclear Magnetic Resonance Spectrum (CDCl$_3$, 200 MHz) δ ppm: 8.12 (1H, broad singlet), 7.46 (2H, doublet, J=8.6 Hz), 7.25 (2H, doublet, J=8.6 Hz), 5.68–5.83 (2H, multiplet), 5.17–5.45 (5H, multiplet), 4.87 (1H, doublet, J=10.6 Hz), 4.66 (2H, broad singlet), 4.22–4.42 (5H, multiplet), 4.08 (1H, singlet), 3.95 (1H, doublet, J=6.1 Hz), 3.73 (3H, singlet).

EXAMPLE 63

13-[2-{4-(Acetylaminoacetylamino)phenyl}-2-methylpropionyloxy]milbemycin $A_4$
[Compound No. 3-48 (45%)]

Nuclear Magnetic Resonance Spectrum (CDCl$_3$, 270 MHz) δ ppm: 8.72 (1H, broad singlet), 7.47 (2H, doublet, J=8.5 Hz), 7.25 (2H, doublet, J=8.5 Hz), 6.61 (1H, broad singlet), 5.66–5.80 (2H, multiplet), 5.26–5.41 (4H, multiplet), 4.86 (1H, doublet, J=10.5 Hz), 4.61 and 4.67 (2H, AB-quartet, J=15.5 Hz), 4.28 (1H, triplet, J=6.4 Hz), 4.12 (3H, singlet), 3.95 (1H, doublet, J=6.4 Hz).

EXAMPLE 64

13-[2-[4-{3-(Ethoxycarbonylamino)propionylamino}phenyl]-2-methylpropionyloxy]milbemycin $A_4$
[Compound No. 3-49 (66%)]

Nuclear Magnetic Resonance Spectrum (CDCl$_3$, 200 MHz) δ ppm: 7.50 (1H, broad singlet), 7.45 (2H, doublet, J=8.6 Hz), 7.25 (2H, doublet, J=8.6 Hz), 5.68–5.82 (2H, multiplet), 5.22–5.44 (5H, multiplet), 4.87 (1H, doublet, J=10.6 Hz), 4.65 (2H, broad singlet), 4.29 (1H, triplet, J=6.2 Hz), 4.11 (2H, quartet, J=7.1 Hz), 4.07 (1H, singlet), 3.95 (1H, doublet, J=6.2 Hz).

EXAMPLE 65

13-[2-[4-{2-(Methoxycarbonylamino)-2-methylpropionylamino}phenyl]-2-methylpropionyloxy]milbemycin $A_4$
[Compound No. 3-56 (51%)]

Nuclear Magnetic Resonance Spectrum (CDCl$_3$, 200 MHz) δ ppm: 8.63 (1H, broad singlet), 7.46 (2H, doublet, J=8.7 Hz), 7.24 (2H, doublet, J=8.7 Hz), 5.68–5.82 (2H, multiplet), 5.24–5.43 (4H, multiplet), 5.10 (1H, singlet), 4.88 (1H, doublet, J=10.4 Hz), 4.66 (2H, broad singlet), 4.29 (1H, triplet, J=6.2 Hz), 4.07 (1H, singlet), 3.95 (1H, doublet, J=6.2 Hz), 3.71 (3H, singlet).

EXAMPLE 66

13-[2-[4-{2-(Methoxycarbonylamino)-4-(methylthio)butyrylamino}phenyl]-2-methylpropionyloxy]milbemycin $A_4$
(Compound No. 3-58) (72%)

Nuclear Magnetic Resonance Spectrum (CDCl$_3$, 200 MHz) δ ppm: 8.13 (1H, broad singlet), 7.46 (2H, doublet, J=8.7 Hz), 7.26 (2H, doublet, J=8.7 Hz), 5.69–5.83 (2H, multiplet), 5.26–5.49 (5H, multiplet), 4.87 (1H, doublet, J=10.5 Hz), 4.66 (2H, broad singlet), 4.47 (1H, quartet, J=8.1 Hz), 4.29 (1H, triplet, J=6.2 Hz), 4.07 (1H, singlet), 3.95 (1H, doublet, J=6.2 Hz), 3.73 (3H, singlet).

EXAMPLE 67

13-[2-[4-{2-(Methoxycarbonylamino)-3-methylbutyrylamino}phenyl]-2-methylpropionyloxy]milbemycin $A_4$
[Compound No. 3-61 (78%)]

Nuclear Magnetic Resonance Spectrum (CDCl$_3$, 200 MHz) δ ppm: 7.83 (1H, broad singlet), 7.47 (2H, doublet, J=8.7 Hz), 7.24 (2H, doublet, J=8.7 Hz), 5.69–5.83 (2H, multiplet), 5.22–5.46 (5H, multiplet), 4.87 (1H, doublet, J=10.3 Hz), 4.65 (2H, broad singlet), 4.28 (1H, triplet, J=6.2 Hz), 4.08 (1H, singlet), 3.95 (1H, doublet, J=6.2 Hz), 3.71 (3H, singlet).

EXAMPLE 68

13-[2-[4-{2-(Ethoxycarbonylamino)-3-methylbutyrylamino}phenoxy]-2-methylpropionyloxy]milbemycin $A_4$
[Compound No. 3-62 (52%)]

Nuclear Magnetic Resonance Spectrum (CDCl$_3$, 200 MHz) δ ppm: 7.81 (1H, singlet), 7.33 (2H, doublet, J=9.0 Hz), 6.76 (2H, doublet, J=9.0 Hz), 5.72–5.90 (2H, multiplet), 5.18–5.50 (multiplet 5H), 5.01 (1H, doublet, J=10.6 Hz), 4.68 (1H, broad singlet), 4.29 (1H, triplet, J=6.2 Hz), 4.08 (1H, singlet), 3.96 (1H, doublet, J=6.2 Hz), 3.71 (3H, singlet).

EXAMPLE 69

13-[2-[4-{2-(Methoxycarbonylamino)-4-methylpentanoxyamino}phenyl]-2-methylpropionyloxy]milbemycin $A_4$
[Compound No. 3-64 (73%)]

Nuclear Magnetic Resonance Spectrum (CDCl$_3$, 200 MHz) δ ppm:
8.02 (1H, broad singlet), 7.46 (2H, doublet, J=8.6 Hz), 7.24 (2H, doublet, J=8.6 Hz), 5.69–5.81 (2H, multiplet), 5.24–5.45 (4H, multiplet), 5.10 (1H, doublet, J=8.3 Hz), 4.87 (1H, doublet, J=10.6 Hz), 4.65 (2H, broad singlet), 4.20–4.34 (2H, multiplet), 4.08 (1H, singlet), 3.95 (1H, doublet, J=6.3 Hz), 3.72 (3H, singlet).

EXAMPLE 70

13-[2-[4-{2-(Methoxycarbonylamino)-3,3-dimethylbutyrylamino}phenyl]-2-methylpropionyloxy]milbemycin $A_4$
[Compound No. 3-65 (61%)]

Nuclear Magnetic Resonance Spectrum (CDCl$_3$, 200 MHz) δ ppm: 7.90 (1H, broad singlet), 7.45 (2H, doublet, J=8.7 Hz), 7.24 (2H, doublet, J=8.7 Hz), 5.67–5.83 (2H, multiplet), 5.55 (1H, doublet, J=9.8 Hz), 5.24–5.44 (4H, multiplet), 4.87 (1H, doublet, J=10.4 Hz), 4.65 (2H, broad singlet), 4.28 (1H, triplet, J=6.2 Hz), 4.08 (1H, singlet), 3.95 (1H, doublet, J=6.2 Hz), 3.70 (3H, singlet).

EXAMPLE 71

13-[2-[4-{1-(Methoxycarbonylamino)cyclohexane-1-carbonylamino}phenoxy]-2-methylpropionyloxy]milbemycin $A_4$
[Compound No. 3-66 (37%)]

Nuclear Magnetic Resonance Spectrum (CDCl$_3$, 200 MHz) δ ppm: 8.81 (1H, broad singlet), 7.34 (2H, doublet, J=8.8 Hz), 6.75 (2H, doublet, J=8.8 Hz), 5.71–5.89 (2H, multiplet), 5.24–5.49 (4H, multiplet), 5.01 (1H, doublet, J=10.5 Hz), 4.89 (1H, singlet), 4.68 (2H, broad singlet), 4.29 (1H, triplet, J=6.2 Hz), 4.07 (1H, singlet), 3.96 (1H, doublet, J=6.2 Hz), 3.71 (1H, singlet).

EXAMPLE 72

13-[2-[4-{1-(Ethoxycarbonylamino)cyclohexane-1-carbonylamino}phenyl]-2-methylpropionyloxy]milbemycin $A_4$
[Compound No. 3-68 (55%)]

Nuclear Magnetic Resonance Spectrum (CDCl$_3$, 200 MHz) δ ppm: 8.98 (1H, broad singlet), 7.47 (2H, doublet, J=8.6 Hz), 7.24 (2H, doublet, J=8.6 Hz), 5.68–5.85 (2H, multiplet), 5.23–5.46 (4H, multiplet), 4.88 (1H, doublet, J=10.5 Hz), 4.87 (1H, singlet), 4.66 (2H, broad singlet), 4.28 (1H, triplet, J=6.3 Hz), 4.07 (1H, singlet), 3.95 (1H, doublet, J=6.3 Hz), 3.72 (3H, singlet).

EXAMPLE 73

13-[2-[4-[(1-Methoxycarbonylpyrrolidine)-2-carbonylamino]phenyl]-2-methylpropionyloxy]milbemycin $A_4$
[Compound No. 3-69 (78%)]

Nuclear Magnetic Resonance Spectrum (CDCl$_3$, 200 MHz) δ ppm: 7.47 (2H, doublet, J=8.8 Hz), 7.24 (2H, doublet, J=8.8 Hz), 5.67–5.82 (2H, multiplet), 5.23–5.45 (4H, multiplet), 4.88 (1H, doublet, J=10.5 Hz), 4.66 (2H, broad singlet), 4.28 (1H, triplet, J=6.1 Hz), 4.07 (1H, singlet), 3.95 (1H, doublet, J=6.1 Hz), 3.78 (3H, singlet).

EXAMPLE 74

13-[2-[4-(1-Methoxycarbonylpiperidine-2-carbonylamino)phenyl]-2-methylpropionyloxy]milbemycin $A_4$
[Compound No. 3-71 (65%)]

Nuclear Magnetic Resonance Spectrum (CDCl$_3$, 200 MHz) δ ppm: 7.94 (1H, broad singlet), 7.45 (2H, doublet, J=8.7 Hz), 7.24 (2H, doublet, J=8.71 Hz), 5.68–5.82 (2H, multiplet), 5.23–5.46 (4H, multiplet), 4.86–4.97 (2H, broad singlet), 4.66 (2H, multiplet), 4.28 (1H, triplet, J=6.2 Hz), 4.08–4.20 (1H, multiplet), 4.06 (1H, singlet), 3.95 (1H, doublet, J=6.2 Hz).

EXAMPLE 75

13-[2-[4-(1-Methoxycarbonylpiperidine-4-carbonylamino)phenyl]-2-methylpropionyloxy]milbemycin $A_4$
[Compound No. 3-72 (91%)]

Nuclear Magnetic Resonance Spectrum (CDCl$_3$, 200 MHz) δ ppm: 7.47 (2H, doublet, J=8.7 Hz), 7.26 (2H, doublet, J=8.7 Hz), 5.68–5.81 (2H, multiplet), 5.24–5.44 (5H, multiplet), 4.82–4.93 (2H, multiplet), 4.62–4.77 (3H, multiplet), 4.38–4.49 (1H, multiplet), 4.29 (1H, triplet, J=6.2 Hz), 4.07 (1H, singlet), 3.95 (1H, doublet, J=6.2 Hz), 3.83 (3H, singlet).

EXAMPLE 76

13-[2-[4-(3-Methoxycarbonyl-1,3-thiazolidine-4-carbonylamino)phenyl]-2-methylpropionyloxy]milbemycin $A_4$
[Compound No. 3-73 (60%)]

Nuclear Magnetic Resonance Spectrum (CDCl$_3$, 200 MHz) δ ppm: 7.47 (2H, doublet, J=8.7 Hz), 7.26 (2H, doublet, J=8.7 Hz), 5.68–5.81 (2H, multiplet), 5.24–5.44 (5H, multiplet), 4.82–4.93 (2H, multiplet), 4.62–4.77 (3H, multiplet), 4.38–4.49 (1H, multiplet), 4.29 (1H, triplet, J=6.2 Hz), 4.07 (1H, singlet), 3.95 (1H, doublet, J=6.2 Hz).

EXAMPLE 77

13-[2-[4-(5-ketopyrrolidino-2-carbonylamino)phenyl]-2-methylpropionyloxy]milbemycin $A_4$
[Compound No. 3-76 (29%)]

Nuclear Magnetic Resonance Spectrum (CDCl$_3$, 200 MHz) δ ppm: 8.16 (1H, singlet), 7.52 (2H, doublet, J=8.7 Hz), 7.27 (2H, doublet, J=8.7 Hz), 6.79 (1H, singlet), 5.68–5.74 (2H, multiplet), 5.22–5.43 (4H, multiplet), 4.88 (1H, doublet, J=10.4 Hz), 4.65 (2H, broad singlet), 4.22–4.37 (2H, multiplet), 4.13 (1H, singlet), 3.94 (1H, doublet, J=6.2 Hz).

EXAMPLE 78

13-[2-[4-{2-(2-Chloroacetylaminothiazol-4-yl)-2-methoxyiminoacetylamino}phenyl]-2-methylpropionyloxy] milbemycin $A_4$
[Compound No. 3-77 (68%)]

Nuclear Magnetic Resonance Spectrum (CDCl$_3$, 200 MHz) δ ppm: 9.88 (1H, broad singlet), 7.93 (1H, singlet), 7.56 (2H, doublet, J=8.7 Hz), 7.53 (1H, singlet), 7.31 (2H, doublet, J=8.7 Hz), 5.69–5.87 (2H, multiplet), 5.22–5.45 (4H, multiplet), 4.90 (1H, doublet, J=10.5 Hz), 4.66 (2H, broad singlet), 4.29 (3H, broad singlet), 4.13 (3H, singlet), 4.10 (1H, singlet), 3.95 (1H, doublet, J=6.2 Hz).

EXAMPLE 79

13-[2-[4-{2-(2-Methoxycarbonylaminothiazol-4-yl)-2-methoxyimino}acetylaminophenyl]-2-methylpropionyloxy] milbemycin $A_4$
[Compound No. 3-78 (68%)]

Nuclear Magnetic Resonance Spectrum (CDCl$_3$, 200 MHz) δ ppm: 8.05 (1H, broad singlet), 7.57 (2H, doublet, J=8.5 Hz), 7.37 (1H, singlet), 7.30 (2H, doublet, J=8.5 Hz), 5.68–5.88 (2H, multiplet), 5.21–5.45 (4H, multiplet), 4.89 (1H, doublet, J=10.6 Hz), 4.66 (2H, broad singlet), 4.29 (1H, triplet, J=6.1 Hz), 4.09 (1H, singlet), 4.05 (3H, singlet), 3.95 (1H, doublet, J=6.1 Hz), 3.86 (3H, singlet).

EXAMPLE 80

13-[2-[4-(N-Methyl-N-methoxycarbonylaminoacetyl)aminophenoxy]-2-methylpropionyloxy]milbemycin $A_4$
[Compound No. 3-82 (56%)]

Nuclear Magnetic Resonance Spectrum (CDCl$_3$, 200 MHz) δ ppm: 7.97 (1H, broad singlet), 7.33 (2H, doublet, J=8.9 Hz), 6.76 (2H, doublet, J=8.9 Hz), 5.72–5.88 (2H, multiplet), 5.26–5.50 (4H, multiplet), 5.01 (1H, doublet, J=10.6 Hz), 4.68 (2H, broad singlet), 4.29 (1H, triplet, J=6.2 Hz), 4.07 (1H, singlet), 4.02 (2H, singlet), 3.96 (1H, doublet, J=6.2 Hz), 3.77 (3H, singlet).

EXAMPLE 81

13-[2-[4-{1-(Methoxycarbonylpyrrolidine)-2-carbonylamino}phenoxy]-2-methylpropionyloxy]milbemycin $A_4$
[Compound No. 3-83 (26%)]

Nuclear Magnetic Resonance Spectrum (CDCl$_3$, 200 MHz) δ ppm: 9.00 (1H, broad singlet), 7.35 (2H, doublet, J=8.9 Hz), 6.75 (2H, doublet, J=8.9 Hz), 5.71–5.90 (2H, multiplet), 5.26–5.51 (4H, multiplet), 5.01 (1H, doublet, J=10.6 Hz), 4.68 (2H, broad singlet), 4.44 (1H, broad singlet), 4.29 (1H, triplet, J=6.2 Hz), 4.07 (1H, singlet), 3.96 (1H, doublet, J=6.2 Hz), 3.77 (3H, singlet).

PREPARATION 1

α-Methoxyiminophenylacetic acid
(a) Ethyl α-methoxyiminophenylacetate 1.4 g (16.8 mmol) of O-methylhydroxylamine hydrochloride and 1.16 g (8.4 mmol) of potassium carbonate were added to a solution of 0.50 g (2.8 mmol) of ethyl phenylglyoxylate in N,N-dimethylformamide, and the resulting mixture was stirred at 90° C. for 4 hours. At the end of this time, the reaction mixture was poured into water and extracted with ethyl acetate. The extract was washed with a saturated aqueous solution of sodium chloride and dried over anhydrous magnesium sulfate, and the solvent was distilled off. The residue was purified by column chromatography through silica gel, eluted with a stepwise gradient of ethyl acetate (10–30%) in hexane, to give 0.47 g (67% yield) of the less polar isomer of the title compound and 0.13 g (19% yield) of the more polar isomer of the title compound.

Less polar isomer: Nuclear Magnetic Resonance Spectrum (CDCl$_3$, 200 MHz) δ ppm: 7.55–7.64 (2H, multiplet), 7.32–7.46 (3H, multiplet), 4.43 (2H, quartet, J=7.2 Hz), 4.02 (3H, singlet), 1.38 (3H, triplet, J=7.2 Hz).

More polar isomer: Nuclear Magnetic Resonance Spectrum (CDCl$_3$, 200 MHz) δ ppm: 7.42 (5H, singlet), 4.37 (2H, quartet, J=7.1 Hz), 4.06 (3H, singlet), 1.36 (3H, triplet, J=7.1 Hz).

(b) α-Methoxyiminophenylacetic acid

An aqueous solution of 0.90 g (22.6 mmol) of sodium hydroxide was added to a solution in methanol of 0.47 g (2.3 mmol) of ethyl α-methoxyiminophenylacetate (the less polar isomer prepared above). The resulting mixture was stirred overnight at room temperature. The reaction mixture was poured into 1N hydrochloric acid and extracted with ethyl acetate. The extract was dried over anhydrous magnesium sulfate and concentrated to give the title compound as a crude product, which was used in the subsequent reaction without further purification.

Nuclear Magnetic Resonance Spectrum (CDCl$_3$, 200 MHz) δ ppm: 10.3 (1H, broad singlet) 7.60–7.72 (2H, multiplet), 7.32–7.45 (3H, multiplet), 4.03 (3H, singlet).

PREPARATION 2

α-Methoxyimino-2-chlorophenylacetic acid
(a) 1-(2-Chlorophenyl)-1,2-ethanediol-2-O-t-butyldimethylsilyl ether First 1.63 g (20.0 mmol) of imidazole and then 1.63 g (24 mmol) of t-butyldimethylsilyl chloride were added, with ice-cooling, to a solution of 3.45 g (20 mmol) of 1-(2-chlorophenyl)-1,2-ethanediol in N,N-dimethylformamide. The resulting mixture was stirred at room temperature for 20 minutes. At the end of this time, the reaction mixture was poured into water and extracted three times with 50 ml portions of ethyl acetate. The combined extracts were washed with a saturated aqueous solution of sodium chloride and dried over anhydrous magnesium sulfate. The solvent was distilled off and the residue was purified by column chromatography through silica gel, eluted with a stepwise gradient of ethyl acetate (10–20%) in hexane, to to give 3.58 g (63% yield) of the title compound.

Nuclear Magnetic Resonance Spectrum (CDCl$_3$, 200 MHz) δ ppm: 7.58–7.66 (1H, multiplet), 7.16–7.35 (3H, multiplet), 5.16 (1H, doublet of triplets, J$_d$=8.0 Hz, J$_t$=3.0 Hz), 3.94 (1H, doublet of doublets, J=10.2, 3.0 Hz), 3.46 (1H, doublet of doublets, J=8.0, 3.0 Hz), 3.06 (1H, doublet, J=3.0 Hz), 0.91 (9H, singlet), 0.07 (3H, singlet), 0.05 (3H, singlet).

(b) 2'-chloro-2-t-butyldimethylsilyloxyacetophenone 70.0 g of manganese dioxide were added to a solution of 3.5 g (12.3 mmol) of 1-(2-chlorophenyl)-1,2-ethanediol-2-O-t-butyldimethylsilyl ether in dichloromethane. The resulting mixture was stirred at room temperature for 4 hours and the reaction mixture was then filtered through diatomaceous earth filter aid. The filtrate was concentrated to give 3.05 g (87%) of 2'-chloro-2-t-butyldimethylsilyloxyacetophenone as a crude product.

Nuclear Magnetic Resonance Spectrum (CDCl$_3$, 200 MHz) δ ppm: 7.25–7.48 (4H, multiplet), 4.75 (2H, singlet), 0.87 (9H, singlet), 0.1 (6H, singlet).

(c) 2'-Chloro-2-hydroxyacetophenone O-methyloxime 1.78 g of O-methylhydroxylamine hydrochloride were added to a solution of the 3.05 g of 2'-chloro-2-t-butyldimethyl silyloxyacetophenone prepared above in a mixture of methanol, water and 1,4-dioxane. The resulting mixture was stirred at room temperature for 14 hours, and the reaction mixture was then poured into water and extracted three times with 50 ml portions of ethyl acetate. The combined extracts were washed with a saturated aqueous solution of sodium chloride and dried over anhydrous magnesium sulfate, the solvent was distilled off, and the residue was purified by column chromatography through silica gel, eluted with a stepwise gradient of ethyl acetate (10–40%) in hexane, to give 691 mg (32.4% yield) of the less polar isomer of 2'-chloro-2-hydroxyacetophenone O-methyloxime compound and 370 mg (17.3% yield) of the more polar isomer of the title compound.

Less polar isomer: Nuclear Magnetic Resonance Spectrum (CDCl$_3$, 200 MHz) δ ppm: 7.29–7.46 (4H, multiplet), 4.69 (2H, doublet, J=7.2 Hz), 4.02 (3H, singlet).

More polar isomer: Nuclear Magnetic Resonance Spectrum (CDCl$_3$, 200 MHz) δ ppm: 7.41–7.47 (1H, multiplet), 7.29–7.38 (1H, multiplet), 7.14–7.20 (1H, multiplet), 4.45 (2H, doublet, J=5.5. Hz), 3.89 (3H, singlet).

(d) α-Methoxyimino-2-chlorophenylacetic acid 10 ml of Jones reagent (chromic anhydride in dilute sulfuric acid) were added to a solution in acetone of 0.40 g of 2'-chloro-2-hydroxyacetophenone O-methyloxime (the less polar isomer prepared above). The resulting mixture was stirred at room temperature for an hour and then 10 ml of isopropanol were added to it with ice-cooling. The reaction mixture was poured into 100 ml of water and extracted three times with 10 ml portions of ethyl acetate. The combined extracts were washed with a saturated aqueous solution of sodium chloride and dried over magnesium sulfate. The solvent was distilled off to give 320 mg (75%) of the title compound as a crude product.

Nuclear Magnetic Resonance Spectrum (CDCl$_3$, 200 MHz) δ ppm: 7.28–7.50 (4H, multiplet), 5.25 (1H, broad singlet), 4.14 (3H, singlet).

PREPARATION 3

2-Hydroxyacetophenone O-alkyloxime derivatives

The following 2-hydroxyacetophenone O-alkyloxime derivatives substituted on the phenyl group were prepared by procedures corresponding to those used in Preparation 2 above for producing 2'-chloro-2-hydroxy-acetophenone O-methyloxime.

(1) 2-Hydroxyacetophenone O-methyloxime

Nuclear Magnetic Resonance Spectrum (CDCl$_3$, 200 MHz) δ ppm: 7.60–7.69 (2H, multiplet), 7.34–7.43 (3H, multiplet), 4.69 (2H, doublet, J=7.0 Hz), 4.04 (3H, singlet), 2.73 (1H, triplet, J=7.0 Hz).

(2) 3'-Fluoro-2-hydroxyacetophenone O-methyloxime

Nuclear Magnetic Resonance Spectrum (CDCl$_3$, 200 MHz) δ ppm: 7.30–7.45 (3H, multiplet), 7.01–7.12 (1H, multiplet), 4.68 (2H, doublet, J=6.9 Hz), 4.04 (3H, singlet), 2.65 (1H, triplet, J=6.9 Hz).

(3) 3'-Chloro-2-hydroxyacetophenone O-methyloxime

Nuclear Magnetic Resonance Spectrum (CDCl$_3$, 200 MHz) δ ppm: 7.67 (1H, multiplet), 7.49–7.56 (1H, multiplet), 7.31–7.40 (2H, multiplet), 4.66 (1H, doublet, J=6.9 Hz), 4.05 (3H, singlet), 2.60 (1H, triplet, J=6.9 Hz).

PREPARATION 4

α-Methoxyimino-2-chlorophenylacetic acid derivatives

The following α-methoxyiminophenylacetic acid derivatives substituted on the phenyl group were prepared by procedures corresponding to those used in Preparation 2 above for producing α-methoxyimino-2-chlorophenylacetic acid.

(1) α-Methoxyimino-3-fluorophenylacetic acid

Nuclear Magnetic Resonance Spectrum (CDCl$_3$, 200 MHz) δ ppm: 9.40 (1H, broad singlet), 7.76–7.97 (1H, multiplet), 7.15–7.58 (3H, multiplet), 4.07 (3H, singlet), 3.89 (3H, singlet).

(2) α-Methoxyimino-3-chlorophenylacetic acid

Nuclear Magnetic Resonance Spectrum (CDCl$_3$, 200 MHz) δ ppm: 7.94–8.10 (1H, multiplet), 7.25–7.70 (3H, multiplet), 4.09 (3H, singlet).

(3) α-Methoxyimino-4-chlorophenylacetic acid

Less polar isomer: Nuclear Magnetic Resonance Spectrum (CDCl$_3$, 200 MHz) δ ppm: 7.59 (2H, doublet, J=8.71 Hz), 7.38 (2H, doublet, J=8.71 Hz), 4.10 (3H, singlet).

More polar isomer: Nuclear Magnetic Resonance Spectrum (CDCl$_3$, 200 MHz) δ ppm: 7.50 (2H, doublet, J=8.91 Hz), 7.42 (2H, doublet, J=8.91 Hz), 4.12 (3H, singlet).

(4) α-Ethoxyimino-4-chlorophonylacetic acid

Less polar isomer: Nuclear Magnetic Resonance Spectrum (CDCl$_3$, 200 MHz) δ ppm: 7.69 (2H, doublet, J=9.0 Hz), 7.39 (2H, doublet, J=9.0 Hz), 4.36 (2H, quartet, J=7.6 Hz), 1.38 (3H, triplet, J=7.6 Hz).

More polar isomer: Nuclear Magnetic Resonance Spectrum (CDCl$_3$, 200 MHz) δ ppm: 7.54 (2H, doublet, J=6.6 Hz), 7.47 (2H, doublet, J=6.6 Hz), 4.37 (2H, quartet, J=7.0 Hz), 1.37 (3H, triplet, J=7.0 Hz).

(5) α-Methoxyimino-2-methoxyphenylacetic acid

Nuclear Magnetic Resonance Spectrum (CDCl$_3$, 200 MHz) δ ppm: 7.65 (1H, doublet of doublets, J=1.6, 7.7 Hz), 7.41 (1H, triplet of triplets, J=1.6, 8.0 Hz), 6.80–7.05 (2H, multiplet), 4.07 (3H, singlet), 3.82 (3H, singlet).

(6) α-Methoxyimino-2-ethoxyphenylacetic acid

Less polar isomer: Nuclear Magnetic Resonance Spectrum (CDCl$_3$, 200 MHz) δ ppm: 7.62 (1H, doublet of doublets, J=1.7, 7.7 Hz), 7.39 (1H, doublet of triplets, J=1.0, 7.0 Hz), 6.85–8.01 (2H, multiplet), 4.08 (3H, singlet), 4.0–4.13 (2H, multiplet), 1.40 (3H, triplet, J=7.0 Hz).

More polar isomer: Nuclear Magnetic Resonance Spectrum (CDCl$_3$, 200 MHz) δ ppm: 7.25–7.40 (2H, multiplet), 6.88–7.05 (2H, multiplet), 4.08 (3H, singlet), 4.0–4.13 (2H, multiplet), 1.33 (3H, triplet, J=7.0 Hz).

(7) α-Methoxyimino-2-benzyloxyphenylacetic acid

Nuclear Magnetic Resonance Spectrum (CDCl$_3$, 200 MHz) δ ppm: 8.70 (1H, broad singlet), 7.25–7.42 (7H, multiplet), 7.06 (2H, doublet, J=8.3 Hz), 6.99 (2H, doublet, J=8.3 Hz), 5.08 (2H, singlet), 4.04 (3H, singlet).

PREPARATION 5

3-Methoxyimino-3-phenylpropionic acid

The title compound was prepared by following the procedure for producing α-methoxyiminophenylacetic acid described in Preparation 1, but using ethyl benzoylacetate as starting material.

Nuclear Magnetic Resonance Spectrum (CDCl$_3$, 200 MHz) δ ppm: 7.60–7.71 (2H, multiplet), 7.34–7.45 (3H, multiplet), 4.03 (3H, singlet), 3.81 (2H, singlet).

PREPARATION 6

α-Methoxyimino 4-nitrophenylacetic acid

The title compound was prepared by following the procedure for producing α-methoxyiminophenylacetic acid described in Preparation 1, but using ethyl 4-nitrophenylglyoxylate, reported in Synthesis, 850 (1990), as starting material.

Nuclear Magnetic Resonance Spectrum (CDCl$_3$, 200 MHz) δ ppm: 8.13 (2H, doublet, J=7.0 Hz), 7.48 (2H, doublet, J=7.0 Hz), 3.95 (3H, singlet).

PREPARATION 7

α-Methoxyimino-2-hydroxyphenylacetic acid

The title compound was prepared by following the procedure for producing α-methoxyiminophenylacetic acid described in Preparation 1, but using ethyl 2-hydroxyphenylglyoxylate as starting material.

Nuclear Magnetic Resonance Spectrum (CDCl$_3$, 200 MHz) δ ppm: 7.17–7.38 (2H, multiplet), 6.81–7.08 (2H, multiplet), 4.08 (3H, singlet).

PREPARATION 8

α-Methoxyimino-2-pyridylacetic acid

The title compound was prepared by following the procedure for producing α-methoxyiminophenylacetic acid described in Preparation 1, but using commercially available ethyl 2-pyridylglyoxylate as a starting material.

Nuclear Magnetic Resonance Spectrum (CDCl$_3$, 200 MHz) δ ppm: 8.50 (1H, doublet, J=4.9 Hz), 7.75 (1H, doublet of triplets, $J_d$=1.6 Hz, $J_t$=7.7 Hz), 7.61 (1H, doublet of triplets, $J_d$=7.7 Hz, $J_t$=1.6 Hz), 7.28 (1H, triplet, J=7.7 Hz), 4.38 (1H, broad singlet), 3.97 (3H, singlet).

PREPARATION 9

α-Methoxyimino-4-nitrophenylacetic acid
(a) Ethyl α-methoxyimino-4-nitrophenyl acetate 0.95 g (11.4 mmol) of O-methylhydroxylamine hydrochloride was added to a solution of 1.18 g (5.7 mmol) of ethyl 4-nitrophenylglyoxylate [prepared by the procedure described in Synthesis 850 (1990)] in dimethyl formamide, and the resulting mixture was stirred at room temperature for 24 hours. At the end of this time, the reaction mixture was poured into water and extracted with ethyl acetate. The extract was washed with a saturated aqueous solution of sodium chloride and dried over anhydrous magnesium sulfate. The solvent was distilled off. The residue was purified by column chromatography through silica gel, eluted with a stepwise gradient of ethyl acetate (10–40%) in hexane, to give 0.40 g (30% yield) of the title compound.

Nuclear Magnetic Resonance Spectrum (CDCl$_3$, 200 MHz) δ ppm: 8.28 (2H, doublet, J=9.0 Hz), 7.58 (2H, doublet, J=9.0 Hz), 4.38 (2H, quartet, J=7.1 Hz), 4.09 (3H, singlet), 1.37 (3H, triplet, J=7.1 Hz).

(b) α-Methoxyimino-4-nitrophenylacetic acid 5 ml (10 mmol) of a 2N aqueous solution of sodium hydroxide were added to a solution of 1.28 g (5.07 mmol) of ethyl α-methoxyimino-4-nitrophenylacetate in methanol, and the resulting mixture was stirred overnight at room temperature. The reaction mixture was poured into 1N hydrochloric acid and extracted with ethyl acetate. The extract was dried over anhydrous magnesium sulfate and the solvent was distilled off to give 1.0 g (88% yield) of the title compound as a crude product, which was used in the following reaction without further purification.

Nuclear Magnetic Resonance Spectrum (CDCl$_3$, 200 MHz) δ ppm: 8.13 (2H, doublet, J=9.0 Hz), 7.48 (2H, doublet, J=9.0 Hz), 3.95 (3H, singlet).

PREPARATION 10

4'-Nitro-2-hydroxyacetophenone O-methyloxime
(a) 4-nitrophenylglygxyiic acid 3 ml (6 mmol) of a 2N aqueous solution of sodium hydroxide were added to a solution of 651 mg (2.92 mmol) of ethyl 4-nitrophenylglyoxylate in methanol, and the resulting mixture was stirred overnight at room temperature. The reaction mixture was poured into 2N hydrochloric acid and extracted with ethyl acetate. The extract was washed with a saturated aqueous solution of sodium chloride and dried over anhydrous magnesium sulfate. The solvent was distilled off, to give 0.8 g (quantitative yield) of 4-nitrophenylglyoxylic acid as a crude product.

(b) 1-(4-nitrophenyl)-1,2-ethanediol 7 ml of a 1.0M tetrahydrofuran solution of diborane-tetrahydrofuran complex were added, at 0° C. under a stream of nitrogen, to a solution of 0.5 g of crude 4-nitrophenylglyoxylic acid in tetrahydrofuran, and the resulting mixture was stirred overnight at room temperature. The reaction mixture was poured into ice-water and extracted with ethyl acetate. The extract was washed with a saturated aqueous solution of sodium chloride and dried over anhydrous magnesium sulfate. The solvent was distilled off, to give 0.56 g (quantitative yield) of 1-(4-nitrophenyl)-1,2-ethanediol as a crude product.

(c) 1-(4-nitrophenyl)-1,2-ethanediol 2O-t-butyldimethylsilyl ether

First 0.23 g of imidazole and then 0.50 g of t-butyldimethylsilyl chloride were added to a solution of 0.56 g of crude 1-(4-nitrophenyl)-1,2-ethanediol in dimethylformamide, while cooling with ice, and the resulting mixture was stirred at room temperature for 20 minutes. At the end of this time, the reaction mixture was poured into water and extracted three times with 50 ml portions of ethyl acetate. The combined extracts were washed with a saturated aqueous solution of sodium chloride and dried over anhydrous magnesium sulfate. The solvent was distilled off and the residue was purified by column chromatography through silica gel, eluted with a stepwise gradient of ethyl acetate (0–30%) in hexane, to give 0.58 g (63% yield) of 1-(4-nitrophenyl)-1,2-ethanediol 2-O-t-butyldimethylsilyl ether.

Nuclear Magnetic Resonance Spectrum (CDCl$_3$, 200 MHz) δ ppm: 8.22 (2H, doublet, J=8.7 Hz), 4.84 (1H, multiplet), 3.82 (1H, doublet of doublets, J=3.9, 10, 1 Hz), 3.54 (1H, doublet of doublets, J=7.9, 10, 1 Hz), 3.06 (1H, doublet, J=2.9 Hz), 0.91 (9H, singlet), 0.07 (6H, singlet), 0.05 (6H, singlet).

(d) 4'-nitro-3-t-butyldimethylsilyloxyacetophenone 3.5 g of manganese (IV) oxide were added to a solution of 0.41 g (1.36 mmol) of 1-(4-nitrophenyl)-1,2-ethanediol 2-O-t-butyldimethylsilyl ether in dichloromethane, and the resulting mixture was stirred for 4 hours at room temperature. The reaction mixture was then filtered through "Celite" (diatomaceous earth) and the filtrate was concentrated in vacuo. The residue was purified by silica gel column chromatography, eluted with a stepwise gradient of ethyl acetate (0–25%) in hexane, to give 0.16 g (40% yield) of 4'-nitro-2-t-butyldimethylsilyloxyacetophenone.

Nuclear Magnetic Resonance Spectrum (CDCl$_3$, 200 MHz) δ ppm: 8.32 (2H, doublet, J=9.0 Hz), 8.11 (2H, doublet, J=9.0 Hz), 4.88 (2H, singlet), 0.91 (9H, singlet), 0.12 (6H, singlet).

(e) 4'-Nitro-2-hydroxyacetophenone O-methyloxime 69 mg of O-methylhydroxylamine hydrochloride were added to a solution of 0.12 g (0.41 mmol) of 4'-nitro-2-t-butyldimethylsilyloxyacetophenone (obtained above) in a mixture of methanol (1.2 ml), 1,4-dioxane (2.0 ml) and water (2.0 ml). The resulting mixture was stirred for 1.5 hours at 80° C., then poured into water and extracted with ethyl acetate. The extract was washed with a saturated aqueous solution of sodium chloride and dried over anhydrous magnesium sulfate. The residue was purified by silica gel column chromatography, eluted with a stepwise gradient of ethyl acetate (10–40%) in hexane, to give 58 mg (67% yield) of the title compound.

Nuclear Magnetic Resonance Spectrum (CDCl$_3$, 200 MHz) δ ppm: 8.25 (2H, doublet, J=8.9 Hz), 7.85 (2H, doublet, J=8.9 Hz), 4.73 (2H, doublet, J=6.6 Hz), 4.09 (3H, singlet), 2.44 (1H, triplet, J=6.6 Hz).

PREPARATION 11

(Step A)

13-[2-methoxyimino-2-(4-nitrophenyl)ethoxy]-5-keto-milbemycin A$_4$ 0.13 ml of trifluoromethanesulfonic acid was added, under a stream of argon and with ice-cooling, to a solution of 821 mg (1.5 mmol) of 15-hydroxy-5-ketomilbemycin A$_4$, 1.08 g (5.16 mmol) of 2-methoxyimino-2-(4-nitrophenyl)ethanol and 571 mg of copper (I) iodide in 10 ml of dichloromethane, and the resulting mixture was stirred at room temperature for an hour. The reaction mixture was then poured into water and extracted with ethyl acetate. The extract was washed first with a 5% aqueous solution of sodium bicarbonate and then with a saturated aqueous solution of sodium chloride, dried over anhydrous magnesium sulfate, and concentrated in vacuo to give 824 mg of the crude title compound, which was used in the subsequent reaction without further purification.

(Step B)

13-[2-methoxyimino-2-(4-nitrophenyl)ethoxy]milbemycin A$_4$ 200 mg (1.01 mmol) of sodium borohydride were added, with ice-cooling, to a solution of 824 mg (1.01 mmol) of crude 13-[2-methoxyimino-2-(4-nitrophenyl)ethoxy]-5-ketomilbemycin A$_4$ in 40 ml of methanol, and the resulting mixture was stirred at 0° C. for 30 minutes. The reaction mixture was then poured into water and extracted with ethyl acetate. The extract was washed first with water and then with a saturated aqueous solution of sodium chloride, dried over anhydrous magnesium sulfate, and concentrated in vacuo to give 720 mg of the crude title compound, which was used in the subsequent reaction without further purification.

(Step C)

13-[2-methoxyimino-2-(4-aminophenyl)ethoxy]milbemycin A$_4$ 130 mg of zinc powder were added, at room temperature, to a solution of 150 mg (0.20 mmol) of crude 13-[2-methoxyimino-2-(4-nitrophenyl)ethoxy]milbemycin A$_4$ in 40 ml of 90% acetic acid, and the resulting mixture was stirred for 30 minutes. The reaction mixture was then mixed with ethyl acetate and insolubles were filtered off. The filtrate was diluted with water then extracted with ethyl acetate. The extract was washed with a 4% aqueous solution of sodium bicarbonate and dried over anhydrous magnesium sulfate, the solvent was distilled off, and the residue was purified by preparative high performance liquid chromatography [column YMC ODS (10 μm), 250×20 mm ID; eluted with MeOH-H$_2$O (6:1), 10 ml/min; UV-detection (240 nm)] to give 40 mg (28% yield) of the title compound.

Nuclear Magnetic Resonance Spectrum (CDCl$_3$, 200 MHz) δ ppm: 7.48 (2H, doublet, J=8.7 Hz), 6.64 (2H, doublet, J=8.7 Hz), 5.64–5.79 (2H, multiplet), 5.15–5.44 (4H, multiplet), 4.68 (2H, singlet), 4.40 (2H, singlet), 4.29 (1H, triplet, J=5.7 Hz), 3.98 (1H, doublet, J=5.7 Hz), 3.94 (3H, singlet).

The product made by this method was used as starting material for the acylation step D in the above Examples 32 and 33.

AGROCHEMICAL FORMULATIONS

Where the compounds of the invention are intended for agricultural or horticultural use, a variety of forms and formulations is possible, and these are exemplified in the following Formulation Examples. In these, the compound of the invention which is used is each one in turn of the individual compounds listed in Tables 4 to 12 below. All percentages are by weight, and the compounds of the present invention are identified by the numbers assigned to them in the above Tables 1 to 3.

FORMULATION EXAMPLE 1

Wettable Powder

A mixture comprising 10% of the compound of the invention (identified in Tables 4 to 12), 2.5% of sodium dodecylbenzenesulfonate, 2.5% of sodium ligninesulfonate and 85% of diatomaceous earth was thoroughly mixed and pulverized to make a wettable powder.

FORMULATION EXAMPLE 2

Emulsifiable concentrate

A mixture of 5% of the compound of the invention (identified in Tables 4 to 12), 10% of "Sorpol SM 100", (trade name for an emulsifier, product of Toho Chemical Co., Ltd.) and 85% of xylene was thoroughly mixed to make an emulsifiable concentrate.

FORMULATION EXAMPLE 3

Granules

A mixture comprising 3% of the compound of the invention (identified in Tables 4 to 12), 1% of "White carbon" (trade name for a silicon dioxide dehydrating agent), 5% of sodium lignin sulfonate and 91% of clay was thoroughly mixed and pulverized, kneaded well with water, and then granulated and dried to make granules.

FORMULATION EXAMPLE 4

Emulsifiable Concentrate 2.5% of the compound of the invention (identified in Tables 4 to 12), and 1.0% of BHT (an antioxidant) were dissolved in 26.5% of cyclohexanone. The solution was mixed with 50.0% of "Sylgard 309" (a silicone surfactant from Dow Corning) and 20.0% of "Excepal" (a coconut fatty acid methyl ester from Kao Co., Ltd.) and homogeneously dissolved to make an emulsifiable concentrate.

BIOLOGICAL ACTIVITY

The activity of the compounds of the invention is further illustrated by the following biological assays, for which the results are reported in Tables 4 to 12. The compounds of the invention are identified by the numbers used in the above Tables 1 to 3. Compounds (C1) to (C10) are used as controls, for purposes of comparison, and their formulae are shown below. Compounds (C1) to (C4) and (C6) to (C10) have been disclosed in European Patent Publication 246 739, and Compound (C5) has been disclosed in European Patent Publication 357 460.

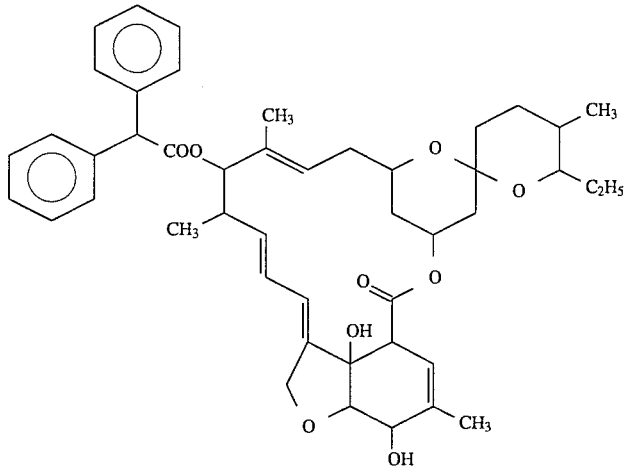

(Control Compound No. 1)

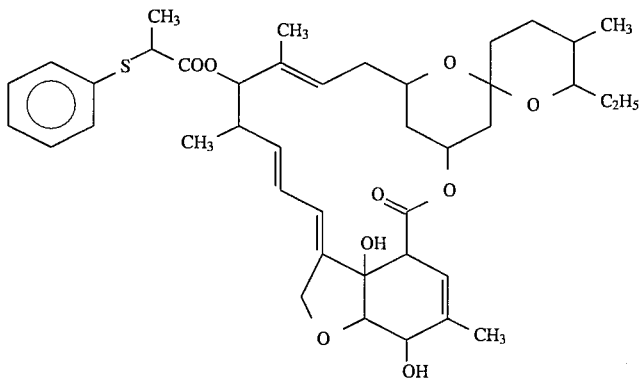

(Control Compound No. 2)

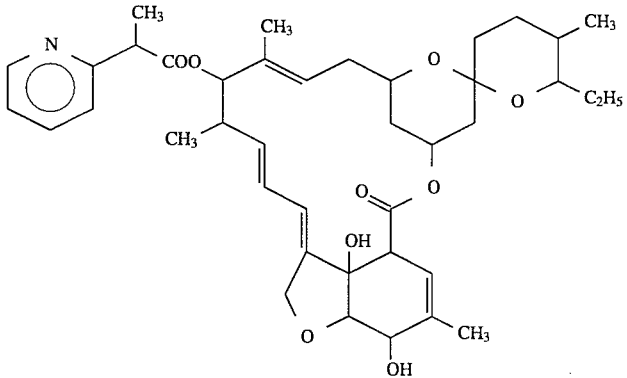

(Control Compound No. 3)

-continued
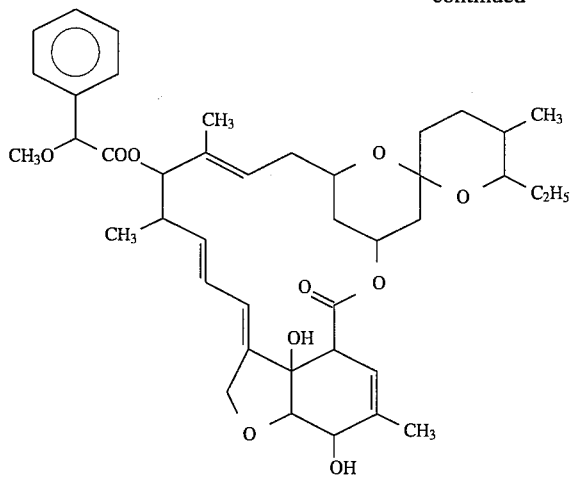
(Control Compound No. 4)
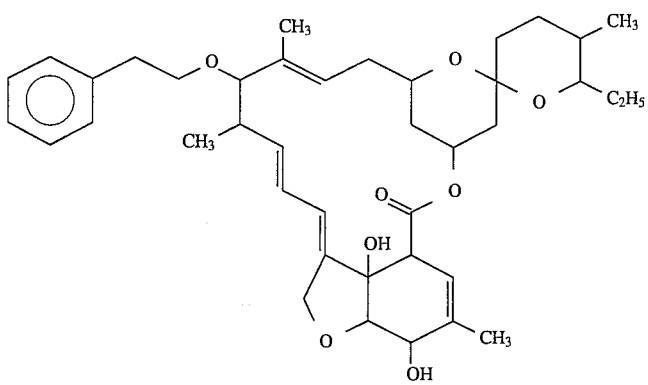
(Control Compound No. 5)
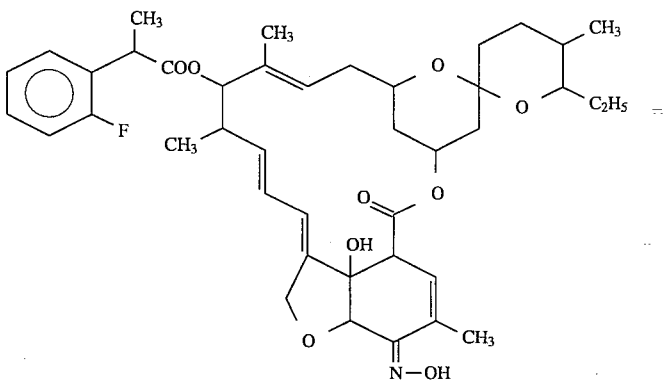
(Control Compound No. 6)
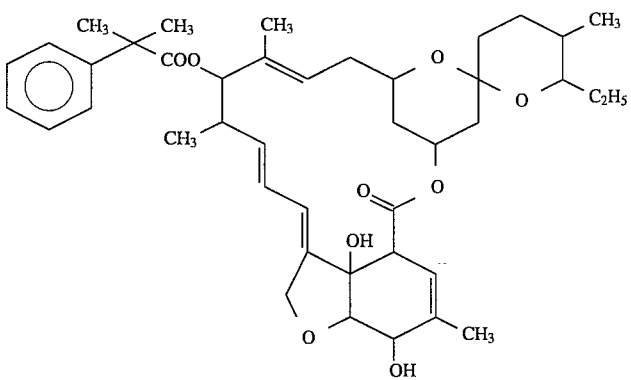
(Control Compound No. 7)

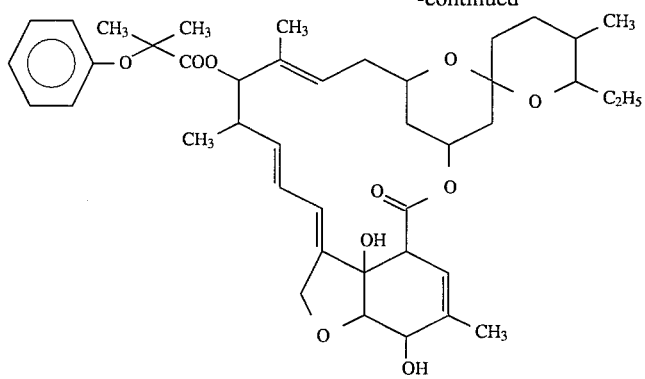

(Control Compound No. 8)

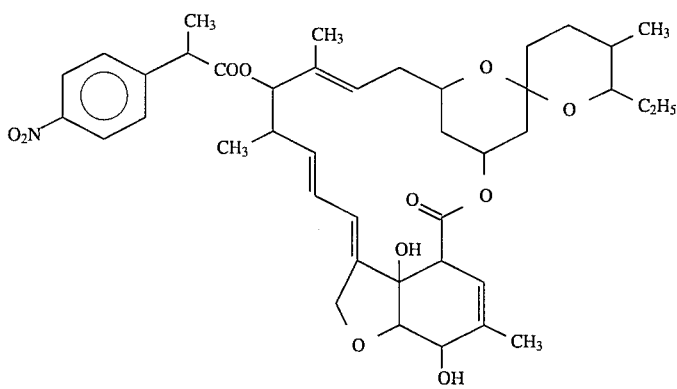

(Control Compound No. 9)

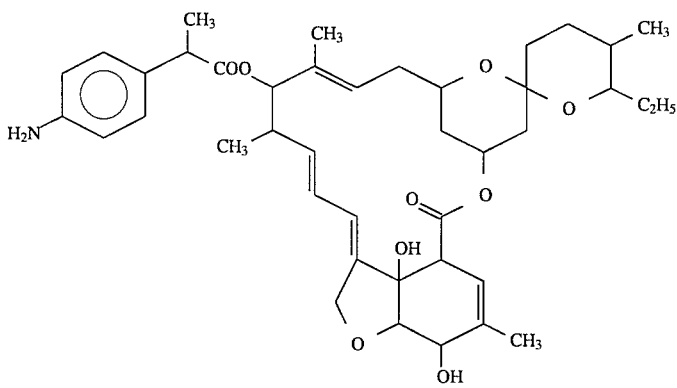

(Control Compound No. 10)

EXPERIMENT 1

Insecticidal Activity Against the Cabbage Moth

Emulsifiable concentrates, prepared as described in Formulation Example 2 and containing 1% of the active ingredient, were diluted with water to bring the final concentration to 1 ppm. Cabbage leaves were immersed in the resulting mixtures for 10 seconds and then air-dried, after which each leaf was placed in a polyethylene cup having a diameter of 8 cm. Ten third-instar larvae of the cabbage moth were put into each cup, which was then capped. The cups were allowed to stand at a thermostatically controlled temperature of 25° C. for 3 days, after which the percentage mortality (including symptoms of distress) was determined. Each test was carried out in duplicate in parallel. The results are shown in Tables 4 to 6, in which the compounds of the invention are identified by the numbers assigned to them in the foregoing Tables 1 to 3.

TABLE 4

| Compound No. | Mortality (%) | Compound No. | Mortality (%) |
|---|---|---|---|
| 1-12 | 100 | 1-91 | 100 |
| 1-72 | 100 | 1-92 | 100 |
| 1-73 | 100 | 1-93 | 100 |
| 1-74 | 100 | 1-98 | 100 |
| 1-75 | 100 | 1-102 | 100 |
| 1-77 | 100 | 1-107 | 100 |
| 1-78 | 100 | 1-111 | 100 |
| 1-79 | 100 | 1-204 | 100 |
| 1-80 | 95 | Control (C1) | 50 |
| 1-81 | 100 | Control (C2) | 20 |
| 1-83 | 100 | Control (C3) | 0 |
| 1-89 | 100 | Control (C4) | 70 |
| 1-90 | 100 | Control (C5) | 65 |
| | | Control (C6) | 0 |

TABLE 5

| Compound No. | Mortality (%) | Compound No. | Mortality (%) |
|---|---|---|---|
| 2-7 | 100 | | |
| 2-16 | 100 | Control (C1) | 50 |
| 2-22 | 100 | Control (C2) | 20 |
| 2-39 | 100 | Control (C3) | 0 |
| 2-43 | 100 | Control (C4) | 70 |
| 2-45 | 100 | Control (C5) | 65 |
| 2-106 | 100 | | |

TABLE 6

| Compound No. | Mortality (%) | Compound No. | Mortality (%) |
|---|---|---|---|
| 3-1 | 100 | 3-56 | 100 |
| 3-3 | 100 | 3-58 | 100 |
| 3-11 | 100 | 3-61 | 100 |
| 3-19 | 100 | 3-62 | 100 |
| 3-26 | 100 | 3-64 | 100 |
| 3-27 | 100 | 3-65 | 100 |
| 3-28 | 100 | 3-66 | 100 |
| 3-29 | 100 | 3-68 | 100 |
| 3-33 | 100 | 3-69 | 100 |
| 3-34 | 100 | 3-71 | 100 |
| 3-36 | 100 | 3-72 | 100 |
| 3-37 | 100 | 3-76 | 100 |
| 3-38 | 100 | 3-78 | 100 |
| 3-39 | 100 | 3-82 | 100 |
| 3-40 | 100 | 3-83 | 100 |
| 3-42 | 100 | | |
| 3-43 | 100 | Control (C7) | 10 |
| 3-46 | 100 | Control (C8) | 20 |
| 3-47 | 100 | Control (C9) | 30 |
| 3-48 | 100 | Control (C10) | 10 |
| 3-49 | 100 | | |

EXPERIMENT 2

Insecticidal Activity Against the Common Cutworm

Emulsifiable concentrates, prepared as described in Formulation Example 2 and containing 1% of the active ingredient, were diluted with water to bring the final concentration to 10 ppm. 5 g of an artificial feed ("Insecta L") were immersed in each of the resulting mixtures for 20 seconds, and the feed was then air-dried. It was then placed in a polyethylene cup having a diameter of 8 cm. Ten third-instar larvae of the common cutworm were put into each cup, which was then capped. The cups were allowed to stand at a thermostatically controlled temperature of 25° C. for 3 days, after which the percentage mortality (including symptoms of distress) was determined. Each test was carried out in duplicate in parallel. The results are shown in Tables 7 to 9.

TABLE 7

| Compound No. | Mortality (%) | Compound No. | Mortality (%) |
|---|---|---|---|
| 1-11 | 100 | 1-90 | 100 |
| 1-12 | 100 | 1-91 | 100 |
| 1-38 | 100 | 1-92 | 100 |
| 1-70 | 85 | 1-93 | 100 |
| 1-72 | 100 | 1-98 | 85 |
| 1-73 | 100 | 1-102 | 100 |
| 1-74 | 100 | 1-111 | 100 |
| 1-75 | 100 | 1-186 | 100 |
| 1-77 | 100 | | |
| 1-78 | 100 | Control (C1) | 55 |

TABLE 7-continued

| Compound No. | Mortality (%) | Compound No. | Mortality (%) |
|---|---|---|---|
| 1-79 | 95 | Control (C2) | 10 |
| 1-80 | 100 | Control (C3) | 10 |
| 1-81 | 100 | Control (C4) | 60 |
| 1-83 | 100 | Control (C6) | 0 |
| 1-89 | 100 | | |

TABLE 8

| Compound No. | Mortality (%) | Compound No. | Mortality (%) |
|---|---|---|---|
| 2-7 | 100 | | |
| 2-16 | 100 | Control (C1) | 55 |
| 2-22 | 100 | Control (C2) | 10 |
| 2-45 | 100 | Control (C3) | 10 |
| | | Control (C4) | 60 |

TABLE 9

| Compound No. | Mortality (%) | Compound No. | Mortality (%) |
|---|---|---|---|
| 3-1 | 90 | 3-47 | 100 |
| 3-26 | 100 | 3-48 | 100 |
| 3-27 | 100 | 3-49 | 100 |
| 3-33 | 100 | 3-56 | 100 |
| 3-34 | 100 | 3-61 | 100 |
| 3-36 | 100 | 3-66 | 100 |
| 3-37 | 100 | | |
| 3-39 | 100 | Control (C7) | 0 |
| 3-42 | 100 | Control (C8) | 10 |
| 3-43 | 100 | Control (C9) | 10 |
| 3-46 | 100 | Control (C10) | 20 |

EXPERIMENT 3

Insecticidal Activity Against the Oriental Tea Tortrix Moth

Emulsifiable concentrates, prepared as described in Formulation Example 2 and containing 1% of the active ingredient, were diluted with water to bring the final concentration to 10 ppm. 5 g of an artificial feed ("Insecta L") were immersed in each of the resulting mixtures for 20 seconds, and the feed was then air-dried. It was then placed in a polyethylene cup having a diameter of 8 cm. Ten fourth-instar larvae of the oriental tea tortrix moth were put into each cup, which was then capped. The cups were allowed to stand at a thermostatically controlled temperature of 25° C. for 3 days, after which the percentage mortality (including symptoms of distress) was determined. Each test was carried out in duplicate in parallel. The results are shown in Tables 10 to 12.

TABLE 10

| Compound No. | Mortality (%) | Compound No. | Mortality (%) |
|---|---|---|---|
| 1-12 | 90 | 1-90 | 100 |
| 1-70 | 85 | 1-91 | 100 |
| 1-72 | 100 | 1-92 | 100 |
| 1-73 | 100 | 1-93 | 100 |
| 1-74 | 100 | 1-98 | 95 |
| 1-75 | 100 | 1-102 | 100 |
| 1-76 | 100 | 1-186 | 100 |
| 1-77 | 100 | | |

TABLE 10-continued

| Compound No. | Mortality (%) | Compound No. | Mortality (%) |
|---|---|---|---|
| 1-78 | 100 | Control (C1) | 60 |
| 1-79 | 95 | Control (C2) | 10 |
| 1-80 | 95 | Control (C3) | 0 |
| 1-81 | 100 | Control (C4) | 65 |
| 1-83 | 100 | | |
| 1-89 | 100 | | |

TABLE 11

| Compound No. | Mortality (%) | Compound No. | Mortality (%) |
|---|---|---|---|
| 2-16 | 100 | | |
| 2-22 | 100 | Control (C1) | 60 |
| 2-39 | 100 | Control (C2) | 10 |
| 2-43 | 100 | Control (C3) | 0 |
| 2-45 | 100 | Control (C4) | 65 |

TABLE 12

| Compound No. | Mortality (%) | Compound No. | Mortality (%) |
|---|---|---|---|
| 3-1 | 90 | 3-47 | 100 |
| 3-11 | 100 | 3-48 | 100 |
| 3-26 | 100 | 3-49 | 100 |
| 3-27 | 100 | 3-56 | 100 |
| 3-29 | 100 | 3-61 | 100 |
| 3-33 | 100 | 3-66 | 100 |
| 3-34 | 100 | 3-68 | 100 |
| 3-36 | 100 | 3-69 | 100 |
| 3-37 | 100 | 3-76 | 100 |
| 3-38 | 100 | | |
| 3-39 | 100 | Control (C7) | 0 |
| 3-42 | 100 | Control (C8) | 10 |
| 3-43 | 100 | Control (C9) | 10 |
| 3-46 | 100 | Control (C10) | 20 |

We claim:

1. A compound having the formula (I):

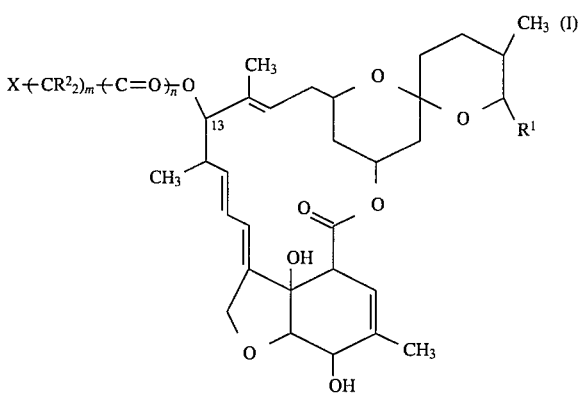

wherein:

$R^1$ represents a methyl, ethyl, isopropyl or sec-butyl group;

$R^2$ represents a hydrogen atom or an alkyl group having from 1 to 3 carbon atoms;

X represents:

(a) a group having the formula (II):

wherein:

$R^3$ represents a hydrogen atom, or an alkyl group having from 1 to 4 carbon atoms; and Y represents an aryl group having from 6 to 10 carbon atoms or a heterocyclyl group, said aryl group and said heterocyclyl group being unsubstituted or substituted with 1 or 2 substituents, which are the same or different, selected from the Substituents A below;

or X represents:

(b) a group having the formula (III):

wherein:

p=0 or 1; and

Z represents:

an alkanoyl group having from 2 to 3 carbon atoms;

an alkylsulfonyl group having from 1 to 3 carbon atoms;

an alkoxycarbonyl group having from 2 to 5 carbon atoms;

an aminoalkanoyl group having from 2 to 7 carbon atoms, the amino moiety of said aminoalkanoyl group being unsubstituted or substituted by 1 or 2 subtituents, which are the same or different, selected from the Substituents B below, and the alkanoyl moiety of said aminoalkanoyl group being unsubstituted or substituted by a phenyl group or by an alkylthio group having from 1 to 3 carbon atoms;

Substituents A comprise:

a halogen atom;

a nitro group;

a hydroxy group;

an alkoxy group having from 1 to 4 carbon atoms;

an aralkyloxy group having from 7 to 11 carbon atoms;

an amino group;

an alkanoylamino group having from 1 to 4 carbon atoms;

a haloalkanoylamino group having from 2 to 4 carbon atoms;

an alkylsulfonylamino group having from 1 to 3 carbon atoms;

an alkoxycarbonylamino group having from 2 to 5 carbon atoms;

a haloalkoxycarbonylamino group having from 3 to 5 carbon atoms;

an aminoalkanoylamino group having from 2 to 7 carbon atoms, in which the amino group of the aminoalkanoyl moiety is unsubstituted or substituted by one or two substituents, which may be the same or different, selected from the Substituents C below, and in which the alkanoyl moiety may be unsubstituted or substituted by a phenyl group or by an alkylthio group having from 1 to 3 carbon atoms;

Substituents B comprise:

an alkyl group having from 1 to 3 carbon atoms;

an alkanoyl group having from 2 to 3 carbon atoms;

a haloalkanoyl group having from 2 to 3 carbon atoms;

an aralkyl group having from 7 to 19 carbon atoms;

an alkoxycarbonyl group having from 2 to 5 carbon atoms;

a haloalkoxycarbonyl group having from 3 to 4 carbon atoms;

an arylcarbonyl group having from 7 to 11 carbon atoms;

an aralkyloxycarbonyl group having from 8 to 10 carbon atoms; and an alkoxycarbonylaminoalkanoyl group having from 1 to 4 carbon atoms in the alkoxy moiety and from 2 to 3 carbon atoms in the alkanoyl moiety;

Substituents C comprise:

an alkyl group having from 1 to 3 carbon atoms;

a formyl group;

an alkanoyl group having from 2 to 3 carbon atoms;

a haloakanoyl group having from 2 to 4 carbon atoms;

an alkoxycarbonyl group having from 2 to 9-carbon atoms;

a haloalkoxycarbonyl group having from 3 to 5 carbon atoms;

m=0 or 1; and n=0 or 1;

PROVIDED THAT, when X represents a group of the said formula (II), $R^2$ represents a hydrogen atom, and m and n cannot both be zero;

AND THAT, when X represents a group of the said formula (III), $R^2$ represents an alkyl group having from 1 to 3 carbon atoms, and m and n are both 1.

2. The compounds as claimed in claim 1, wherein:

X represents a group having the said formula (II); and

Substituents A are selected from a halogen atom, a nitro group, a hydroxy group, an alkoxy group having from 1 to 4 carbon atoms, an aralkyloxy group having from 7 to 11 carbon atoms, an amino group, an alkanoylamino group having from 1 to 4 carbon atoms, and a haloalkanoylamino group having from 2 to 4 carbon atoms.

3. Compounds as claimed in claim 1, wherein:

X represents a group having the said formula (III) in which the substituent Z—NH— is attached at the para-position of the phenyl ring.

4. Compounds as claimed in claim 1, wherein:

X represents a group having the said formula (II); and

Y represents a phenyl group which is substituted at the para-position with an alkylsulfonylamino group having from 1 to 3 carbon atoms, an alkoxycarbonylamino group having from 2 to 5 carbon atoms, a haloalkoxycarbonylamino group having from 3 to 5 carbon atoms, an aminoalkanoylamino group having from 2 to 7 carbon atoms (in which the amino group of the aminoalkanoyl moiety may be unsubstituted or substituted by one or two substituents, which may be the same or different, selected from said Substituents C, and in which the alkanoyl moiety may be unsubstituted or substituted by a phenyl group or by an alkylthio group having from 1 to 3 carbon atoms), or a saturated 5- or 6-membered heterocyclylcarbonylamino group containing nitrogen as a ring atom (in which said nitrogen ring atom may be unsubstituted or substituted by a substituent selected from said Substituents C, and in which the carbonylamino group is attached to an atom other than said nitrogen ring atom).

5. Compounds as claimed in claim 1, wherein:

X represents a group having the said formula (II);

$R^1$ represents a methyl, ethyl, isopropyl or sec-butyl group;

$R^3$ represents a hydrogen atom, or a methyl or ethyl group;

Y represents a phenyl, pyridyl, furyl, thienyl, oxazolyl or thiazolyl group which may be unsubstituted or substituted with 1 or 2 substituents selected from the Substituents $A^1$ defined below;

Substituents $A^1$ comprise a fluorine atom, a chlorine atom, a bromine atom, a nitro group, a hydroxy group, an alkoxy group having from 1 to 3 carbon atoms, an aralkyloxy group having from 7 to 10 carbon atoms, an amino group, an alkanoylamino group having 1 or 2 carbon atoms, a fluorine-, chlorine- or bromine-substituted alkanoylamino group having 2 or 3 carbon atoms, an alkylsulfonylamino group having from 1 to 3 carbon atoms, an alkoxycarbonylamino group having 2 or 3 carbon atoms, an aminoalkanoylamino group having from 2 to 5 carbon atoms in which the amino group of the aminoalkanoyl moiety may be unsubstituted or substituted by a group which is selected from the Substituents $C^1$ defined below; and Substituents $C^1$ comprise an alkyl group having 1 or 2 carbon atoms; a formyl group, an alkanoyl group having 2 or 3 carbon atoms which may be unsubstituted or substituted by from 1 to 3 halogen atoms and an alkoxycarbonyl group having 2 or 3 carbon atoms.

6. A compound as claimed in claim 5, wherein:

$R^1$ represents a methyl or ethyl group;

$R^3$ represents a methyl or ethyl group;

Y represents a furyl, thienyl, thiazolyl, pyridyl or phenyl group which may be unsubstituted or substituted with 1 or 2 substituents selected from the Substituents $A^2$ defined below;

Substituents $A^2$ comprise a fluorine atom, a chlorine atom, a bromine atom, a hydroxy group, a methoxy group, an ethoxy group, a benzyloxy group, an amino group, an acetylamino group, a monochloroacetylamino group, a monobromoacetylamino group, a trifluoroacetylamino group, an alkylsulfonylamino group having 1 or 2 carbon atoms, an aminoalkanoylamino group having 2 or 3 carbon atoms in from the Substituents $C^2$ defined below, and Substituents $C^2$ comprise a methyl group, an alkanoyl group having 2 or 3 carbon atoms, and an alkoxycarbonyl group having 2 or 3 carbon atoms.

7. A compound as claimed in claim 5, wherein Y represents a phenyl group which may be unsubstituted or substituted at the para-position with a substituent selected from a fluorine atom, a chlorine atom, a bromine atom, a hydroxy group, a methoxy group, an ethoxy group, a benzyloxy group, an amino group, an acetylamino group, a monochloroacetylamino group, a monobromoacetylamino group, a trifluoroacetylamino group, an alkylsulfonylamino group having 1 or 2 carbon atoms, an acetylaminoacetylamino group, and an alkoxycarbonylaminoalkanoylamino group having 1 or 2 carbon atoms in its alkyl moiety and 2 or 3 carbon atoms in its alkanoylamino moiety.

8. A compound as claimed in claim 5, wherein:

$R^1$ represents an ethyl group;

$R^3$ represents a methyl group;

Y represents a phenyl group, or a phenyl group substituted in the para-position with a methylsulfonylamino group or with a methoxycarbonylaminoacetylamino group; and m=0 and n=1.

9. A compound as claimed in claim 1, wherein:

X represents a group having the said formula (III);.

Z represents an alkanoyl group having 2 or 3 carbon atoms, an alkylsulfonyl group having from 1 to 3 carbon atoms, an alkoxycarbonyl group having 2 or 3 carbon atoms, an aminoalkanoyl group having from 2 to 6 carbon atoms (in which the amino group may be unsubstituted or substituted by 1 or 2 substituents, which may be the same or different, selected from the Substituents $B^1$ defined below, and the alkanoyl group may be unsubstituted or substituted with a phenyl group or with an alkylthio group having 1 or 2 carbon atoms; and Substituents $B^1$ comprise an alkyl group having from 1 to 3 carbon atoms, an alkanoyl group having 2 or 3 carbon atoms, an alkoxycarbonyl group having from 2 to 5 carbon atoms, an arylcarbonyl group having from 7 to 11 carbon atoms, and an alkoxycarbonylaminoalkanoyl group in which the alkoxycarbonyl moiety has from 2 to 5 carbon atoms and the alkanoyl moiety has 2 or 3 carbon atoms.

10. A compound as claimed in claim 9, wherein:

$R^1$ represents a methyl or ethyl group;

Z represents an alkanoyl group having 2 or 3 carbon atoms, an alkylsulfonyl group having from 1 to 3 carbon atoms, an aminoalkanoyl group having from 2 to 5 carbon atoms (in which the amino group may be substituted by 1 or 2 substituents selected from the Substituents $B^2$ defined below, and the alkanoyl group may be unsubstituted or substituted by a methylthio group; and Substituents $B^2$ comprise an alkyl group having from 1 to 3 carbon atoms, an alkanoyl group having 2 or 3 carbon atoms, an alkoxycarbonyl group having from 2 to 5 carbon atoms, and an arylcarbonyl group having from 7 to 11 carbon atoms.

11. A compound as claimed in claim 9, wherein the substituent Z—NH— is present in the para-position on the phenyl ring of the group of said formula (III), and Z represents an alkylsulfonyl group having 2 or 3 carbon atoms, an aminoalkanoyl group having from 2 to 4 carbon atoms in which the amino group may originally be substituted by 1 or 2 substituents selected from the Substituents $B^2$ defined below; and Substituents $B^2$ comprise an alkyl group having from 1 to 3 carbon atoms, an alkanoyl group having 2 or 3 carbon atoms, an alkoxycarbonyl group having from 2 to 5 carbon atoms, and an arylcarbonyl group having from 7 to 11 carbon atoms.

12. A compound as claimed in claim 9, wherein:

$R^1$ represents an ethyl group;

$R^2$ represents a methyl group;

p is 0;

the substituent Z—NH— is present in the para-position on the phenyl ring;

Z represents an aminoalkanoyl group having 2 or 3 carbon atoms in which the amino group may be unsubstituted or substituted by a substituent selected from the Substituents $B^3$ defined below; and Substituents $B^3$ comprise an alkyl group having from 1 to 3 carbon atoms, an alkanoyl group having 2 or 3 carbon atoms, and an alkoxycarbonyl group having 2 or 3 carbon atoms.

13. A compound 13-(α-methoxyiminophenylacetoxy)milbemycin $A_3$, selected from:

13-(α-Methoxyiminophenylacetoxy)milbemycin $A_4$ (isomer A);

13-(α-Methoxyiminophenylacetoxy)milbemycin $A_4$ (isomer B);

13-[2-Methoxyimino-2-(4-acetylaminoacetylaminophenyl)ethoxy]milbemycin $A_4$;

13-[α-Methoxyimino-(4-methanesulfonylaminophenyl)acetoxy]milbemycin $A_4$;

13-[α-Methoxyimino-(4-acetylaminoacetylaminophenyl)acetoxy]milbemycin $A_4$;

13-[α-Methoxyimino-(4-methoxycarbonylaminoacetylaminophenyl)acetoxy]milbemycin $A_3$;

13-[α-Methoxyimino-(4-methoxycarbonylaminoacetylaminophenyl)acetoxy]milbemycin $A_4$;

13-[2-(4-Methoxycarbonylaminoacetylaminophenyl)-2-methylpropionyloxy]milbemycin $A_3$;

13-[2-(4-Methoxycarbonylaminoacetylaminophenyl)-2-methylpropionyloxy]milbemycin $A_4$;

13-[2-(4-Benzoylaminoacetylaminophenyl)-2-methylpropionyloxy]milbemycin $A_4$;

13-[2-(4-(N-Methyl)methoxycarbonylaminoacetylaminophenyl)-2-methylpropionyloxy]milbemycin $A_4$;

13-[2-[4-{2-(Methoxycarbonylamino)propionylamino}phenyl]-2-methylpropionyloxy]milbemycin $A_4$;

13-[2-[4-{2-(Methoxycarbonylamino)-2-methylpropionylamino}phenyl]-2-methylpropionyloxy]milbemycin $A_4$; and 13-[2-[4-[(1-Methoxycarbonylpyrrolidine)-2-carbonylamino]phenyl]-2-methylpropionyloxy]milbemycin $A_4$.

14. A compound as claimed in claim 13 designated 13-(α-methoxyiminophenylacetoxy)milbemycin $A_4$, (isomer A).

15. A compound as claimed in claim 13 designated 13-(α-methoxyiminophenylacetoxy)milbemycin $A_4$, (isomer B).

16. A compound as claimed in claim 13 designated 13-(α-methoxyiminophenylacetoxy)milbemycin $A_3$.

17. An anthelmintic, acaricidal and insecticidal composition comprising an anthelmintic, acaricidal and insecticidal compound in admixture with an agriculturally or horticulturally acceptable carrier or diluent, wherein said compound is selected from the compounds of formula (I) as claimed in claim 1.

18. An anthelmintic, acaricidal and insecticidal composition comprising an anthelmintic, acaricidal and insecticidal compound in admixture with an agriculturally or horticulturally acceptable carrier or diluent, wherein said compound is selected from the compounds of formula (I) as claimed in claim 2.

19. An anthelmintic, acaricidal and insecticidal composition comprising an anthelmintic, acaricidal and insecticidal compound in admixture with an agriculturally or horticulturally acceptable carrier or diluent, wherein said compound is selected from the compounds of formula (I) as claimed in claim 3.

20. An anthelmintic, acaricidal and insecticidal composition comprising an anthelmintic, acaricidal and insecticidal compound in admixture with an agriculturally or horticulturally acceptable carrier or diluent, wherein said compound is selected from the compounds of formula (I) as claimed in claim 4.

21. An anthelmintic, acaricidal and insecticidal composition comprising an anthelmintic, acaricidal and insecticidal compound in admixture with an agriculturally or horticulturally acceptable carrier or diluent, wherein said compound is selected from the the group consisting of:

13-(α-Methoxyiminophenylacetoxy)milbemycin $A_4$ (isomer A);
13-(α-Methoxyiminophenylacetoxy)milbemycin $A_4$ (isomer B);
13-(α-methoxyiminophenylacetoxy)milbemycin $A_3$,
13-[2-Methoxyimino-2-(4-acetylaminoacetylaminophenyl)ethoxy]milbemycin $A_4$;
13-[α-Methoxyimino-(4-methanesulfonylaminophenyl)acetoxy]milbemycin $A_4$;
13-[α-Methoxyimino-(4-acetylaminoacetylaminophenyl)acetoxy]milbemycin $A_4$;
13-[α-Methoxyimino-(4-methoxycarbonylaminoacetylaminophenyl)acetoxy]milbemycin $A_3$;
13-[α-Methoxyimino-(4-methoxycarbonylaminocenylaminophenyl)acetoxy]milbemycin $A_4$;
13-[2-(4-Methoxycarbonylaminoacetylaminophenyl)-2-methylpropionyloxy]milbemycin $A_3$;
13-[2-(4-Methoxycarbonylaminoacetylaminophenyl)-2-methylpropionyloxy]milbemycin $A_4$;
13-[2-(4-Benzoylaminoacetylaminophenyl)-2-methylpropionyloxy]milbemycin $A_4$;
13-[2-(4-(N-Methyl)methoxycarbonylaminoacetylaminophenyl)-2-methylpropionyloxy]milbemycin $A_4$;
13-[2-[4-{2-(Methoxycarbonylamino)propionylamino}phenyl]-2-methylpropionyloxy]milbemycin $A_4$;
13-[2-[4-{2-(Methoxycarbonylamino)-2-methylpropionylamino}phenyl]-2-methylpropionyloxy]milbemycin $A_4$; and
13-[2-[4-[(1-Methoxycarbonylpyrrolidine)-2-carbonylamino]phenyl]-2-methylpropionyloxy]milbemycin $A_4$.

22. A method of protecting plants from damage by parasites selected from the group consisting of acarids, helminths and insects, which comprises applying an active compound to said plants or to parts of or reproductive matter of said plants or to a locus including said plants or parts of said plants or reproductive matter of said plants, wherein the active compound is selected from the compounds of formula (I) as claimed in claim 1.

23. A method of protecting plants from damage by parasites selected from the group consisting of acarids, helminths and insects, which comprises applying an active compound to said plants or to parts of or reproductive matter of said plants or to a locus including said plants or parts of said plants or reproductive matter of said plants, wherein the active compound is selected from the compounds of formula (I) as claimed in claim 2.

24. A method of protecting plants from damage by parasites selected from the group consisting of acarids, helminths and insects, which comprises applying an active compound to said plants or to parts of or reproductive matter of said plants or to a locus including said plants or parts of said plants or reproductive matter of said plants, wherein the active compound is selected from the compounds of formula (I) as claimed in claim 3.

25. A method of protecting plants from damage by parasites selected from the group consisting of acarids, helminths and insects, which comprises applying an active compound to said plants or to parts of or reproductive matter of said plants or to a locus including said plants or parks of said plants or reproductive matter of said plants, wherein the active compound is selected from the compounds of formula (I) as claimed in claim 4.

26. A method of protecting plants from damage by parasites selected from the group consisting of acarids, helminths and insects, which comprises applying an active compound to said plants or to parts of or reproductive matter of said plants or to a locus including said plants or parts of said plants or reproductive matter of said plants, wherein the active compound is selected from the group consisting of:
13-(α-Methoxyiminophenylacetoxy)milbemycin $A_4$ (isomer A);
13-(α-Methoxyiminophenylacetoxy)milbemycin $A_4$ (isomer B);
13-(α-methoxyiminophenylacetoxy)milbemycin $A_3$,
13-[2-Methoxyimino-2-(4-acetylaminoacetylaminophenyl)ethoxy]milbemycin $A_4$;
13-[α-Methoxyimino-(4-methanesulfonylaminophenyl)acetoxy]milbemycin $A_4$;
13-[α-Methoxyimino-(4-acetylaminoacetylaminophenyl)acetoxy]milbemycin $A_4$;
13-[α-Methoxyimino-(4-methoxycarbonylaminoacetylaminophenyl)acetoxy]milbemycin $A_3$;
13-[α-Methoxyimino-(4-methoxycarbonylaminoacetylaminophenyl)acetoxy]milbemycin $A_4$;
13-[2-(4-Methoxycarbonylaminoacetylaminophenyl)-2-methylpropionyloxy]milbemycin $A_3$;
13-[2-(4-Methoxycarbonylaminoacetylaminophenyl)-2-methylpropionyloxy]milbemycin $A_4$;
13-[2-(4-Benzoylaminoacetylaminophenyl)-2-methylpropionyloxy]milbemycin $A_4$;
13-[2-(4-(N-Methyl)methoxycarbonylaminoacetylaminophenyl)-2-methylpropionyloxy]milbemycin $A_4$;
13-[2-[4-{2-(Methoxycarbonylamino)propionylamino}phenyl]-2-methylpropionyloxy]milbemycin $A_4$;
13-[2-[4-{2-(Methoxycarbonylamino)-2-methylpropionylamino}phenyl]-2-methylpropionyloxy]milbemycin $A^4$; and
13-[2-[4-[(1-Methoxycarbonylpyrrolidine)-2-carbonylamino]phenyl]-2-methylpropionyloxy]milbemycin $A_4$.

* * * * *

UNITED STATES PATENT AND TRADEMARK OFFICE
CERTIFICATE OF CORRECTION

PATENT NO. : 5,614,470
DATED : March 25, 1997
INVENTOR(S) : TAKESHIBA et al

It is certified that error appears in the above-identified patent and that said Letters Patent is hereby corrected as shown below:

Column 80, line 63 (Claim 1): after "atoms;" insert --and--.

Column 83, line 10 (Claim 9): delete "(".

Signed and Sealed this

Second Day of March, 1999

Attest:

Q. TODD DICKINSON

*Attesting Officer*   *Acting Commissioner of Patents and Trademarks*